US009546369B2

(12) United States Patent  
Gao et al.

(10) Patent No.: US 9,546,369 B2
(45) Date of Patent: Jan. 17, 2017

(54) MULTICISTRONIC EXPRESSION CONSTRUCTS

(75) Inventors: Guangping Gao, Westborough, MA (US); Jun Xie, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 103 days.

(21) Appl. No.: 13/642,747

(22) PCT Filed: Apr. 22, 2011

(86) PCT No.: PCT/US2011/033596
§ 371 (c)(1),
(2), (4) Date: Jul. 1, 2013

(87) PCT Pub. No.: WO2011/133874
PCT Pub. Date: Oct. 27, 2011

(65) Prior Publication Data
US 2013/0281516 A1    Oct. 24, 2013

Related U.S. Application Data

(60) Provisional application No. 61/327,404, filed on Apr. 23, 2010.

(51) Int. Cl.
*C12N 15/86* (2006.01)
*C12N 15/113* (2010.01)

(52) U.S. Cl.
CPC ........... *C12N 15/1137* (2013.01); *C12N 15/86* (2013.01); *C12N 2750/14143* (2013.01); *C12N 2750/14152* (2013.01); *C12N 2830/205* (2013.01); *C12N 2830/42* (2013.01)

(58) Field of Classification Search
CPC ................ C12N 15/86; C12N 2830/42; C12N 2750/14141; C12N 2750/14143
See application file for complete search history.

(56) References Cited

U.S. PATENT DOCUMENTS

| | | |
|---|---|---|
| 5,043,270 A | 8/1991 | Abrams et al. |
| 5,478,745 A | 12/1995 | Samulski et al. |
| 5,871,982 A | 2/1999 | Wilson et al. |
| 6,001,650 A | 12/1999 | Colosi |
| 6,083,716 A | 7/2000 | Wilson et al. |
| 6,156,303 A | 12/2000 | Russell et al. |
| 6,251,677 B1 | 6/2001 | Wilson et al. |
| 6,365,394 B1 | 4/2002 | Gao et al. |
| 6,475,469 B1 | 11/2002 | Montgomery |
| 6,485,966 B2 | 11/2002 | Gao et al. |
| 6,498,244 B1 | 12/2002 | Patel et al. |
| 6,544,786 B1 | 4/2003 | Xiao et al. |
| 6,821,512 B1 | 11/2004 | Gao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,238,526 B2 | 7/2007 | Wilson et al. |
| 7,247,472 B2 | 7/2007 | Wilson et al. |
| 7,282,199 B2 | 10/2007 | Gao et al. |
| 7,344,872 B2 | 3/2008 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,102,949 B2 | 8/2015 | Gao et al. |
| 9,217,155 B2 | 12/2015 | Gao et al. |
| 9,226,976 B2 | 1/2016 | Flotte et al. |
| 9,272,053 B2 | 3/2016 | Gao et al. |
| 9,284,357 B2 | 3/2016 | Gao et al. |
| 2001/0016355 A1 | 8/2001 | Samulski et al. |
| 2002/0019050 A1 | 2/2002 | Gao et al. |
| 2003/0040101 A1 | 2/2003 | Wilson et al. |
| 2003/0092161 A1 | 5/2003 | Gao et al. |
| 2003/0096399 A1 | 5/2003 | Barber et al. |
| 2003/0110526 A1 | 6/2003 | Brown et al. |

(Continued)

FOREIGN PATENT DOCUMENTS

| | | |
|---|---|---|
| WO | WO 03/042397 | 5/2003 |
| WO | WO 03/093460 | 11/2003 |

(Continued)

OTHER PUBLICATIONS

Li et al. Intronic MicroRNA: Discovery and Biological Implications. DNA and Cell Biology, vol. 26, No. 4, pp. 195-207, 2007.*
Monteys et al. Structure and activity of putative intronic miRNA promoters. RNA, vol. 16, pp. 495-505, Jan. 14, 2010.*
GenBank Accession No. AQ751855.1, GI: 5539013, publicly available Jul. 19, 1999.*
UCSC Genome Browser on Human Feb. 2009 (GRCh37/hg19) Assembly, chr3:50,143,851-50,279,108, printed as p. 1/1 on Sep. 2, 2014.*
Osoegawa et al. A bacterial artificial chromosome library for sequencing the complete human genome. Genome Research, vol. 11, pp. 483-496, 2001.*
GenBank Submission; NCBI, Accession No. AAB95450; Rutledge et al.; Jan. 12, 1998.
GenBank Submission; NCBI, Accession No. AAS99264; Gao et al.; Jun. 24, 2004.
GenBank Submission; NCBI, Accession No. ABA71701; Schmidt et al.; May 10, 2006.
GenBank Submission; NCBI, Accession No. ACB55301; Vandenberghe et al.; Jul. 31, 2008.

(Continued)

*Primary Examiner* — Jennifer Dunston
(74) *Attorney, Agent, or Firm* — Wolf, Greenfield & Sacks, P.C.

(57) ABSTRACT

Some aspects of this invention provide nucleic acid constructs for transgene expression. Some aspects of this invention provide multicistronic nucleic acid constructs, for example, comprising an expression cassette encoding a hairpin RNA and a reporter expression cassette. Some aspects of this invention provide nucleic acid constructs comprising two or more self-complementary nucleic acid sequences, for example, hairpin RNA encoding nucleic acid sequences and AAV inverse terminal repeats. Methods for the use of the constructs in therapy and research are also provided.

23 Claims, 16 Drawing Sheets

(56) References Cited

U.S. PATENT DOCUMENTS

| | | |
|---|---|---|
| 2003/0119191 A1 | 6/2003 | Gao et al. |
| 2003/0138772 A1 | 7/2003 | Gao et al. |
| 2003/0207259 A1 | 11/2003 | Gao et al. |
| 2003/0228282 A1 | 12/2003 | Gao et al. |
| 2004/0136963 A1 | 7/2004 | Wilson et al. |
| 2004/0171807 A1 | 9/2004 | Gao et al. |
| 2005/0014262 A1 | 1/2005 | Gao et al. |
| 2005/0032219 A1 | 2/2005 | Aubourg et al. |
| 2005/0037988 A1 | 2/2005 | Zamore et al. |
| 2005/0069866 A1 | 3/2005 | Wilson et al. |
| 2005/0137153 A1 | 6/2005 | McSwiggen et al. |
| 2006/0018841 A1 | 1/2006 | Arbetman et al. |
| 2006/0063174 A1* | 3/2006 | Turner et al. ............ 435/6 |
| 2006/0093589 A1 | 5/2006 | Warrington et al. |
| 2006/0189564 A1 | 8/2006 | Burright et al. |
| 2006/0292117 A1 | 12/2006 | Loiler et al. |
| 2007/0004042 A1 | 1/2007 | Gao et al. |
| 2007/0036760 A1 | 2/2007 | Wilson et al. |
| 2007/0134203 A1 | 6/2007 | Gao et al. |
| 2007/0243526 A1 | 10/2007 | Kay et al. |
| 2007/0253936 A1* | 11/2007 | Kay et al. ............ 424/93.6 |
| 2007/0292410 A1 | 12/2007 | Cashman et al. |
| 2008/0075737 A1 | 3/2008 | Gao et al. |
| 2008/0075740 A1 | 3/2008 | Gao et al. |
| 2008/0090281 A1 | 4/2008 | Wilson et al. |
| 2008/0219954 A1 | 9/2008 | Gao et al. |
| 2008/0292595 A1 | 11/2008 | Arbetman et al. |
| 2009/0111766 A1 | 4/2009 | Atkinson et al. |
| 2009/0131355 A1 | 5/2009 | Bot et al. |
| 2009/0149409 A1 | 6/2009 | Bohn et al. |
| 2009/0197338 A1 | 8/2009 | Vandenberghe et al. |
| 2010/0028998 A1 | 2/2010 | Roelvink et al. |
| 2010/0104561 A1 | 4/2010 | Zhong et al. |
| 2010/0186103 A1 | 7/2010 | Gao et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0258716 A1 | 10/2011 | Baltimore et al. |
| 2012/0137379 A1 | 5/2012 | Gao et al. |
| 2012/0270930 A1 | 10/2012 | Van Der Maarel et al. |
| 2013/0101558 A1 | 4/2013 | Gao et al. |
| 2013/0109742 A1 | 5/2013 | Hewitt et al. |
| 2013/0195801 A1 | 8/2013 | Gao et al. |
| 2014/0142161 A1 | 5/2014 | Flotte et al. |
| 2014/0296486 A1 | 10/2014 | Gao et al. |
| 2014/0335054 A1 | 11/2014 | Gao et al. |
| 2016/0135438 A1 | 5/2016 | Gao et al. |
| 2016/0186211 A1 | 6/2016 | Flotte et al. |

FOREIGN PATENT DOCUMENTS

| | | |
|---|---|---|
| WO | WO 2005/033321 | 4/2005 |
| WO | WO 2006/031267 A2 | 3/2006 |
| WO | WO 2006/119432 | 11/2006 |
| WO | WO 2007/000668 A2 | 1/2007 |
| WO | WO 2007/127264 A2 | 11/2007 |
| WO | WO 2008/091703 | 7/2008 |
| WO | WO 2008/147839 | 12/2008 |
| WO | WO 2009/130208 | 10/2009 |
| WO | WO 2009/146178 A1 | 12/2009 |
| WO | WO 2010/034314 | 4/2010 |
| WO | WO 2010/071454 A1 | 6/2010 |
| WO | WO 2010/138263 A2 | 12/2010 |
| WO | WO 2013/190059 A1 | 12/2013 |

OTHER PUBLICATIONS

GenBank Submission; NCBI, Accession No. ACB55310; Vandenberghe et al.; Jul. 31, 2008.

GenBank Submission; NCBI, Accession No. NP_049542; Xiao et al.; Mar. 11, 2010.

GenBank Submission; NCBI, Accession No. YP_680426; Ruffing et al.; Nov. 19, 2010.

GenBank Submission; Accession No. ADZ26851; Wilson et al.; Jun. 30, 2005.

Afione et al., In vivo model of adeno-associated virus vector persistence and rescue. J Virol. May 1996;70(5):3235-41.

Akache et al., The 37/67-kilodalton laminin receptor is a receptor for adeno-associated virus serotypes 8, 2, 3, and 9. J Virol. Oct. 2006;80(19):9831-6.

Alisky et al., Gene therapy for amyotrophic lateral sclerosis and other motor neuron diseases. Hum Gene Ther. Nov. 20, 2000;11(17):2315-29.

Ameres et al., Target RNA-directed tailing and trimming purifies the sorting of endo-siRNAs between the two Drosophila argonaute proteins. RNA. Jan. 2011;17(1):54-63. doi: 10.1261/rna.2498411. Epub Nov. 24, 2010.

Ameres et al., Target RNA-directed trimming and tailing of small silencing RNAs. Science. Jun. 18, 2010;328(5985):1534-9. doi: 10.1126/science.1187058.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Bals et al., Transduction of well-differentiated airway epithelium by recombinant adeno-associated virus is limited by vector entry. J Virol. Jul. 1999;73(7):6085-8.

Barcia et al., Intraventricular and intracerebral delivery of anti-epileptic drugs in the kindling model. Neurotherapeutics. Apr. 2009;6(2):337-43.

Bernacki et al., Mucin gene expression during differentiation of human airway epithelia in vitro. Muc4 and muc5b are strongly induced. Am J Respir Cell Mol Biol. Apr. 1999;20(4):595-604.

Berns et al., Biology of adeno-associated virus. Curr Top Microbiol Immunol. 1996;218:1-23.

Berns et al., Detection of adeno-associated virus (AAV)-specific nucleotide sequences in DNA isolated from latently infected Detroit 6 cells. Virology. Dec. 1975;68(2):556-60.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Bukh, A critical role for the chimpanzee model in the study of hepatitis C. Hepatology. Jun. 2004;39(6):1469-75.

Büssing et al., let-7 microRNAs in development, stem cells and cancer. Trends Mol Med. Sep. 2008;14(9):400-9. doi: 10.1016/j.molmed.2008.07.001. Epub Jul. 31, 2008.

Calcedo et al., Worldwide epidemiology of neutralizing antibodies to adeno-associated viruses. J Infect Dis. Feb. 1, 2009;199(3):381-90.

Carè et al., MicroRNA-133 controls cardiac hypertrophy. Nat Med. May 2007;13(5):613-8. Epub Apr. 29, 2007.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chang et al., miR-122, a mammalian liver-specific microRNA, is processed from her mRNA and may downregulate the high affinity

(56) References Cited

OTHER PUBLICATIONS cationic amino acid transporter CAT-1. RNA Biol. Jul. 2004;1(2):106-13. Epub Jul. 1, 2004.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chirmule et al., Humoral immunity to adeno-associated virus type 2 vectors following administration to murine and nonhuman primate muscle. J Virol. Mar. 2000;74(5):2420-5.
Choi et al., Effects of adeno-associated virus DNA hairpin structure on recombination. J Virol. Jun. 2005;79(11):6801-7.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1 -antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes in CNS. Nature Biotechnology, 27; 59-65 2009.
Fu et al., Evaluation of cellular immune responses in subjects chronically infected with HIV type 1. AIDS Res Hum Retroviruses. Jan. 2007;23(1):67-76.
Fu et al., Self-complementary adeno-associated virus serotype 2 vector: global distribution and broad dispersion of AAV-mediated transgene expression in mouse brain. Mol Ther. Dec. 2003;8(6):911-7.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.
Gao et al., Erythropoietin gene therapy leads to autoimmune anemia in macaques. Blood. May 1, 2004;103(9):3300-2. Epub Dec. 24, 2003.
Gao et al., Inadvertent gene transfer of co-packaged rep and cap sequences during the production of AAV vector and its potential impact on vector performance Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., Purification of recombinant adeno-associated virus vectors by column chromatography and its performance in vivo. Hum Gene Ther. Oct. 10, 2000;11(15):2079-91.
Gao et al., RAAV-mediated targeting in adult mice and its potential in generating animal models of tissue-specific somatic transgenics or knock down. Molecular Therapy. May 2008;16(1):S118-S119. Abstract 316.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Graham et al., A new technique for the assay of infectivity of human adenovirus 5 DNA. Virology. Apr. 1973;52(2):456-67.
Gramantieri et al., Cyclin G1 is a target of miR-122a, a microRNA frequently down-regulated in human hepatocellular carcinoma. Cancer Res. Jul. 1, 2007;67(13):6092-9.
Griffiths-Jones et al., miRBase: microRNA sequences, targets and gene nomenclature. Nucleic Acids Res. Jan. 1, 2006;34(Database issue):D140-4.
Grimm et al., Fatality in mice due to oversaturation of cellular microRNA/short hairpin RNA pathways. Nature. May 25, 2006;441(7092):537-41.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001;75(13):6199-203.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hutvágner et al., Sequence-specific inhibition of small RNA function. PLoS Biol. Apr. 2004;2(4):E98. Epub Feb. 24, 2004.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Krützfeldt et al., Silencing of microRNAs in vivo with 'antagomirs'. Nature. Dec. 1, 2005;438(7068):685-9. Epub Oct. 30, 2005.

(56) References Cited

OTHER PUBLICATIONS

Kutay et al., Downregulation of miR-122 in the rodent and human hepatocellular carcinomas. J Cell Biochem. Oct. 15, 2006;99(3):671-8.

Kwiatkowski et al., Clinical, genetic, and pharmacogenetic applications of the Invader assay. Mol Diagn. Dec. 1999;4(4):353-64.

Lanford et al., Therapeutic silencing of microRNA-122 in primates with chronic hepatitis C virus infection. Science. Jan. 8, 2010;327(5962):198-201. Epub Dec. 3, 2009.

Lebherz et al., Gene therapy with novel adeno-associated virus vectors substantially diminishes atherosclerosis in a murine model of familial hypercholesterolemia. J Gene Med. Jun. 2004;6(6):663-72.

Lewis et al., Conserved seed pairing, often flanked by adenosines, indicates that thousands of human genes are microRNA targets. Cell. Jan. 14, 2005;120(1):15-20.

Lewis et al., Prediction of mammalian microRNA targets. Cell. Dec. 26, 2003;115(7):787-98.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Lin et al., Impact of preexisting vector immunity on the efficacy of adeno-associated virus-based HIV-1 Gag vaccines. Hum Gene Ther. Jul. 2008;19(7):663-9.

Liu et al., Biological Differences in rAAV Transduction of Airway Epithelia in Humans and in Old World Non-human Primates. Mol Ther. Dec. 2007;15(12):2114-23. Epub Jul. 31, 2007.

Liu et al., Comparative biology of rAAV transduction in ferret, pig and human airway epithelia. Gene Ther. Nov. 2007;14(21):1543-8. Epub Aug. 30, 2007.

Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.

Lowenstein, Crossing the rubicon. Nat Biotechnol. Jan. 2009;27(1):42-4.

Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Mandel et al., Recombinant adeno-associated viral vectors as therapeutic agents to treat neurological disorders. Mol Ther. Mar. 2006;13(3):463-83. Epub Jan. 18, 2006.

Manfredsson et al., AAV9: a potential blood-brain barrier buster. Mol Ther. Mar. 2009;17(3):403-5.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].

Martin-Duque et al., Direct comparison of the insulating properties of two genetic elements in an adenoviral vector containing two different expression cassettes. Hum Gene Ther. Oct. 2004;15(10):995-1002.

McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.

McCarty et al., Integration of adeno-associated virus (AAV) and recombinant AAV vectors. Annu Rev Genet. 2004;38:819-45.

McCarty et al., Self-complementary recombinant adeno-associated virus (scAAV) vectors promote efficient transduction independently of DNA synthesis. Gene Ther. Aug. 2001;8(16):1248-54.

McCarty, Self-complementary AAV vectors; advances and applications. Mol Ther. Oct. 2008;16(10):1648-56. Epub Aug. 5, 2008.

McLean et al., Gene targeted therapeutics for liver disease in alpha-1 antitrypsin deficiency. Biologics. 2009;3:63-75. Epub Jul. 13, 2009.

Meister et al., Sequence-specific inhibition of microRNA- and siRNA-induced RNA silencing. RNA. Mar. 2004;10(3):544-50.

Mingozzi et al., CD8(+) T-cell responses to adeno-associated virus capsid in humans. Nat Med. Apr. 2007;13(4):419-22. Epub Mar. 18, 2007.

Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.

Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.

Mueller et al., In Vivo AAV Delivered Allele Specific shRNA for the Knockdown of Alpha-1 Antitrypsin. Molecular Therapy May 2010;18(1):S22. Abstract 53.

Mueller et al., In Vivo Allele Specific Knockdown of Mutant Alpha-1 Antitrypsin Using Recombinant AAV Delivered shRNA. Molecular Therapy May 2009;17(1):S313. Abstract 817.

Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.

Mueller et al., The pros and cons of immunomodulatory IL-10 gene therapy with recombinant AAV in a Cftr−/−-dependent allergy mouse model. Gene Ther. Feb. 2009;16(2):172-83. Epub Sep. 25, 2008.

Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.

O'Reilly et al., RNA interference-mediated suppression and replacement of human rhodopsin in vivo. Am J Hum Genet. Jul 2007;81(1):127-35. Epub May 23, 2007.

Propst et al., Prevalence of hepatocellular carcinoma in alpha-1-antitrypsin deficiency. J Hepatol. Dec. 1994;21(6):1006-11.

Rayner et al., MiR-33 contributes to the regulation of cholesterol homeostasis. Science. Jun. 18, 2010;328(5985):1570-3. doi: 10.1126/science.1189862. Epub May 13, 2010.

Roy et al., Characterization of a family of chimpanzee adenoviruses and development of molecular clones for gene transfer vectors. Hum Gene Ther. May 2004;15(5):519-30.

Sambrook et al, "Molecular Cloning. A Laboratory Manual", 2d ed., Cold Spring Harbor Laboratory, New York (1989).

Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.

Schnepp et al., Characterization of adeno-associated virus genomes isolated from human tissues. J Virol. Dec. 2005;79(23):14793-803.

Schwarz et al., Designing siRNA that distinguish between genes that differ by a single nucleotide. PLoS Genet. Sep. 8, 2006;2(9):e140, 1307-1318. Epub Jul. 24, 2006.

Seiler et al., Adeno-associated virus types 5 and 6 use distinct receptors for cell entry. Hum Gene Ther. Jan. 2006;17(1):10-9.

Sen et al., Micromanaging vascular biology: tiny microRNAs play big band. J Vasc Res. 2009;46(6):527-40. doi: 10.1159/000226221. Epub Jun. 30, 2009.

Sivasothy et al., Pathogenic alpha 1-antitrypsin polymers are formed by reactive loop-beta-sheet A linkage. J Biol Chem. Oct. 27, 2000;275(43):33663-8.

Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.

Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.

Tomar et al., Use of adeno-associated viral vector for delivery of small interfering RNA. Oncogene. Aug. 28, 2003;22(36):5712-5.

Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.

(56) References Cited

OTHER PUBLICATIONS

Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Virella-Lowell et al., Enhancing rAAV vector expression in the lung. J Gene Med. Jul. 2005;7(7):842-50.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wu et al., Alpha2,3 and alpha2,6 N-linked sialic acids facilitate efficient binding and transduction by adeno-associated virus types 1 and 6. J Virol. Sep. 2006;80(18):9093-103.
Wu et al., Nerve injection of viral vectors efficiently transfers transgenes into motor neurons and delivers RNAi therapy against ALS. Antioxid Redox Signal. Jul. 2009;11(7):1523-34.
Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Xia et al., Multiple shRNAs expressed by an inducible pol II promoter can knock down the expression of multiple target genes. Biotechniques. Jul. 2006;41(1):64-8.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Yan et al., Unique biologic properties of recombinant AAV1 transduction in polarized human airway epithelia. J Biol Chem. Oct. 6, 2006;281(40):29684-92. Epub Aug. 9, 2006.
Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.
Crowe et al., A comparison in chimpanzees of the immunogenicity and efficacy of live attenuated respiratory syncytial virus (RSV) temperature-sensitive mutant vaccines and vaccinia virus recombinants that express the surface glycoproteins of RSV. Vaccine. Nov. 1993;11(14):1395-404.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Curtin et al., Bidirectional promoter interference between two widely used internal heterologous promoters in a late-generation lentiviral construct. Gene Ther. Mar. 2008;15(5):384-90. doi: 10.1038/sj.gt.3303105. Epub Jan. 24, 2008.
Czech, MicroRNAs as therapeutic targets. N Engl J Med. Mar. 16, 2006;354(11):1194-5.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., A model system for in vivo gene transfer into the central nervous system using an adenoviral vector. Nat Genet. Mar. 1993;3(3):219-23.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11:20.
Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Elmén et al., LNA-mediated microRNA silencing in non-human primates. Nature. Apr. 17, 2008;452(7189):896-9. Epub Mar. 26, 2008.
Engelhardt et al., Adenovirus-mediated transfer of the CFTR gene to lung of nonhuman primates: biological efficacy study. Hum Gene Ther. Dec. 1993;4(6):759-69.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fire et al., Potent and specific genetic interference by double-stranded RNA in Caenorhabditis elegans. Nature. Feb. 19, 1998;391(6669):806-11.
Yu et al., let-7 regulates self renewal and tumorigenicity of breast cancer cells. Cell. Dec. 14, 2007;131(6):1109-23.
Zabner et al., Adeno-associated virus type 5 (AAV5) but not AAV2 binds to the apical surfaces of airway epithelia and facilitates gene transfer. J Virol. Apr. 2000;74(8):3852-8.
Zern et al., A novel SV40-based vector successfully transduces and expresses an alpha 1-antitrypsin ribozyme in a human hepatoma-derived cell line. Gene Ther. Jan. 1999;6(1):114-20.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.
Zolotukhin et al., Production and purification of serotype 1, 2, and 5 recombinant adeno-associated viral vectors. Methods. Oct. 2002;28(2):158-67.

(56) References Cited

OTHER PUBLICATIONS

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Grimm et al., Therapeutic application of RNAi: is mRNA targeting finally ready for prime time? J Clin Invest. Dec. 2007;117(12):3633-41.
Loiler et al., Targeting recombinant adeno-associated virus vectors to enhance gene transfer to pancreatic islets and liver. Gene Ther. Sep. 2003;10(18):1551-8.
Matalon et al., Adeno-associated virus-mediated aspartoacylase gene transfer to the brain of knockout mouse for canavan disease. Mol Ther. May 2003;7(5 Pt 1):580-7.
Naldini, Ex vivo gene transfer and correction for cell-based therapies. Nat Rev Genet. May 2011;12(5):301-15. doi: 10.1038/nrg2985. Epub Mar. 29, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Tenenbaum et al., Recombinant AAV-mediated gene delivery to the central nervous system. J Gene Med. Feb. 2004;6 Suppl 1:S212-22.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Arbuthnot et al., Hepatic delivery of RNA interference activators for therapeutic application. Curr Gene Ther. Apr. 2009;9(2):91-103.
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Conlon et al., Ribozyme Approaches towards Down-Regulation of Pi*Z Mutant Human a-1 Anti-Trypsin. Mol. Therapy. 2004;9:S333. Abstract 875.
Cruz et al., The promise of gene therapy for the treatment of alpha-1 antitrypsin deficiency. Pharmacogenomics. Sep. 2007;8(9):1191-8.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Wang et al., The design of vectors for RNAi delivery system. Curr Pharm Des. 2008;14(13):1327-40.
U.S. Appl. No. 14/246,560, filed Apr. 7, 2014, Gao et al.
U.S. Appl. No. 14/445,670, filed Jul. 29, 2014, Gao et al.
PCT/US2012/034446, Oct. 31, 2013, International Preliminary Report on Patentability.
EP 11772784.2, Dec. 6, 2013, Extended European Search Report.
PCT/US2010/032158, Jan. 31, 2011, International Search Report and Written Opinion.
PCT/US2010/032158, Dec. 8, 2011, International Preliminary Report on Patentability.
PCT/US2011/33616, Jun. 24, 2011, Invitation to Pay Additional Fees.
PCT/US2011/33616, Aug. 30, 2011, International Search Report and Written Opinion.
PCT/US2011/33616, Nov. 1, 2012, International Preliminary Report on Patentability.
PCT/US2011/33628, Sep. 6, 2011, Invitation to Pay Additional Fees.
PCT/US2011/33628, Nov. 15, 2011, International Search Report and Written Opinion.
PCT/US2011/33628, Nov. 1, 2012, International Preliminary Report on Patentability.
PCT/US2011/33596, Jul. 20, 2011, International Search Report and Written Opinion.
PCT/US2011/33596, Nov. 1, 2012, International Preliminary Report on Patentability.
PCT/US2012/034446, Nov. 28, 2012, International Search Report and Written Opinion.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Storek et al., Intrathecal long-term gene expression by self-complementary adeno-associated virus type 1 suitable for chronic pain studies in rats. Mol Pain. Jan. 30, 2006;2:4.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Asokan et al., The AAV vector toolkit: poised at the clinical crossroads. Mol Ther. Apr. 2012;20(4):699-708. doi: 10.1038/mt.2011.287. Epub Jan. 24, 2012.
Buning et al., Receptor targeting of adeno-associated virus vectors. Gene Ther. Jul. 2003;10(14):1142-51.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Foti et al. Delivering multiple gene products in the brain from a single adeno-associated virus vector. Gene Ther. Nov. 2009;16(11):1314-1319. Doi:10.1038/gt.2009.106.
Li et al., Protein trans-splicing as a means for viral vector-mediated in vivo gene therapy. Hum Gene Ther. Sep. 2008;19(9):958-64. doi: 10.1089/hum.2008.009.
Lux et al., Green fluorescent protein-tagged adeno-associated virus particles allow the study of cytosolic and nuclear trafficking. J Virol. Sep. 2005;79(18):11776-87.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
U.S. Appl. No. 14/940,574, filed Nov. 13, 2015, Gao et al.
U.S. Appl. No. 14/995,699, filed Jan. 14, 2016, Gao et al.
U.S. Appl. No. 15/007,559, filed Jan. 27, 2016, Gao et al.
U.S. Appl. No. 15/098,833, filed Apr. 14, 2016, Flotte et al.

* cited by examiner

SEQUENCE LISTING

```
<160> NUMBER OF SEQ ID NOS: 20

<210> SEQ ID NO 1
<211> LENGTH: 105
<212> TYPE: DNA
<213> ORGANISM: Artificial Sequence
<220> FEATURE:
<223> OTHER INFORMATION: synthetic polynucleotide

<400> SEQUENCE: 1
ctgcgcgctc gctcgctcac tgaggccgcc cgggcaaagc ccgggcgtcg ggcgaccttt      60
ggtcgcccgg cctcagtgag cgagcgagcg cgcagagagg gagtg                    105

<210> SEQ ID NO 2
<211> LENGTH: 130
<212> TYPE: DNA
<213> ORGANISM: Artificial Sequence
<220> FEATURE:
<223> OTHER INFORMATION: synthetic polynucleotide

<400> SEQUENCE: 2
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag                                                            130

<210> SEQ ID NO 3
```

```
<211> LENGTH: 286
<212> TYPE: DNA
<213> ORGANISM: Artificial Sequence
<220> FEATURE:
<223> OTHER INFORMATION: synthetic polynucleotide

<400> SEQUENCE: 3
tacggtaaat ggcccgcctg gctgaccgcc aacgacccc gcccattgac gtcaataatg      60
acgtatgttc ccatagtaac gccaataggg actttccatt gacgtcaatg ggtggagtat     120
ttacggtaaa ctgcccactt ggcagtacat caagtgtatc atatgccaag tacgccccct    180
attgacgtca atgacggtaa atggcccgcc tggcattatg cccagtacat gaccttatgg    240
gactttccta cttggcagta catctactcg aggccacgtt ctgctt                   286

<210> SEQ ID NO 4
<211> LENGTH: 265
<212> TYPE: DNA
<213> ORGANISM: Artificial Sequence
<220> FEATURE:
<223> OTHER INFORMATION: synthetic polynucleotide

<400> SEQUENCE: 4
tctccccatc tccccccct ccccacccc aattttgtat ttatttattt tttaattatt       60
ttgtgcagcg atggggcgg ggggggggg ggggggcg cgcgccaggc ggggcggggc        120
ggggcgaggg gcggggcggg gcgaggcgga gaggtgcggc ggcagccaat cagagcggcg   180
cgctccgaaa gtttcctttt atggcgaggc ggcggcggcg gcggccctat aaaaagcgaa    240
gcgcgcggcg ggcgggagcg ggatc                                         265

<210> SEQ ID NO 5
<211> LENGTH: 172
<212> TYPE: DNA
<213> ORGANISM: Artificial Sequence
<220> FEATURE:
<223> OTHER INFORMATION: synthetic polynucleotide

<400> SEQUENCE: 5
gaactgaaaa accagaaagt taactggtaa gtttagtctt tttgtctttt atttcaggtc      60
ccggatccgg tggtggtgca aatcaaagaa ctgctcctca gtggatgttg cctttacttc    120
taggcctgta cggaagtgtt acttctgctc taaaagctgc ggaattgtac cc           172

<210> SEQ ID NO 6
<211> LENGTH: 717
<212> TYPE: DNA
<213> ORGANISM: Artificial Sequence
<220> FEATURE:
<223> OTHER INFORMATION: synthetic polynucleotide

<400> SEQUENCE: 6
atggtgagca agggcgagga gctgttcacc ggggtggtgc ccatcctggt cgagctggac      60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctgggcac     420 aagctggagt acaactacaa cagccacaac gtctatatca tggccgacaa gcagaagaac    480
```

```
ggcatcaagg tgaacttcaa gatccgccac aacatcgagg acggcagcgt gcagctcgcc    540
gaccactacc agcagaacac ccccatcggc gacggcccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag      717

<210> SEQ ID NO 7
<211> LENGTH: 196
<212> TYPE: DNA
<213> ORGANISM: Artificial Sequence
<220> FEATURE:
<223> OTHER INFORMATION: synthetic polynucleotide

<400> SEQUENCE: 7
ctcgactgtg ccttctagtt gccagccatc tgttgtttgc ccctcccccg tgccttcctt    60
gaccctggaa ggtgccactc ccactgtcct ttcctaataa aatgaggaaa ttgcatcgca    120
ttgtctgagt aggtgtcatt ctattctggg gggtggggtg gggcaggaca gcaagggga    180 ggattgggaa gacaat                                                     196

<210> SEQ ID NO 8
<211> LENGTH: 255
<212> TYPE: DNA
<213> ORGANISM: Artificial Sequence
<220> FEATURE:
<223> OTHER INFORMATION: synthetic polynucleotide

<400> SEQUENCE: 8
aattccccag tggaaagacg cgcaggcaaa acgcaccacg tgacggagcg tgaccgcgcg    60
ccgagcgcgc gccaaggtcg ggcaggaaga gggcctattt cccatgattc cttcatattt    120
gcatatacga tacaaggctg ttagagagat aattagaatt aatttgactg taaacacaaa    180
gatattagta caaaatacgt gacgtagaaa gtaataattt cttgggtagt ttgcagtttt    240
aaaattatgt tttaa                                                      255

<210> SEQ ID NO 9
<211> LENGTH: 143
<212> TYPE: DNA
<213> ORGANISM: Artificial Sequence
<220> FEATURE:
<223> OTHER INFORMATION: synthetic polynucleotide

<400> SEQUENCE: 9
aatggactat catatgctta ccgtaacttg aaagtatttc gatttcttgg gtttatatat    60
cttgtggaaa ggacgcggga tcccgcttac gctgagtact tcgattcaag agatcgaagt    120
actcagcgta agttttttcc aaa                                             143

<210> SEQ ID NO 10
<211> LENGTH: 398
<212> TYPE: DNA
<213> ORGANISM: Artificial Sequence
<220> FEATURE:
<223> OTHER INFORMATION: synthetic polynucleotide

<400> SEQUENCE: 10
aattccccag tggaaagacg cgcaggcaaa acgcaccacg tgacggagcg tgaccgcgcg    60
ccgagcgcgc gccaaggtcg ggcaggaaga gggcctattt cccatgattc cttcatattt    120
gcatatacga tacaaggctg ttagagagat aattagaatt aatttgactg taaacacaaa    180
```

| | |
|---|---|
| gatattagta caaaatacgt gacgtagaaa gtaataattt cttgggtagt ttgcagtttt | 240 |
| aaaattatgt tttaaaatgg actatcatat gcttaccgta acttgaaagt atttcgattt | 300 |
| cttgggttta tatatcttgt ggaaaggacg cgggatcccg cttacgctga gtacttcgat | 360 |
| tcaagagatc gaagtactca gcgtaagttt tttccaaa | 398 |

<210> SEQ ID NO 11
<211> LENGTH: 397
<212> TYPE: DNA
<213> ORGANISM: Artificial Sequence
<220> FEATURE:
<223> OTHER INFORMATION: synthetic polynucleotide

<400> SEQUENCE: 11

| | |
|---|---|
| gcttttggaa aaaacttacg ctgagtactt cgatctcttg aatcgaagta ctcagcgtaa | 60 |
| gcgggatccc gcgtcctttc cacaagatat ataaacccaa gaaatcgaaa tactttcaag | 120 |
| ttacggtaag catatgatag tccattttaa aacataattt taaaactgca aactacccaa | 180 |
| gaaattatta ctttctacgt cacgtatttt gtactaatat ctttgtgttt acagtcaaat | 240 |
| taattctaat tatctctcta acagccttgt atcgtatatg caaatatgaa ggaatcatgg | 300 |
| gaaataggcc ctcttcctgc ccgaccttgg cgcgcgctcg gcgcgcggtc acgctccgtc | 360 |
| acgtggtgcg ttttgcctgc gcgtctttcc actgggg | 397 |

<210> SEQ ID NO 12
<211> LENGTH: 2147
<212> TYPE: DNA
<213> ORGANISM: Artificial Sequence
<220> FEATURE:
<223> OTHER INFORMATION: synthetic polynucleotide

<400> SEQUENCE: 12

| | |
|---|---|
| tacggtaaat ggcccgcctg gctgaccgcc caacgacccc gcccattgac gtcaataatg | 60 |
| acgtatgttc ccatagtaac gccaataggg actttccatt gacgtcaatg ggtggagtat | 120 |
| ttacggtaaa ctgcccactt ggcagtacat caagtgtatc atatgccaag tacgccccct | 180 |
| attgacgtca atgacggtaa atggcccgcc tggcattatg cccagtacat gaccttatgg | 240 |
| gactttccta cttggcagta catctactcg aggccacgtt ctgcttcact ctccccatct | 300 |
| cccccccctc cccaccccca attttgtatt tatttatttt ttaattattt tgtgcagcga | 360 |
| tgggggcggg ggggggggg gggggggcgc gcgccaggcg gggcggggcg gggcgagggg | 420 |
| cggggcgggg cgaggcggag aggtgcggcg gcagccaatc agagcggcgc gctccgaaag | 480 |
| tttcctttta tggcgaggcg gcggcggcgg cggccctata aaagcgaag cgcgcggcgg | 540 |
| gcggagcgg gatcagccac gcgcggtggcg gccctagagt cgatcgagga actgaaaaac | 600 |
| cagaaagtta actggtaagt ttagtctttt tgtcttttat ttcagaattc cccagtggaa | 660 |
| agacgcgcag gcaaaacgca ccacgtgacg gagcgtgacc gcgcgccgag cgcgcgccaa | 720 |
| ggtcgggcag gaagagggcc tatttcccat gattccttca tatttgcata tacgatacaa | 780 |
| ggctgttaga gagataatta gaattaattt gactgtaaac acaagatat tagtacaaaa | 840 |
| tacgtgacgt agaaagtaat aatttcttgg gtagtttgca gttttaaaat tatgttttaa | 900 |
| aatggactat catatgctta ccgtaacttg aaagtatttc gatttcttgg gtttatatat | 960 |
| cttgtggaaa ggacgcggga tcccgcttac gctgagtact tcgattcaag agatcgaagt | 1020 |
| actcagcgta agttttttcc aaagtcccgg atccggtggt ggtgcaaatc aaagaactgc | 1080 |
| tcctcagtgg atgttgcctt tacttctagg cctgtacgga agtgttactt ctgctctaaa | 1140 |

```
agctgcggaa ttgtacccgc ggccgatcca ccggtcgcca ccatggtgag caagggcgag    1200
gagctgttca ccggggtggt gcccatcctg gtcgagctgg acggcgacgt aaacggccac    1260
aagttcagcg tgtccggcga gggcgagggc gatgccacct acggcaagct gaccctgaag    1320
ttcatctgca ccaccggcaa gctgcccgtg ccctggccca ccctcgtgac caccctgacc    1380
tacggcgtgc agtgcttcag ccgctacccc gaccacatga agcagcacga cttcttcaag    1440
tccgccatgc ccgaaggcta cgtccaggag cgcaccatct tcttcaagga cgacggcaac    1500
tacaagaccc gcgccgaggt gaagttcgag ggcgacaccc tggtgaaccg catcgagctg    1560
aagggcatcg acttcaagga ggacggcaac atcctgggc acaagctgga gtacaactac    1620
aacagccaca acgtctatat catggccgac aagcagaaga acggcatcaa ggtgaacttc    1680
aagatccgcc acaacatcga ggacggcagc gtgcagctcg ccgaccacta ccagcagaac    1740
acccccatcg gcgacggccc cgtgctgctg cccgacaacc actacctgag cacccagtcc    1800
gccctgagca agacccccaa cgagaagcgc gatcacatgg tcctgctgga gttcgtgacc    1860
gccgccggga tcactctcgg catggacgag ctgtacaagt aaagcggcca tcaagcttat    1920
cgataccgtc gactagagct cgctgatcag cctcgactgt gccttctagt tgccagccat    1980
ctgttgtttg cccctccccc gtgccttcct tgaccctgga aggtgccact cccactgtcc    2040
tttcctaata aaatgaggaa attgcatcgc attgtctgag taggtgtcat tctattctgg    2100
ggggtggggt ggggcaggac agcaagggg aggattggga agacaat                  2147

<210> SEQ ID NO 13
<211> LENGTH: 2146
<212> TYPE: DNA
<213> ORGANISM: Artificial Sequence
<220> FEATURE:
<223> OTHER INFORMATION: synthetic polynucleotide

<400> SEQUENCE: 13
tacggtaaat ggcccgcctg gctgaccgcc caacgacccc gcccattgac gtcaataatg      60
acgtatgttc ccatagtaac gccaataggg actttccatt gacgtcaatg ggtggagtat     120
ttacggtaaa ctgcccactt ggcagtacat caagtgtatc atatgccaag tacgccccct     180
attgacgtca atgacggtaa atggcccgcc tggcattatg cccagtacat gaccttatgg     240
gactttccta cttggcagta catctactcg aggccacgtt ctgcttcact ctcccccatct     300 cccccccctc cccaccccca attttgtatt tatttatttt ttaattattt tgtgcagcga     360
tgggggcggg ggggggggg gggggggcgc gcgccaggcg gggcggggcg gggcgagggg     420
cggggcgggg cgaggcggag aggtgcggcg gcagccaatc agagcggcgc gctccgaaag     480 tttccttta tggcgaggcg gcggcggcgg cggccctata aaaagcgaag cgcgcggcgg     540
gcgggagcgg gatcagccac cgcggtggcg gccctagagt cgatcgagga actgaaaaac     600
cagaaagtta actggtaagt ttagtctttt tgtcttttat ttcaggcttt tggaaaaaac     660
ttacgctgag tacttcgatc tcttgaatcg aagtactcag cgtaagcggg atcccgcgtc     720
ctttccacaa gatatataaa cccaagaaat cgaaatactt tcaagttacg gtaagcatat     780
gatagtccat tttaaaacat aattttaaaa ctgcaaacta cccaagaaat tattactttc     840
tacgtcacgt attttgtact aatatctttg tgtttacagt caaattaatt ctaattatct     900
ctctaacagc cttgtatcgt atatgcaaat atgaaggaat catgggaaat aggccctctt     960
cctgcccgac cttggcgcgc gctcggcgcg cggtcacgct ccgtcacgtg gtgcgttttg    1020
```

-continued

```
cctgcgcgtc tttccactgg gggtcccgga tccggtggtg gtgcaaatca aagaactgct    1080
cctcagtgga tgttgccttt acttctaggc ctgtacggaa gtgttacttc tgctctaaaa    1140
gctgcggaat tgtacccgcg gccgatccac cggtcgccac catggtgagc aagggcgagg    1200
agctgttcac cggggtggtg cccatcctgg tcgagctgga cggcgacgta aacggccaca    1260
agttcagcgt gtccggcgag ggcgagggcg atgccaccta cggcaagctg accctgaagt    1320
tcatctgcac caccggcaag ctgcccgtgc cctggcccac cctcgtgacc accctgacct    1380
acggcgtgca gtgcttcagc cgctaccccg accacatgaa gcagcacgac ttcttcaagt    1440
ccgccatgcc cgaaggctac gtccaggagc gcaccatctt cttcaaggac gacggcaact    1500
acaagacccg cgccgaggtg aagttcgagg gcgacaccct ggtgaaccgc atcgagctga    1560
agggcatcga cttcaaggag gacggcaaca tcctggggca caagctggag tacaactaca    1620
acagccacaa cgtctatatc atggccgaca agcagaagaa cggcatcaag gtgaacttca    1680
agatccgcca caacatcgag gacggcagcg tgcagctcgc cgaccactac cagcagaaca    1740
cccccatcgg cgacggcccc gtgctgctgc ccgacaacca ctacctgagc acccagtccg    1800
ccctgagcaa agaccccaac gagaagcgcg atcacatggt cctgctggag ttcgtgaccg    1860
ccgccgggat cactctcggc atggacgagc tgtacaagta aagcggccat caagcttatc    1920
gataccgtcg actagagctc gctgatcagc ctcgactgtg ccttctagtt gccagccatc    1980
tgttgtttgc ccctcccccg tgccttcctt gaccctggaa ggtgccactc ccactgtcct    2040
ttcctaataa aatgaggaaa ttgcatcgca ttgtctgagt aggtgtcatt ctattctggg    2100
gggtggggtg gggcaggaca gcaaggggga ggattgggaa gacaat             2146
```

<210> SEQ ID NO 14
<211> LENGTH: 2101
<212> TYPE: DNA
<213> ORGANISM: Artificial Sequence
<220> FEATURE:
<223> OTHER INFORMATION: synthetic polynucleotide

<400> SEQUENCE: 14

```
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg     120
aagatcaatt cggtacaatt cacgcgtcga cattgattat tgactctggt cgttacataa     180
cttacggtaa atggcccgcc tggctgaccg cccaacgacc ccgcccattg acgtcaataa     240
tgacgtatgt tcccatagta acgccaatag ggactttcca ttgacgtcaa tgggtggagt     300
atttacggta aactgcccac ttggcagtac atcaagtgta tcatatgcca agtacgcccc     360
ctattgacgt caatgacggt aaatggcccg cctggcatta tgcccagtac atgaccttat     420
gggactttcc tacttggcag tacatctact cgaggccacg ttctgcttca ctctccccat     480 ctccccccc tccccacccc caatttttgta tttatttatt ttttaattat tttgtgcagc     540 gatggggcg ggggggggg gggggggggc gcgcgccagg cggggcgggg cgggcgagg        600 ggcggggcgg ggcgaggcgg agaggtgcgg cggcagccaa tcagagcggc gcgctccgaa     660
agtttccttt tatggcgagg cggcggcggc ggcggcccta taaaaagcga agcgcgcggc     720
gggcgggagc gggatcagcc accgcggtgg cggccctaga gtcgatcgag gaactgaaaa     780
accagaaagt taactggtaa gtttagtctt tttgtctttt atttcaggtc ccggatccgg     840
tggtggtgca aatcaaagaa ctgctcctca gtggatgttg cctttacttc taggcctgta     900
cggaagtgtt acttctgctc taaaagctgc ggaattgtac ccgcggccga tccaccggtc     960
```

```
gccaccatgg tgagcaaggg cgaggagctg ttcaccgggg tggtgcccat cctggtcgag    1020
ctggacggcg acgtaaacgg ccacaagttc agcgtgtccg gcgagggcga gggcgatgcc    1080
acctacggca agctgaccct gaagttcatc tgcaccaccg gcaagctgcc cgtgccctgg    1140
cccaccctcg tgaccaccct gacctacggc gtgcagtgct tcagccgcta ccccgaccac    1200
atgaagcagc acgacttctt caagtccgcc atgcccgaag ctacgtcca ggagcgcacc     1260 atcttcttca aggacgacgg caactacaag acccgcgccg aggtgaagtt cgagggcgac    1320
accctggtga accgcatcga gctgaagggc atcgacttca aggaggacgg caacatcctg    1380
gggcacaagc tggagtacaa ctacaacagc cacaacgtct atatcatggc cgacaagcag    1440
aagaacggca tcaaggtgaa cttcaagatc cgccacaaca tcgaggacgg cagcgtgcag    1500
ctcgccgacc actaccagca gaacaccccc atcggcgacg gccccgtgct gctgcccgac    1560
aaccactacc tgagcaccca gtccgccctg agcaaagacc ccaacgagaa gcgcgatcac    1620
atggtcctgc tggagttcgt gaccgccgcc gggatcactc tcggcatgga cgagctgtac    1680
aagtaaagcg gccatcaagc ttatcgatac cgtcgactag agctcgctga tcagcctcga    1740
ctgtgccttc tagttgccag ccatctgttg tttgccccte ccccgtgcct tccttgaccc    1800
tggaaggtgc cactcccact gtcctttcct aataaaatga ggaaattgca tcgcattgtc    1860
tgagtaggtg tcattctatt ctggggggtg gggtggggca ggacagcaag ggggaggatt    1920
gggaagacaa ttaggtagat aagtagcatg gcgggttaat cattaactac aaggaacccc    1980
tagtgatgga gttggccact ccctctctgc gcgctcgctc gctcactgag gccgggcgac    2040
caaaggtcgc ccgacgcccg ggctttgccc gggcggcctc agtgagcgag cgagcgcgca    2100
g                                                                   2101

<210> SEQ ID NO 15
<211> LENGTH: 2499
<212> TYPE: DNA
<213> ORGANISM: Artificial Sequence
<220> FEATURE:
<223> OTHER INFORMATION: synthetic polynucleotide

<400> SEQUENCE: 15
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg    120
aagatcaatt cggtacaatt caaattcccc agtggaaaga cgcgcaggca aaacgcacca    180
cgtgacggag cgtgaccgcg cgccgagcgc gcgccaaggt cgggcaggaa gagggcctat    240
ttcccatgat tccttcatat ttgcatatac gatacaaggc tgttagagag ataattagaa    300
ttaatttgac tgtaaacaca agatattag tacaaaatac gtgacgtaga aagtaataat     360
ttcttgggta gtttgcagtt ttaaaattat gttttaaaat ggactatcat atgcttaccg    420
taacttgaaa gtatttcgat tcttgggtt tatatatctt gtggaaagga cgcgggatcc     480
cgcttacgct gagtacttcg attcaagaga tcgaagtact cagcgtaagt tttttccaaa    540
cgcgtcgaca ttgattattg actctggtcg ttacataact tacggtaaat ggcccgcctg    600
gctgaccgcc caacgacccc gcccattgac gtcaataatg acgtatgttc ccatagtaac    660
gccaataggg actttccatt gacgtcaatg ggtggagtat ttacggtaaa ctgcccactt    720
ggcagtacat caagtgtatc atatgccaag tacgccccct attgacgtca atgacggtaa    780
atggcccgcc tggcattatg cccagtacat gaccttatgg gactttccta cttggcagta    840
```

| | |
|---|---:|
| catctactcg aggccacgtt ctgcttcact ctccccatct ccccccctc cccaccccca | 900 |
| attttgtatt tatttatttt ttaattattt tgtgcagcga tggggcggg ggggggggg | 960 |
| ggggggcgc gcgccaggcg gggcggggcg gggcgaggg cggggcgggg cgaggcggag | 1020 |
| aggtgcggcg gcagccaatc agagcggcgc gctccgaaag tttccttta tggcgaggcg | 1080 |
| gcggcggcgg cggccctata aaagcgaag cgcgcggcg gcgggagcgg gatcagccac | 1140 |
| cgcggtggcg gccctagagt cgatcgagga actgaaaaac cagaaagtta actggtaagt | 1200 |
| ttagtctttt tgtcttttat ttcaggtccc ggatccggtg gtggtgcaaa tcaaagaact | 1260 |
| gctcctcagt ggatgttgcc tttacttcta ggcctgtacg gaagtgttac ttctgctcta | 1320 |
| aaagctgcgg aattgtaccc gcggccgatc caccggtcgc caccatggtg agcaagggcg | 1380 |
| aggagctgtt caccggggtg gtgcccatcc tggtcgagct ggacggcgac gtaaacggcc | 1440 |
| acaagttcag cgtgtccggc gagggcgagg gcgatgccac ctacggcaag ctgaccctga | 1500 |
| agttcatctg caccaccggc aagctgcccg tgcctggcc caccctcgtg accaccctga | 1560 |
| cctacggcgt gcagtgcttc agccgctacc ccgaccacat gaagcagcac gacttcttca | 1620 |
| agtccgccat gcccgaaggc tacgtccagg agcgcaccat cttcttcaag gacgacggca | 1680 |
| actacaagac ccgcgccgag gtgaagttcg agggcgacac cctggtgaac cgcatcgagc | 1740 |
| tgaagggcat cgacttcaag gaggacggca acatcctggg gcacaagctg gagtacaact | 1800 |
| acaacagcca caacgtctat atcatggccg acaagcagaa gaacggcatc aaggtgaact | 1860 |
| tcaagatccg ccacaacatc gaggacggca gcgtgcagct cgccgaccac taccagcaga | 1920 |
| acacccccat cggcgacggc cccgtgctgc tgcccgacaa ccactacctg agcacccagt | 1980 |
| ccgccctgag caaagacccc aacgagaagc gcgatcacat ggtcctgctg gagttcgtga | 2040 |
| ccgccgccgg gatcactctc ggcatggacg agctgtacaa gtaaagcggc catcaagctt | 2100 |
| atcgataccg tcgactagag ctcgctgatc agcctcgact gtgccttcta gttgccagcc | 2160 |
| atctgttgtt tgcccctccc ccgtgccttc cttgaccctg gaaggtgcca ctcccactgt | 2220 |
| cctttcctaa taaaatgagg aaattgcatc gcattgtctg agtaggtgtc attctattct | 2280 |
| gggggtggg gtggggcagg acagcaaggg ggaggattgg gaagacaatt aggtagataa | 2340 |
| gtagcatggc gggttaatca ttaactacaa ggaacccta gtgatggagt tggccactcc | 2400 |
| ctctctgcgc gctcgctcgc tcactgaggc cgggcgacca aggtcgccc gacgcccggg | 2460 |
| ctttgcccgg gcggcctcag tgagcgagcg agcgcgcag | 2499 |

<210> SEQ ID NO 16
<211> LENGTH: 2498
<212> TYPE: DNA
<213> ORGANISM: Artificial Sequence
<220> FEATURE:
<223> OTHER INFORMATION: synthetic polynucleotide

<400> SEQUENCE: 16

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt cggtacaatt cagcttttgg aaaaaactta cgctgagtac ttcgatctct | 180 |
| tgaatcgaag tactcagcgt aagcgggatc ccgcgtcctt tccacaagat atataaaccc | 240 |
| aagaaatcga atactttca agttacggta agcatatgat agtccatttt aaaacataat | 300 |
| tttaaaactg caaactaccc aagaaattat tactttctac gtcacgtatt ttgtactaat | 360 |
| atctttgtgt ttacagtcaa attaattcta attatctctc taacagcctt gtatcgtata | 420 |

```
tgcaaatatg aaggaatcat gggaaatagg ccctcttcct gcccgacctt ggcgcgcgct    480
cggcgcgcgg tcacgctccg tcacgtggtg cgttttgcct gcgcgtcttt ccactggggc    540
gcgtcgacat tgattattga ctctggtcgt tacataactt acggtaaatg gcccgcctgg    600
ctgaccgccc aacgacccg cccattgacg tcaataatga cgtatgttcc catagtaacg    660
ccaataggga ctttccattg acgtcaatgg gtggagtatt tacggtaaac tgcccacttg    720
gcagtacatc aagtgtatca tatgccaagt acgccccta ttgacgtcaa tgacggtaaa    780
tggcccgcct ggcattatgc ccagtacatg accttatggg actttcctac ttggcagtac    840
atctactcga ggccacgttc tgcttcactc tccccatctc ccccccctcc caccccccaa    900
ttttgtattt atttatttt taattatttt gtgcagcgat ggggcgggg gggggggggg    960 gggggcgcg cgccaggcgg ggcggggcgg ggcgagggc ggggcggggc gaggcggaga    1020
ggtgcggcgg cagccaatca gagcggcgcg ctccgaaagt ttccttttat ggcgaggcgg    1080
cggcggcggc ggccctataa aaagcgaagc gcgcggcggg cggagcgggg atcagccacc    1140
gcggtggcgg ccctagagtc gatcgaggaa ctgaaaaacc agaaagttaa ctggtaagtt    1200 tagtctttt gtctttatt tcaggtcccg gatccggtgg tggtgcaaat caaagaactg    1260
ctcctcagtg gatgttgcct ttacttctag gcctgtacgg aagtgttact tctgctctaa    1320
aagctgcgga attgtacccg cggccgatcc accggtcgcc accatggtga gcaagggcga    1380
ggagctgttc accggggtgg tgcccatcct ggtcgagctg gacggcgacg taaacggcca    1440
caagttcagc gtgtccggcg agggcgaggg cgatgccacc tacggcaagc tgaccctgaa    1500
gttcatctgc accaccggca agctgcccgt gccctggccc accctcgtga ccaccctgac    1560
ctacggcgtg cagtgcttca gccgctaccc cgaccacatg aagcagcacg acttcttcaa    1620
gtccgccatg cccgaaggct acgtccagga gcgcaccatc ttcttcaagg acgacggcaa    1680
ctacaagacc cgcgccgagg tgaagttcga gggcgacacc ctggtgaacc gcatcgagct    1740
gaagggcatc gacttcaagg aggacggcaa catcctgggg cacaagctgg agtacaacta    1800
caacagccac aacgtctata tcatggccga caagcagaag aacggcatca aggtgaactt    1860
caagatccgc cacaacatcg aggacggcag cgtgcagctc gccgaccact accagcagaa    1920
cacccccatc ggcgacggcc ccgtgctgct gcccgacaac cactacctga gcacccagtc    1980
cgccctgagc aaagacccca acgagaagcg cgatcacatg gtcctgctgg agttcgtgac    2040
cgccgccggg atcactctcg gcatggacga gctgtacaag taaagcggcc atcaagctta    2100
tcgataccgt cgactagagc tcgctgatca gcctcgactg tgccttctag ttgccagcca    2160
tctgttgttt gcccctcccc cgtgccttcc ttgaccctgg aaggtgccac tcccactgtc    2220
ctttcctaat aaaatgagga aattgcatcg cattgtctga gtaggtgtca ttctattctg    2280
gggggtgggg tggggcagga cagcaagggg gaggattggg aagacaatta ggtagataag    2340
tagcatggcg ggttaatcat taactacaag gaaccctag tgatggagtt ggccactccc    2400
tctctgcgcg ctcgctcgct cactgaggcc gggcgaccaa aggtcgcccg acgcccgggc    2460
tttgcccggg cggcctcagt gagcgagcga gcgcgcag                            2498
```

<210> SEQ ID NO 17
<211> LENGTH: 2499
<212> TYPE: DNA
<213> ORGANISM: Artificial Sequence
<220> FEATURE:
<223> OTHER INFORMATION: synthetic polynucleotide

```
<400> SEQUENCE: 17
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
aagatcaatt cggtacaatt cacgcgtcga cattgattat tgactctggt cgttacataa    180
cttacggtaa atggcccgcc tggctgaccg cccaacgacc ccgcccattg acgtcaataa    240
tgacgtatgt tcccatagta acgccaatag ggactttcca ttgacgtcaa tgggtggagt    300
atttacggta aactgcccac ttggcagtac atcaagtgta tcatatgcca agtacgcccc    360
ctattgacgt caatgacggt aaatggcccg cctggcatta tgcccagtac atgaccttat    420
gggactttcc tacttggcag tacatctact cgaggccacg ttctgcttca ctctccccat    480
ctccccccccc tccccacccc caattttgta tttatttatt ttttaattat tttgtgcagc    540
gatggggcg ggggggggg ggggggggc gcgcgccagg cggggcgggg cggggcgagg       600
ggcgggcgg ggcgaggcgg agaggtgcgg cggcagccaa tcagagcggc gcgctccgaa     660
agtttccttt tatggcgagg cggcggcggc ggcggccta taaaaagcga agcgcgcggc     720
gggcgggagc gggatcagcc accgcggtgg cggccctaga gtcgatcgag gaactgaaaa    780
accagaaagt taactggtaa gtttagtctt tttgtctttt atttcagaat tcccagtgg     840
aaagacgcgc aggcaaaacg caccacgtga cggagcgtga ccgcgcgccg agcgcgcgcc    900
aaggtcgggg aggaagaggg cctatttccc atgattcctt catatttgca tatacgatac    960
aaggctgtta gagagataat tagaattaat ttgactgtaa acacaaagat attagtacaa   1020
aatacgtgac gtagaaagta ataatttctt gggtagtttg cagttttaaa attatgtttt   1080
aaaatggact atcatatgct taccgtaact tgaaagtatt tcgatttctt gggtttatat   1140
atcttgtgga aggacgcgg gatcccgctt acgctgagta cttcgattca agagatcgaa   1200
gtactcagcg taagttttt ccaaagtccc ggatccggtg gtggtgcaaa tcaaagaact   1260
gctcctcagt ggatgttgcc tttacttcta ggcctgtacg gaagtgttac ttctgctcta   1320
aaagctgcgg aattgtaccc gcggccgatc caccggtcgc caccatggtg agcaagggcg   1380
aggagctgtt caccggggtg gtgcccatcc tggtcgagct ggacggcgac gtaaacggcc   1440
acaagttcag cgtgtccggc gagggcgagg gcgatgccac ctacggcaag ctgaccctga   1500
agttcatctg caccaccggc aagctgcccg tgccctggcc caccctcgtg accaccctga   1560
cctacggcgt gcagtgcttc agccgctacc ccgaccacat gaagcagcac gacttcttca   1620
agtccgccat gcccgaaggc tacgtccagg agcgcaccat cttcttcaag gacgacggca   1680
actacaagac ccgcgccgag gtgaagttcg agggcgacac cctggtgaac cgcatcgagc   1740
tgaagggcat cgacttcaag gaggacggca acatcctggg gcacaagctg gagtacaact   1800
acaacagcca caacgtctat atcatggccg acaagcagaa gaacggcatc aaggtgaact   1860
tcaagatccg ccacaacatc gaggacggca gcgtgcagct cgccgaccac taccagcaga   1920
acacccccat cggcgacggc cccgtgctgc tgcccgacaa ccactacctg agcacccagt   1980
ccgccctgag caaagacccc aacgagaagc gcgatcacat ggtcctgctg gagttcgtga   2040
ccgccgccgg gatcactctc ggcatggacg agctgtacaa gtaaagcggc catcaagctt   2100
atcgataccg tcgactagag ctcgctgatc agcctcgact gtgccttcta gttgccagcc   2160
atctgttgtt tgcccctccc ccgtgccttc cttgaccctg gaaggtgcca ctcccactgt   2220
cctttcctaa taaaatgagg aaattgcatc gcattgtctg agtaggtgtc attctattct   2280
ggggggtggg gtggggcagg acagcaaggg ggaggattgg gaagacaatt aggtagataa   2340
```

```
gtagcatggc gggttaatca ttaactacaa ggaacccct a gtgatggagt tggccactcc    2400
ctctctgcgc gctcgctcgc tcactgaggc cgggcgacca aggtcgccc gacgcccggg    2460 cttttgcccgg gcggcctcag tgagcgagcg agcgcgcag                          2499

<210> SEQ ID NO 18
<211> LENGTH: 2498
<212> TYPE: DNA
<213> ORGANISM: Artificial Sequence
<220> FEATURE:
<223> OTHER INFORMATION: synthetic polynucleotide

<400> SEQUENCE: 18
ctgcgcgctc gctcgctcac tgaggccgcc cgggcaaagc ccgggcgtcg ggcgaccttt      60
ggtcgcccgg cctcagtgag cgagcagcg cgcagagagg gagtgtagcc atgctctagg     120
aagatcaatt cggtacaatt cacgcgtcga cattgattat tgactctggt cgttacataa    180
cttacggtaa atggcccgcc tggctgaccg cccaacgacc ccgccattg acgtcaataa     240 tgacgtatgt tcccatagta acgccaatag ggactttcca ttgacgtcaa tgggtggagt    300
atttacggta aactgcccac ttggcagtac atcaagtgta tcatatgcca agtacgcccc    360
ctattgacgt caatgacggt aaatggcccg cctggcatta tgcccagtac atgaccttat    420
gggactttcc tacttggcag tacatctact cgaggccacg ttctgcttca ctctccccat    480 ctccccccc tccccacccc caattttgta tttatttatt ttttaattat tttgtgcagc    540 gatggggcg ggggggggg gggggggcc gcgcgccagg cggggcgggg cgggcgagg        600 ggcggggcgg ggcgaggcgg agaggtgcgg cggcagccaa tcagagcggc gcgctccgaa    660
agtttccttt tatggcgagg cggcggcggc ggcggcccta taaaaagcga agcgcgcggc    720
gggcgggagc gggatcagcc accgcggtgg cggccctaga gtcgatcgag gaactgaaaa    780
accagaaagt taactggtaa gtttagtctt tttgtctttt atttcaggct tttggaaaaa    840
acttacgctg agtacttcga tctcttgaat cgaagtactc agcgtaagcg ggatcccgcg    900
tcctttccac aagatatata aacccaagaa atcgaaatac tttcaagtta cggtaagcat    960
atgatagtcc attttaaaac ataatttaa aactgcaaac tacccaagaa attattactt    1020
tctacgtcac gtattttgta ctaatatctt tgtgtttaca gtcaaattaa ttctaattat    1080
ctctctaaca gccttgtatc gtatatgcaa atatgaagga atcatgggaa ataggccctc    1140
ttcctgcccg accttggcgc gcgctcggcg cgcggtcacg ctccgtcacg tggtgcgttt    1200
tgcctgcgcg tctttccact gggggtcccg gatccggtgg tggtgcaaat caaagaactg    1260
ctcctcagtg gatgttgcct ttacttctag gcctgtacgg aagtgttact tctgctctaa    1320
aagctgcgga attgtacccg cggccgatcc accggtcgcc accatggtga gcaagggcga    1380
ggagctgttc accggggtgg tgcccatcct ggtcgagctg gacggcgacg taaacggcca    1440
caagttcagc gtgtccggcg agggcgaggg cgatgccacc tacggcaagc tgaccctgaa    1500
gttcatctgc accaccggca agctgcccgt gccctggccc accctcgtga ccaccctgac    1560
ctacggcgtg cagtgcttca gccgctaccc cgaccacatg aagcagcacg acttcttcaa    1620
gtccgccatg cccgaaggct acgtccagga gcgcaccatc ttcttcaagg acgacggcaa    1680
ctacaagacc cgcgccgagg tgaagttcga gggcgacacc ctggtgaacc gcatcgagct    1740
gaagggcatc gacttcaagg aggacggcaa catcctgggg cacaagctgg agtacaacta    1800
caacagccac aacgtctata tcatggccga caagcagaag aacggcatca aggtgaactt    1860
```

```
caagatccgc cacaacatcg aggacggcag cgtgcagctc gccgaccact accagcagaa    1920
cacccccatc ggcgacggcc ccgtgctgct gcccgacaac cactacctga gcacccagtc    1980
cgccctgagc aaagacccca cgagaagcg cgatcacatg gtcctgctgg agttcgtgac    2040
cgccgccggg atcactctcg gcatggacga gctgtacaag taaagcggcc atcaagctta    2100
tcgataccgt cgactagagc tcgctgatca gcctcgactg tgccttctag ttgccagcca    2160
tctgttgttt gcccctcccc cgtgccttcc ttgaccctgg aaggtgccac tcccactgtc    2220 cttttcctaat aaaatgagga aattgcatcg cattgtctga gtaggtgtca ttctattctg    2280
gggggtgggg tggggcagga cagcaagggg gaggattggg aagacaatta ggtagataag    2340
tagcatggcg ggttaatcat taactacaag gaaccctag tgatggagtt ggccactccc    2400
tctctgcgcg ctcgctcgct cactgaggcc gggcgaccaa aggtcgcccg acgcccgggc    2460
tttgcccggg cggcctcagt gagcgagcga gcgcgcag                           2498

<210> SEQ ID NO 19
<211> LENGTH: 2499
<212> TYPE: DNA
<213> ORGANISM: Artificial Sequence
<220> FEATURE:
<223> OTHER INFORMATION: synthetic polynucleotide

<400> SEQUENCE: 19
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
aagatcaatt cggtacaatt cacgcgtcga cattgattat tgactctggt cgttacataa    180
cttacggtaa atggcccgcc tggctgaccg cccaacgacc cgcccattg acgtcaataa      240 tgacgtatgt tcccatagta acgccaatag ggactttcca ttgacgtcaa tgggtggagt    300
atttacggta aactgcccac ttggcagtac atcaagtgta tcatatgcca agtacgcccc    360
ctattgacgt caatgacggt aaatggcccg cctggcatta tgcccagtac atgaccttat    420
gggactttcc tacttggcag tacatctact cgaggccacg ttctgcttca ctctccccat    480 ctccccccc tccccacccc caattttgta tttatttatt ttttaattat tttgtgcagc      540 gatggggcg gggggggggg ggggggggc gcgcgccagg cggggcgggg cggggcgagg      600
ggcggggcgg ggcgaggcgg agaggtgcgg cggcagccaa tcagagcggc gcgctccgaa    660
agtttccttt tatggcgagg cggcggcggc ggcggcccta taaaaagcga agcgcgcggc    720
gggcgggagc gggatcagcc accgcggtgg cggcctaga gtcgatcgag gaactgaaaa    780
accagaaagt taactggtaa gtttagtctt tttgtctttt atttcaggtc ccggatccgg    840
tggtggtgca aatcaaagaa ctgctcctca gtggatgttg cctttacttc taggcctgta    900
cggaagtgtt acttctgctc taaaagctgc ggaattgtac ccgcggccga tccaccggtc    960
gccaccatgg tgagcaaggg cgaggagctg ttcaccgggg tggtgcccat cctggtcgag   1020
ctggacggcg acgtaaacgg ccacaagttc agcgtgtccg gcgagggcga gggcgatgcc   1080
acctacggca agctgaccct gaagttcatc tgcaccaccg gcaagctgcc cgtgccctgg   1140
cccaccctcg tgaccaccct gacctacggc gtgcagtgct tcagccgcta ccccgaccac   1200
atgaagcagc acgacttctt caagtccgcc atgcccgaag gctacgtcca ggagcgcacc   1260
atcttcttca aggacgacgg caactacaag acccgcgccg aggtgaagtt cgagggcgac   1320
accctggtga accgcatcga gctgaagggc atcgacttca aggaggacgg caacatcctg   1380
gggcacaagc tggagtacaa ctacaacagc cacaacgtct atatcatggc cgacaagcag   1440
```

| | |
|---|---|
| aagaacggca tcaaggtgaa cttcaagatc cgccacaaca tcgaggacgg cagcgtgcag | 1500 |
| ctcgccgacc actaccagca gaacacccc atcggcgacg gccccgtgct gctgcccgac | 1560 |
| aaccactacc tgagcaccca gtccgccctg agcaaagacc ccaacgagaa gcgcgatcac | 1620 |
| atggtcctgc tggagttcgt gaccgccgcc gggatcactc tcggcatgga cgagctgtac | 1680 |
| aagtaaagcg gccatcaagc ttatcgatac cgtcgactag agctcgctga tcagcctcga | 1740 |
| ctgtgccttc tagttgccag ccatctgttg tttgcccctc cccgtgcct tccttgaccc | 1800 |
| tggaaggtgc cactcccact gtcctttcct aataaaatga ggaaattgca tcgcattgtc | 1860 |
| tgagtaggtg tcattctatt ctggggggtg gggtggggca ggacagcaag ggggaggatt | 1920 |
| gggaagacaa aattccccag tggaaagacg cgcaggcaaa acgcaccacg tgacggagcg | 1980 |
| tgaccgcgcg ccgagcgcgc gccaaggtcg gcaggaaga gggcctattt ccatgattc | 2040 |
| cttcatattt gcatatacga tacaaggctg ttagagagat aattagaatt aatttgactg | 2100 |
| taaacacaaa gatattagta caaaatacgt gacgtagaaa gtaataattt cttgggtagt | 2160 |
| ttgcagtttt aaaattatgt tttaaaatgg actatcatat gcttaccgta acttgaaagt | 2220 |
| atttcgattt cttgggttta tatatcttgt ggaaaggacg cgggatcccg cttacgctga | 2280 |
| gtacttcgat tcaagagatc gaagtactca gcgtaagttt tttccaaatt aggtagataa | 2340 |
| gtagcatggc gggttaatca ttaactacaa ggaacccta gtgatggagt tggccactcc | 2400 |
| ctctctgcgc gctcgctcgc tcactgaggc cgggcgacca aaggtcgccc gacgcccggg | 2460 |
| ctttgcccgg gcggcctcag tgagcgagcg agcgcgcag | 2499 |

<210> SEQ ID NO 20
<211> LENGTH: 2498
<212> TYPE: DNA
<213> ORGANISM: Artificial Sequence
<220> FEATURE:
<223> OTHER INFORMATION: synthetic polynucleotide

<400> SEQUENCE: 20

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt cggtacaatt cacgcgtcga cattgattat tgactctggt cgttacataa | 180 |
| cttacggtaa atggcccgcc tggctgaccg cccaacgacc ccgcccattg acgtcaataa | 240 |
| tgacgtatgt tcccatagta acgccaatag ggactttcca ttgacgtcaa tgggtggagt | 300 |
| atttacggta aactgcccac ttggcagtac atcaagtgta tcatatgcca agtacgcccc | 360 |
| ctattgacgt caatgacggt aaatggcccg cctggcatta tgcccagtac atgaccttat | 420 |
| gggactttcc tacttggcag tacatctact cgaggccacg ttctgcttca ctctccccat | 480 |
| ctcccccccc tccccacccc caatttttgta tttatttatt ttttaattat tttgtgcagc | 540 |
| gatggggggcg gggggggggg gggggggggc gcgcgccagg cggggcgggg cggggcgagg | 600 |
| ggcggggcgg ggcgaggcgg agaggtgcgg cggcagccaa tcagagcggc gcgctccgaa | 660 |
| agtttccttt tatggcgagg cggcggcggc ggcggcccta aaaaagcga agcgcgcggc | 720 |
| gggcgggagc gggatcagcc accgcggtgg cggcccctaga gtcgatcgag gaactgaaaa | 780 |
| accagaaagt taactggtaa gtttagtctt tttgtctttt atttcaggtc ccggatccgg | 840 |
| tggtggtgca aatcaaagaa ctgctcctca gtggatgttg cctttacttc taggcctgta | 900 |
| cggaagtgtt acttctgctc taaaagctgc ggaattgtac ccgcggccga tccaccggtc | 960 |

```
gccaccatgg tgagcaaggg cgaggagctg ttcaccgggg tggtgcccat cctggtcgag   1020
ctggacggcg acgtaaacgg ccacaagttc agcgtgtccg gcgagggcga gggcgatgcc   1080
acctacggca agctgaccct gaagttcatc tgcaccaccg gcaagctgcc cgtgccctgg   1140
cccaccctcg tgaccaccct gacctacggc gtgcagtgct tcagccgcta ccccgaccac   1200
atgaagcagc acgacttctt caagtccgcc atgcccgaag gctacgtcca ggagcgcacc   1260
atcttcttca aggacgacgg caactacaag acccgcgccg aggtgaagtt cgagggcgac   1320
accctggtga accgcatcga gctgaagggc atcgacttca aggaggacgg caacatcctg   1380
gggcacaagc tggagtacaa ctacaacagc cacaacgtct atatcatggc cgacaagcag   1440
aagaacggca tcaaggtgaa cttcaagatc cgccacaaca tcgaggacgg cagcgtgcag   1500
ctcgccgacc actaccagca gaacaccccc atcggcgacg gccccgtgct gctgcccgac   1560
aaccactacc tgagcaccca gtccgccctg agcaaagacc ccaacgagaa gcgcgatcac   1620
atggtcctgc tggagttcgt gaccgccgcc gggatcactc tcggcatgga cgagctgtac   1680
aagtaaagcg gccatcaagc ttatcgatac cgtcgactag agctcgctga tcagcctcga   1740
ctgtgccttc tagttgccag ccatctgttg tttgcccctc ccccgtgcct tccttgaccc   1800
tggaaggtgc cactcccact gtcctttcct aataaaatga ggaaattgca tcgcattgtc   1860
tgagtaggtg tcattctatt ctggggggtg ggtggggca ggacagcaag ggggaggatt   1920
gggaagacaa gcttttggaa aaacttacg ctgagtactt cgatctcttg aatcgaagta   1980
ctcagcgtaa gcgggatccc gcgtcctttc cacaagatat ataaacccaa gaaatcgaaa   2040
tactttcaag ttacggtaag catatgatag tccattttaa aacataattt taaaactgca   2100
aactacccaa gaattatta ctttctacgt cacgtatttt gtactaatat ctttgtgttt   2160
acagtcaaat taattctaat tatctctcta acagccttgt atcgtatatg caaatatgaa   2220
ggaatcatgg gaaataggcc ctcttcctgc ccgaccttgg cgcgcgctcg gcgcgcggtc   2280
acgctccgtc acgtggtgcg ttttgcctgc gcgtctttcc actggggtta ggtagataag   2340
tagcatggcg ggttaatcat taactacaag gaaccctag tgatggagtt ggccactccc   2400
tctctgcgcg ctcgctcgct cactgaggcc gggcgaccaa aggtcgcccg acgcccgggc   2460
tttgcccggg cggcctcagt gagcgagcga gcgcgcag                          2498
```

US 9,546,369 B2

MULTICISTRONIC EXPRESSION CONSTRUCTS

RELATED APPLICATIONS

This application is a National Stage Application of PCT/US2011/033596, filed on Apr. 22, 2011, and entitled "MULTICISTRONIC EXPRESSION CONSTRUCTS," which claims priority under 35 U.S.C. §119(e) to U.S. Provisional Application Ser. No. 61/327,404, entitled "MULTICISTRONIC EXPRESSION CONSTRUCTS" filed on Apr. 23, 2010, which is herein incorporated by reference in its entirety.

FIELD OF THE INVENTION

Some aspects of the invention relate to the field of gene expression constructs. Some aspects of the invention relate to viral expression constructs, for example, adeno-associated virus (AAV)-related expression constructs. Some aspects of the invention relate to the field of RNAi.

BACKGROUND OF THE INVENTION

Expression constructs are useful to effect transgene expression in a target cell. Since many useful transgene products are not easily detected in a target cell, expression constructs harboring a reporter cassette are commonly used to monitor transgene delivery and expression. Multicistronic expression constructs, for example, constructs harboring a first expression cassette, e.g. comprising a first promoter and a first encoding nucleic acid sequence, and a second expression cassette, e.g. comprising a second promoter and a second encoding nucleic acid sequence, are particularly useful in the delivery of transgenes encoding non-translated gene products, such as hairpin RNAs, together with a reporter transgene, for example, a fluorescent protein. However, multicistronic expression constructs may be burdened with reduced expression levels of one or more of the included transgenes, for example, because of promoter interference or the presence of incompatible nucleic acid elements in close proximity. If a multicistronic expression construct is part of a viral vector, the inclusion of a hairpin RNA expression cassette may pose additional problems, for example, because the presence of a self-complementary nucleic acid sequence may interfere with the formation of structures necessary for viral reproduction or packaging.

SUMMARY OF THE INVENTION

Some aspects of the invention relate to isolated nucleic acid constructs. Some aspects of this invention relate to isolated gene expression constructs. Some aspects of this invention relate to multicistronic expression constructs, for example, to bicistronic expression constructs. Some aspects of this invention relate to expression constructs comprising an expression cassette containing a self-complementary nucleic acid sequence, for example, a nucleic acid sequence encoding a hairpin-forming RNA. Some aspects of this invention relate to expression constructs comprising an expression cassette containing a self-complementary nucleic acid sequence positioned in proximity to a second self-complementary nucleic acid sequence. Some aspects of this invention relate to methods of engineering nucleic acid constructs comprising a self-complementary nucleic acid sequence and a second expression cassette and/or a second self-complementary nucleic acid sequence, for example, a terminal repeat sequence. Some aspects of this invention relate to viral gene expression constructs. Some aspects of this invention relate to parvovirus-derived expression constructs, for example, to adeno-associated virus (AAV)-derived expression constructs. Some aspects of this invention relate to compositions and kits comprising an expression construct as provided herein. Some aspects of this invention relate to methods of using an expression construct as provided herein to express a nucleic acid comprising a self-complementary sequence in a target cell. Some aspects of this invention relate to the use of constructs as provided herein in methods of inhibiting the expression of a gene product in the target cell by expressing a nucleic acid comprising a self-complementary sequence corresponding to a nucleic acid sequence encoding the gene product. Some aspects of this invention relate to methods of determining a phenotypic change of a cell effected by contacting the cell with an expression construct as described herein. Some aspects of this invention relate to methods involving administering a recombinant AAV (rAAV) expression construct as provided herein to a subject, wherein the rAAV infects a cell of a target tissue of the subject. Some aspects relate to methods of using a nucleic acid construct as provided herein to inhibit expression of a gene in a target cell, for example, a target cell in a subject, by expressing a hairpin RNA in the target cell that comprises a sequence corresponding to a sequence of a nucleic acid encoding a gene product of the gene.

Some aspects of this invention relate to the surprising discovery that an expression cassette positioned within an intron of another expression cassette is efficiently expressed in a target cell. Further, some aspects of this invention relate to the surprising discovery that an expression cassette positioned within an intron of another expression cassette is efficiently expressed in a target cell independent of whether the expression cassettes are in the same orientation or in opposite orientation to each other.

Some aspects of this invention relate to the surprising discovery that an expression cassette comprising a nucleic acid sequence encoding a self-complementary RNA positioned in proximity to an AAV-ITR, can efficiently be expressed if the ITR is a ΔTRS ITR, independent of the orientation of the expression cassette.

Some aspects of this invention relate to the surprising discovery that an expression cassette comprising a nucleic acid sequence encoding a self-complementary RNA positioned in proximity to a functional AAV-ITR only if the expression construct comprises at least about 150 nucleotides between the functional ITR and the nucleic acid sequence encoding the self-complementary RNA.

In some embodiments, the expression construct is a linear DNA or RNA construct. In some embodiments, the expression construct is a circular DNA construct. In some embodiments, the expression construct is a viral expression construct. In some embodiments, the expression construct is a parvovirus-derived construct, for example, an AAV-derived construct. In some embodiments, the expression construct comprises an inverted terminal repeat (ITR). In some embodiments, the expression construct comprises an ITR lacking a functional terminal resolution site (TRS), also referred to as ΔTRS ITR or ΔITR. In some embodiments, the expression construct comprises a nucleic acid sequence encoding a hairpin RNA, for example, a small hairpin RNA (shRNA) or a micro RNA (miRNA). In some embodiments, the expression construct comprises a plurality of expression cassettes. In some embodiments, the expression construct comprises a first and a second expression cassette in the same orientation, with an additional expression cassette optionally present. In some embodiments, the expression construct comprises a first and a second expression cassette in opposite orientation to each other, with an additional expression cassette optionally present. In some embodiments, the expression construct comprises a first expression cassette harboring an intron and the second expression cassette is positioned in the intron of the first expression cassette, either in the same or in opposite orientation to the first expression cassette, with an additional expression cassette optionally present.

Some aspects of this invention provide an isolated nucleic acid construct, comprising a first expression cassette, comprising a nucleic acid encoding a gene product under the control of a first promoter, and an intron, and a second expression cassette, comprising a self-complementary nucleic acid sequence under the control of a second promoter, wherein the second expression cassette is positioned within the intron of the first expression cassette. In some embodiments, the gene product is a reporter. In some embodiments, the reporter is a protein. In some embodiments, the protein is a fluorescent protein, an enzyme catalyzing a reaction yielding a detectable product, or a surface antigen. In some embodiments, the enzyme is a luciferase, a beta-glucuronidase, a chloramphenicol acetyltransferase, an aminoglycoside phosphotransferase, an aminocyclitol phosphotransferase, or a Puromycin N-acetyl-tranferase. In some embodiments, the self-complementary sequence encodes a hairpin RNA. In some embodiments, the hairpin RNA is a small hairpin RNA or a microRNA. In some embodiments, the first promoter is an RNA polymerase II promoter. In some embodiments, the second promoter is an RNA polymerase III promoter. In some embodiments, the second promoter is a U6 or an H1 promoter. In some embodiments, the nucleic acid construct comprises the structure of AAV construct A1 or A2. In some embodiments, the first and the second expression cassette are in the same orientation. In some embodiments, the first and the second expression cassette are in opposite orientations. In some embodiments, the nucleic acid construct is comprised in an expression vector. In some embodiments, the expression vector is a viral vector. In some embodiments, the viral vector is a parvovirus vector, an adenovirus vector, or a retrovirus vector. In some embodiments, the viral vector is an adeno-associated virus vector, a lentivirus vector, or a Moloney murine leukemia virus vector. In some embodiments, the viral construct is an AAV construct. In some embodiments, the AAV construct is a self-complementary AAV construct. In some embodiments, the nucleic acid construct is integrated into the genome of a cell expressing a target gene. In some embodiments, the nucleic acid construct comprises a nucleic acid encoding a hairpin RNA comprising a sequence complementary or corresponding to a sequence of an RNA transcribed from the target gene. In some embodiments, the target gene is a gene is an oncogene, a tumor suppressor gene, a gene involved in neovascularization of tissue, a viral gene, or a gene encoding a receptor mediating uptake of viral particles.

Some aspects of this invention provide a nucleic acid construct, comprising (i) an inverted terminal repeat lacking a functional terminal resolution site (ΔTRS ITR), (ii) a first expression cassette, comprising a nucleic acid encoding a gene product under the control of a first promoter, and (iii) a second expression cassette, comprising a self-complementary nucleic acid sequence under the control of a second promoter, wherein the second expression cassette is positioned between the ΔTRS ITR and the first expression cassette, and wherein (a) the first and the second expression cassette are in opposite orientations, or (b) the first and the second expression cassette are in the same orientation and the nucleic acid construct comprises less than 500 nucleotides between the ΔTRS ITR and the second expression cassette. In some embodiments, the nucleic acid construct is an AAV construct. In some embodiments, the AAV construct is a self-complementary AAV construct. In some embodiments, the gene product is a reporter. In some embodiments, the reporter is a protein. In some embodiments, the protein is a fluorescent protein, an enzyme catalyzing a reaction yielding a detectable product, or a surface antigen. In some embodiments, the enzyme is a luciferase, a beta-glucuronidase, a chloramphenicol acetyltransferase, an aminoglycoside phosphotransferase, an aminocyclitol phosphotransferase, or a Puromycin N-acetyl-tranferase. In some embodiments, the self-complementary nucleic acid sequence encodes a hairpin RNA. In some embodiments, the hairpin RNA is an shRNA or a microRNA. In some embodiments, the first promoter is an RNA polymerase II promoter. In some embodiments, the second promoter is an RNA polymerase III promoter. In some embodiments, the second promoter is a U6 or H1 promoter. In some embodiments, the nucleic acid construct comprises the structure of AAV construct B1 or B2. In some embodiments, the nucleic acid construct is integrated into the genome of a cell expressing a target gene. In some embodiments, the nucleic acid construct comprises a nucleic acid encoding a hairpin RNA comprising a sequence complementary or corresponding to a sequence of an RNA transcribed from the target gene. In some embodiments, the target gene is a gene is an oncogene, a tumor suppressor gene, a gene involved in neovascularization of tissue, a viral gene, or a gene encoding a receptor mediating uptake of viral particles. In some embodiments, the nucleic acid construct comprises less than about 50, less than about 100, less than about 200, less than about 250, less than about 300, less than about 400, less than about 500, less than about 600, less than about 700, less than about 800, less than about 900, or less than about 1000 nucleotides between the ΔTRS ITR and the second expression cassette.

Some aspects of this invention provide a nucleic acid construct, comprising (i) an inverted terminal repeat (ITR), (ii) a first expression cassette, comprising a nucleic acid encoding a gene product under the control of a first promoter, and (iii) a second expression cassette, comprising a self-complementary nucleic acid sequence under the control of a second promoter, wherein the first and the second expression cassette are in opposite orientation, and, optionally, wherein the nucleic acid construct comprises at least 150 nucleotides between the ITR and the second expression cassette. In some embodiments, the nucleic acid construct is an AAV construct. In some embodiments, the AAV construct is a self-complementary AAV construct. In some embodiments, the AAV construct is a non-self-complementary AAV construct, for example, an AAV construct comprising two ITRs with functional terminal resolution sites. In some embodiments, the gene product is a self-complementary nucleic acid, for example, a hairpin RNA. In some embodiments, the gene product is a reporter. In some embodiments, the reporter is a protein. In some embodiments, the protein is a fluorescent protein, an enzyme catalyzing a reaction yielding a detectable product, or a surface antigen. In some embodiments, the enzyme is a luciferase, a beta-glucuronidase, a chloramphenicol acetyltransferase, an aminoglycoside phosphotransferase, an aminocyclitol phosphotransferase, or a Puromycin N-acetyl-tranferase. In some embodiments, the self-complementary nucleic acid sequence encodes a hairpin RNA. In some embodiments, the hairpin RNA is a small hairpin RNA or a microRNA. In some embodiments, the first promoter is an RNA polymerase II promoter. In some embodiments, the second promoter is an RNA polymerase III promoter. In some embodiments, the first and the second promoters are RNA polymerase II promoters. In some embodiments, the first and the second promoters are RNA polymerase III promoters. In some embodiments, the second promoter is a U6 or H1 promoter. In some embodiments, the nucleic acid construct comprises the nucleic acid sequence of AAV constructs D1 or D2. In some embodiments, the nucleic acid construct is integrated into the genome of a cell expressing a target gene. In some embodiments, the nucleic acid construct comprises a nucleic acid encoding a hairpin RNA comprising a sequence complementary or corresponding to a sequence of an RNA transcribed from the target gene. In some embodiments, the target gene is a gene is an oncogene, a tumor suppressor gene, a gene involved in neovascularization of tissue, a viral gene, or a gene encoding a receptor mediating uptake of viral particles. In some embodiments, the nucleic acid construct comprises at least about 200, at least about 300, at least about 400, at least about 500, at least about 600, at least about 700, or at least about 800 nucleotides between the ITR and the second expression cassette.

Some aspects of this invention provide a recombinant AAV construct, comprising any of the nucleic acid constructs or AAV constructs provided herein. Some aspects of this invention provide a plasmid comprising any of the nucleic acid constructs or AAV constructs provided herein. In some embodiments, the plasmid further comprises a bacterial origin of replication and a bacterial selection marker.

Some aspects of this invention provide a composition comprising any of the nucleic acid constructs, AAV constructs, or plasmids provided herein. In some embodiments, the composition further comprises a pharmaceutically acceptable salt.

Some aspects of this invention provide a method, comprising contacting a cell expressing a target gene with any of the nucleic acid constructs, AAV constructs, or plasmids, or compositions as described herein. In some embodiments, the nucleic acid construct, AAV construct, plasmid, or composition comprises a self-complementary nucleic acid sequence which comprises a sequence complementary or corresponding to a sequence of an RNA encoded by the target gene. In some embodiments, the nucleic acid construct, the AAV construct, the plasmid, or the composition comprises a nucleic acid sequence encoding a reporter, and wherein the method further comprises detecting expression of the reporter in the cell. In some embodiments, the method further comprises determining a change in the phenotype of the cell after the contacting. In some embodiments, the change in the phenotype is a change in proliferation rate, change in cell size, change in cell viability, change in cell sensitivity to a drug, change in modulation of a cellular pathway in response to drug treatment, or a change in a level of expression of a gene of interest. In some embodiments, the cell is a cell in a subject and wherein the contacting comprises administering the nucleic acid construct, the recombinant AAV construct, the plasmid, and/or the composition to the subject in an amount sufficient to inhibit expression of the target gene in the cell. In some embodiments, the method comprises administering a recombinant AAV construct to the subject via an intravenous, intraperitoneal, intraocular, intramuscular, intraarticular, intracranial, intranasal, or endobronchial route. In some embodiments, the subject has been diagnosed with a disease and inhibition of the target gene is known to prevent or alleviate a symptom and/or progression of the disease.

Some aspects of this invention provide a kit, comprising a container housing any of the nucleic acid constructs, the AAV constructs, the plasmids, or the compositions provided herein.

Each of the embodiments of the invention can encompass various recitations made herein. It is, therefore, anticipated that each of the recitations of the invention involving any one element or combinations of elements can, optionally, be included in each aspect of the invention.

These and other aspects of the invention, as well as various advantages and utilities will be more apparent with reference to the drawings and detailed description of the invention.

DETAILED DESCRIPTION

Figure 1:
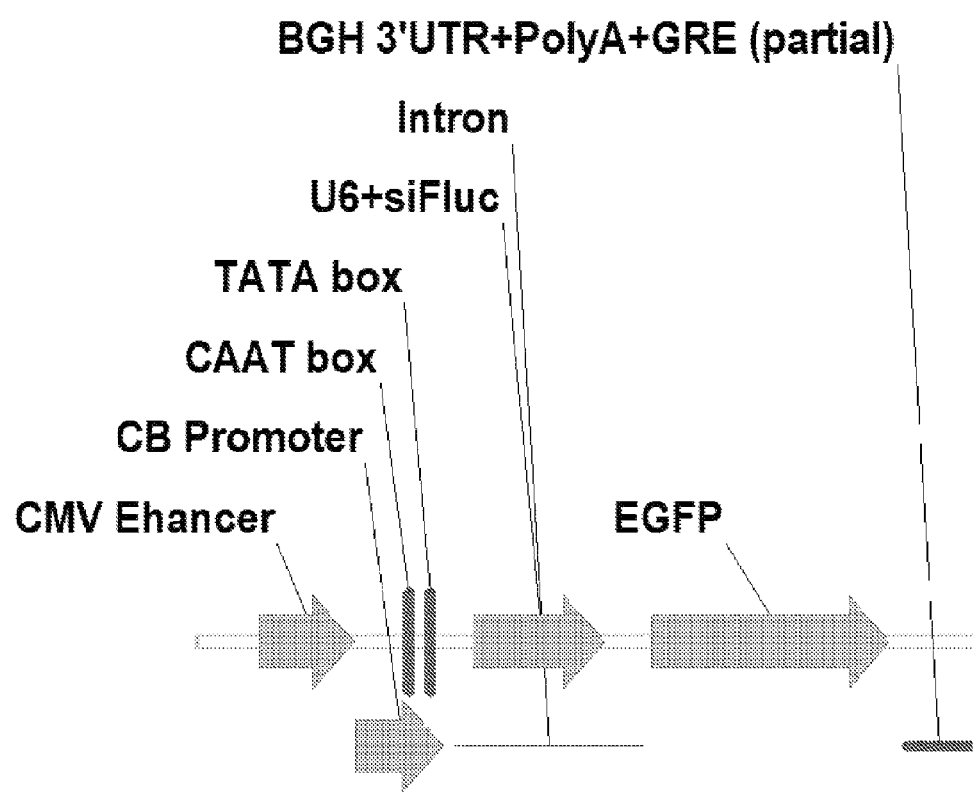
FIG. 1. Map of CMV/CB-intron-U6siFluc-intron-eGFP (A1). Arrows indicate the orientation of the respective nucleic acid construct elements in FIGS. 1-9.
Figure 2:
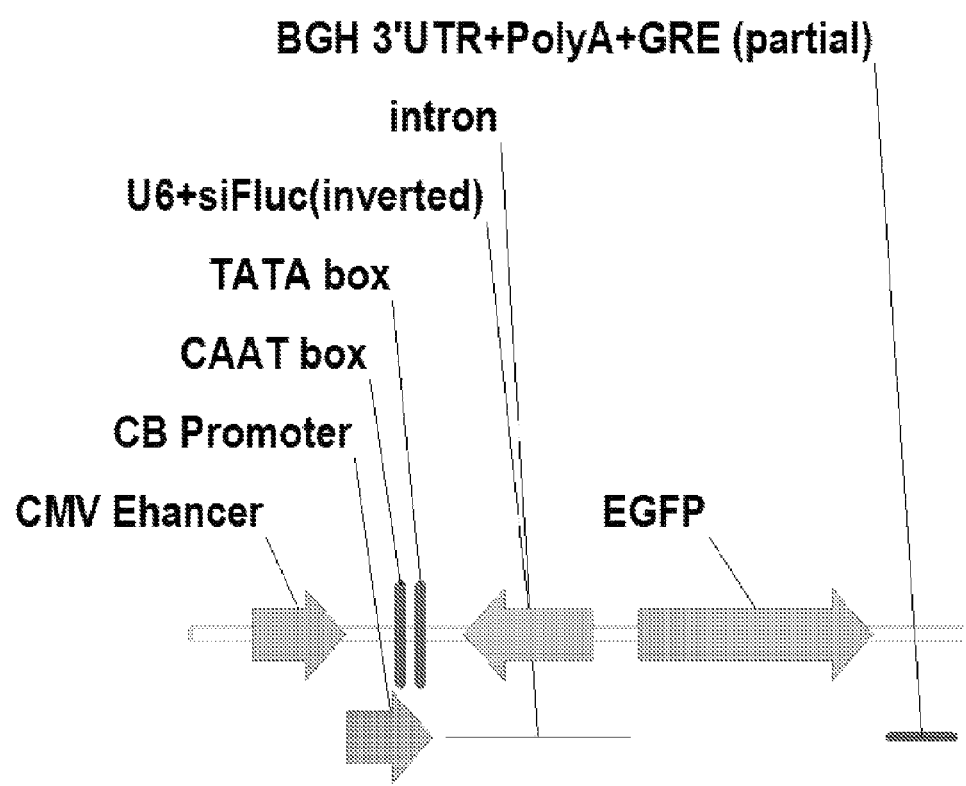
FIG. 2. Map of CMV/CB-intron-U6siFluc$^{inv}$-intron-eGFP (A2).
Figure 3:
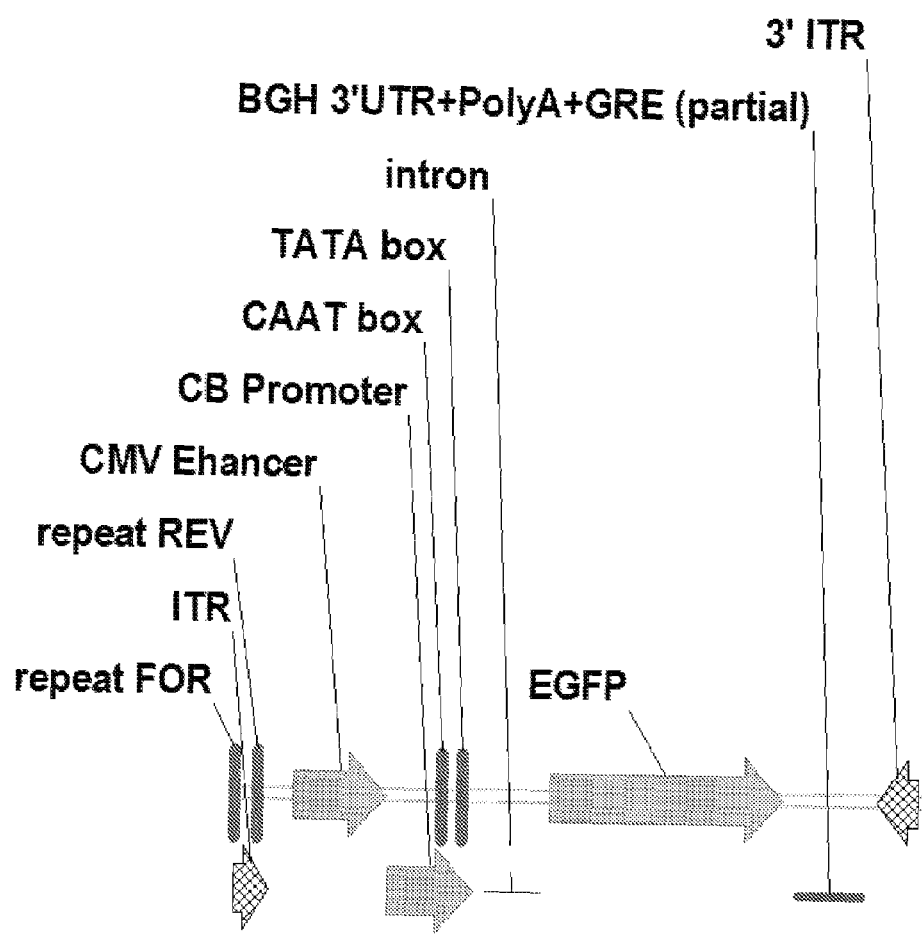
FIG. 3. Map of AAV 5'ΔITR CMV/CB-intron-eGFP 3'ITR (A). ITR: 5' ΔTSR ITR. Repeat FOR: forward repeat of ΔTRS ITR. Repeat REV: reverse repeat of ΔTRS ITR. 3'ITR: functional ITR.
Figure 4:
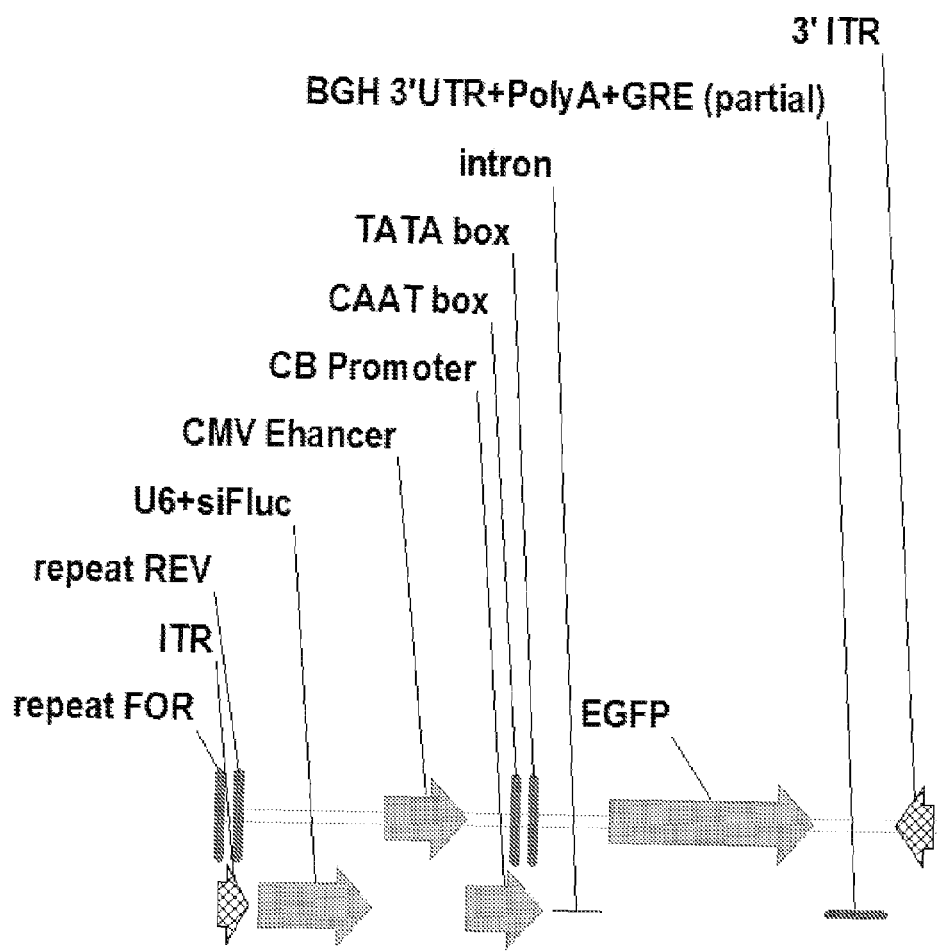
FIG. 4. Map of AAV 5' ΔITR U6shFluc CMV/CB-intron-eGFP 3'ITR(B1).
Figure 5:
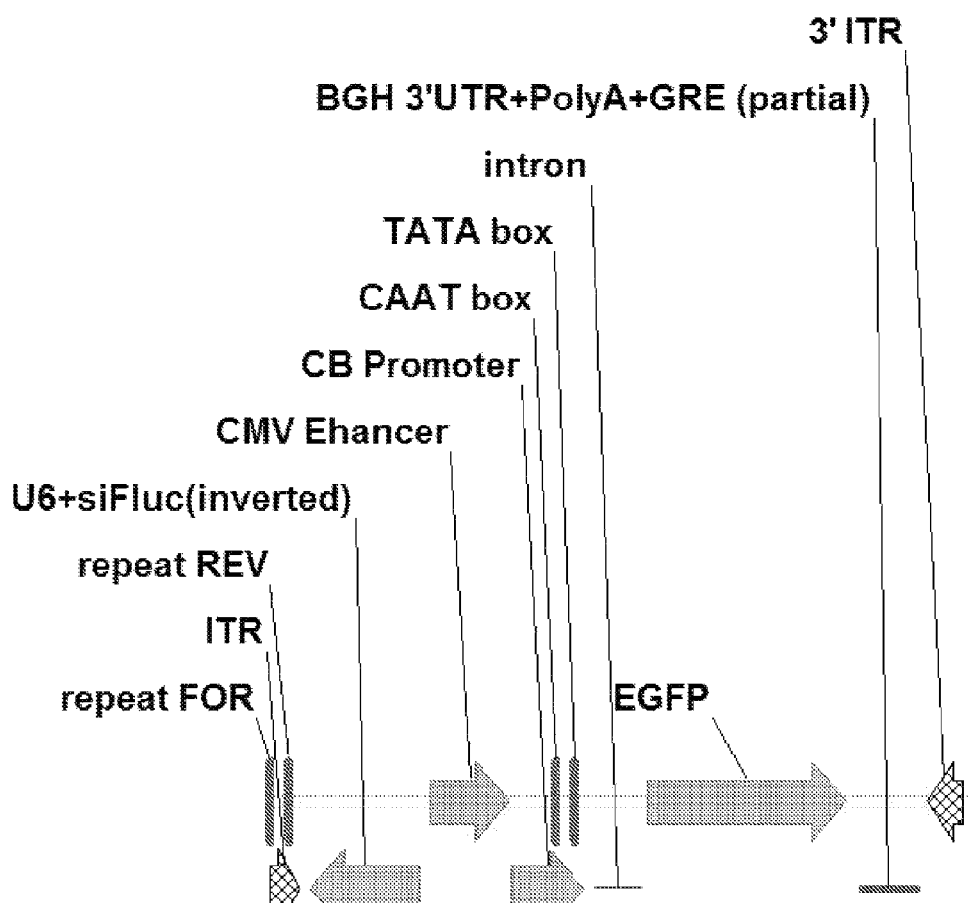
FIG. 5. Map of AAV 5' ΔITR U6shFluc$^{inv}$ CMV/CB-intron-eGFP 3'ITR(B2).
Figure 6:
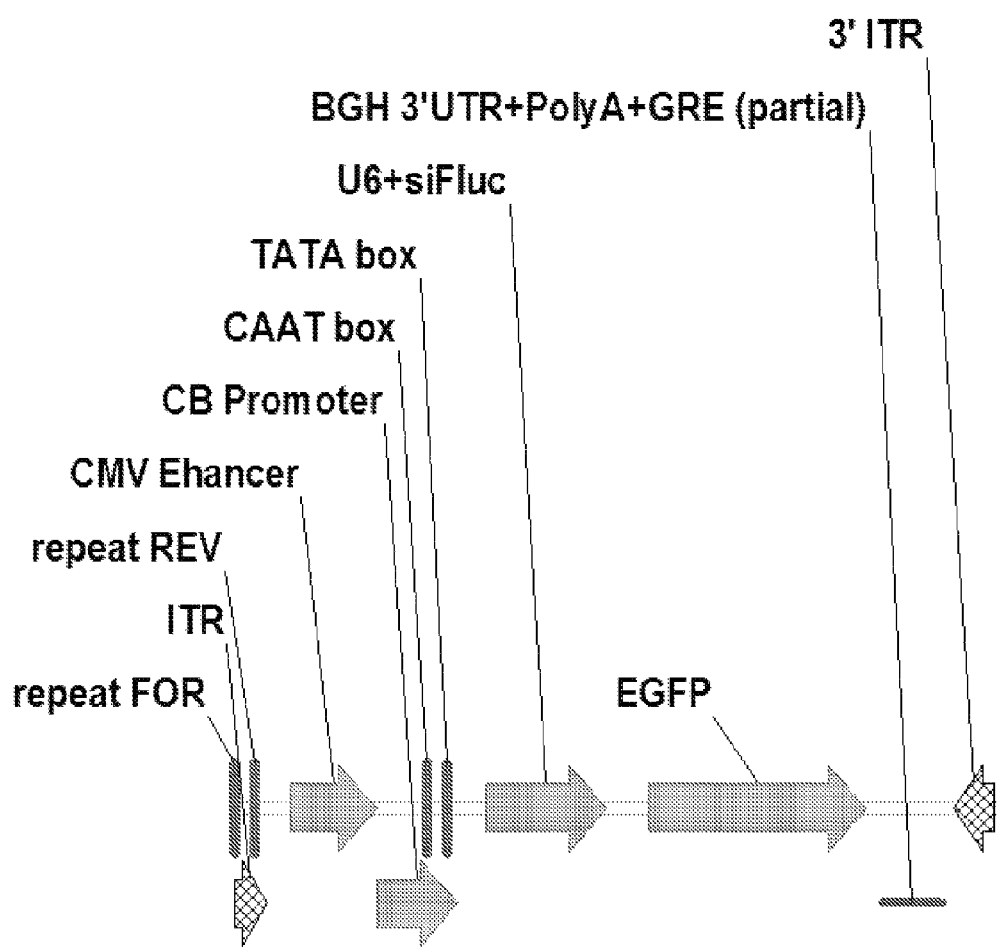
FIG. 6. Map of AAV 5' ΔITR CMV/CB-intron-U6shFluc-intron-eGFP 3'ITR(C1).
Figure 7:
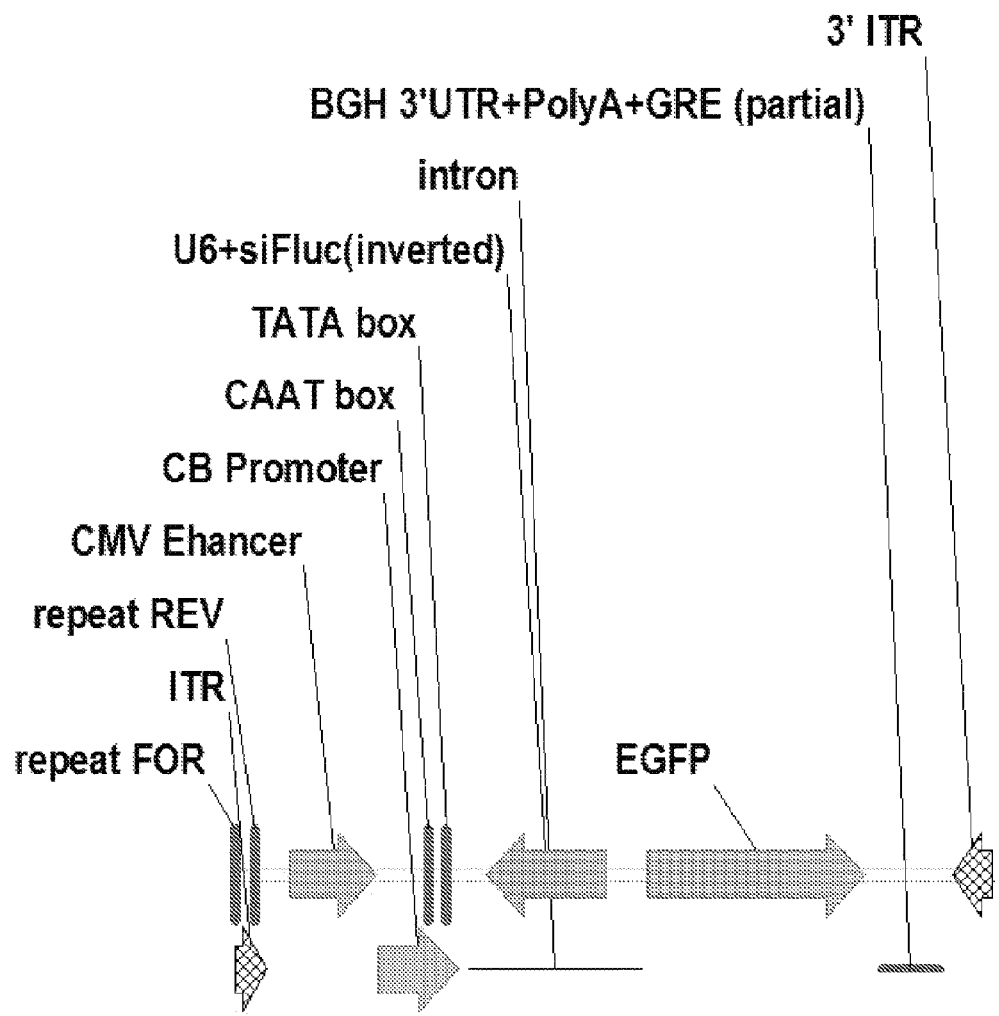
FIG. 7. Map of AAV 5' ΔITR CMV/CB-intron-U6shFluc$^{inv}$-intron-eGFP 3'ITR(C2).
Figure 8:
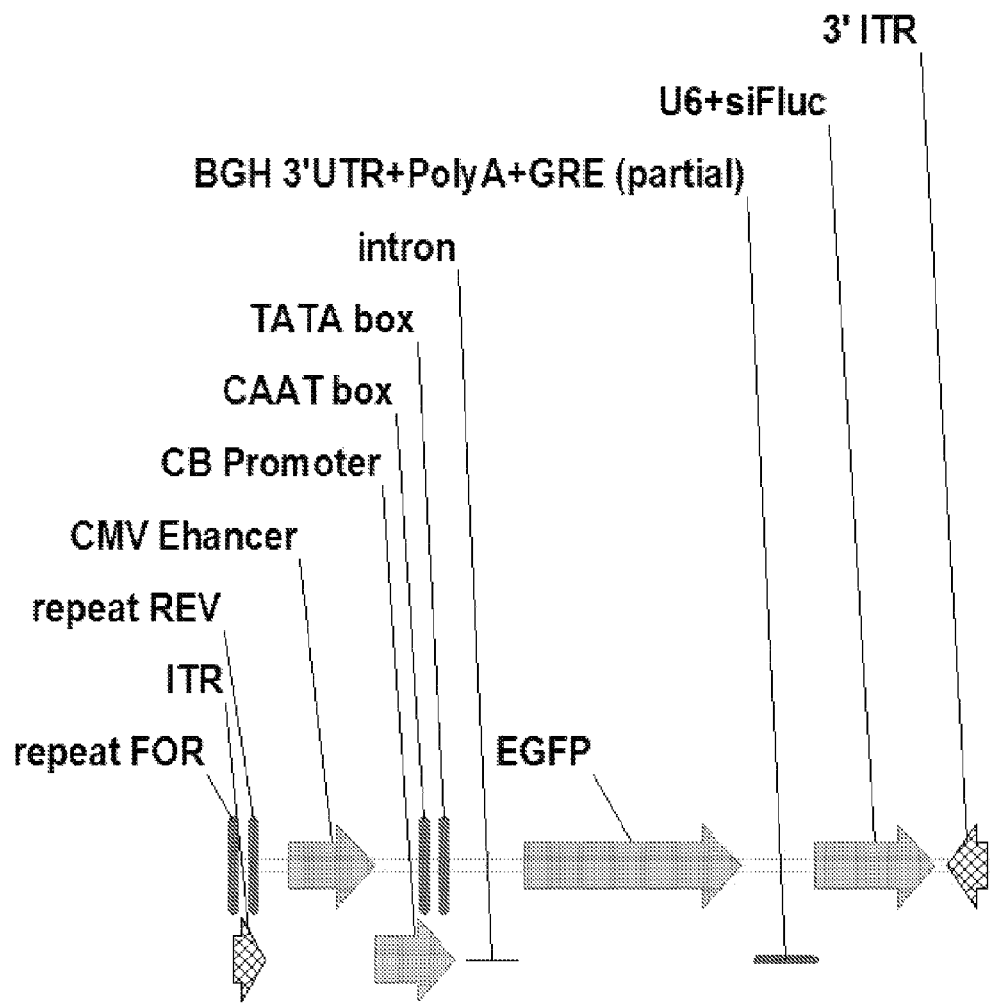
FIG. 8. Map of AAV 5'ΔITR CMV/CB-intron-eGFP U6shFluc 3' ITR (D1).
Figure 9:
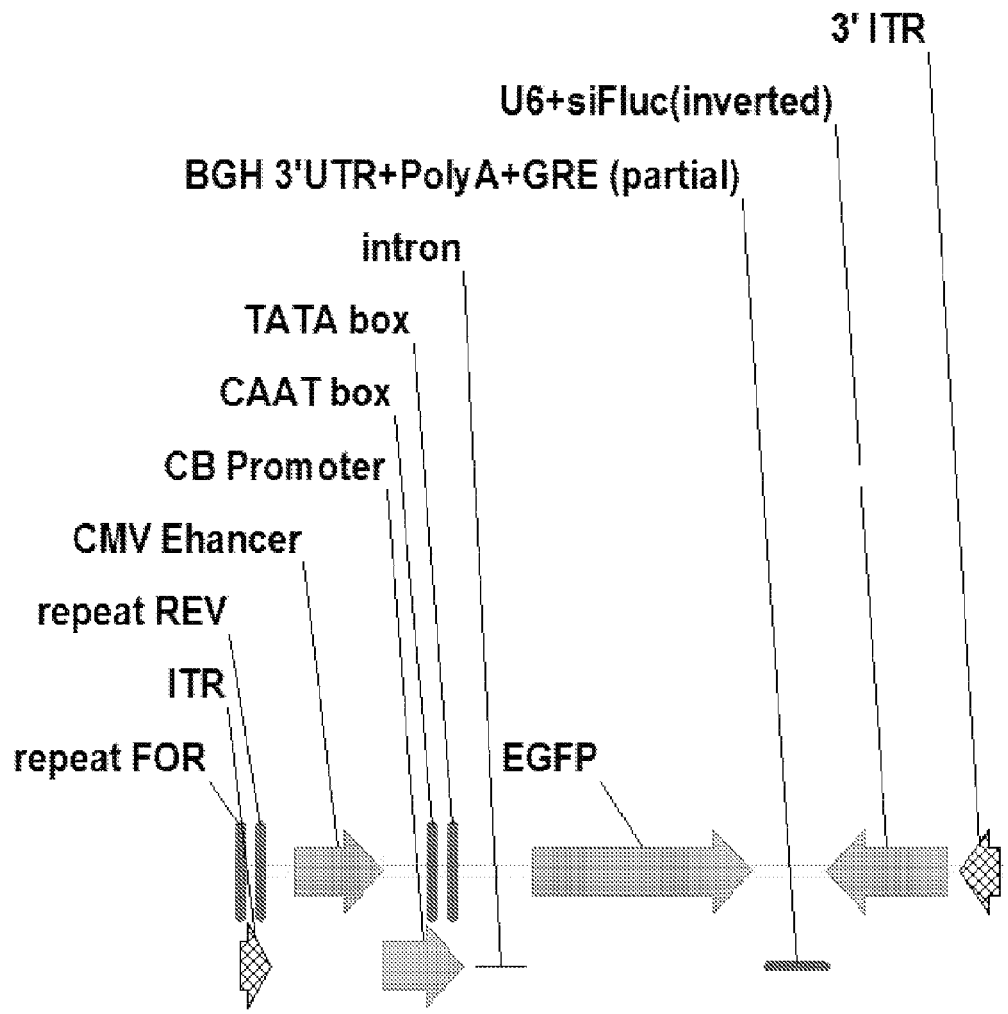
FIG. 9. Map of AAV 5'ΔITR CMV/CB-intron-eGFP U6shFluc$^{inv}$ 3' ITR (D2).

Multicistronic expression constructs allow the expression of a plurality of gene products from a single nucleic acid and are useful in many basic research and therapeutic applications. One beneficial feature of multicistronic expression constructs is the possibility to express two or more gene products from the same nucleic acid construct, achieving simultaneous expression of the two or more gene products in a target cell. For example, some multicistronic expression constructs provided herein allow for expression of a gene product of interest from a first expression cassette of the multicistronic construct, and for monitoring that expression by detecting a reporter expressed from a second expression cassette included in the same multicistronic construct. Multicistronic expression/reporter constructs are of high value in therapeutic and research applications in which expression of the gene product of interest is not easily detectable in a target cell. Examples for such hard-to-detect gene products are non-translated RNAs, such as shRNAs, siRNAs, and microRNAs, as well as proteins that cannot be detected by conventional immunostaining methods, for example, for lack of a suitable antibody. Detecting a reporter expressed from the same nucleic acid construct as the gene product of interest can serve as an efficient proxy for identifying cells that do express the gene product of interest, thus facilitating or enabling monitoring, enrichment, purification, positive and/or negative selection, and observation of cells expressing an otherwise hard or impossible to detect gene product of interest.

Some aspects of this invention are based on the surprising discovery that efficient expression of multiple expression cassettes can be effected from multicistronic expression constructs comprising a first expression cassette including an intron, and a second expression cassette positioned within the intron of the first expression cassette, either in the same or in the opposite orientation of the first expression cassette.

Some aspects of this invention are related to the surprising discovery that such nested multicistronic expression constructs can be introduced into an AAV genome, for example, an scAAV genome, and can be efficiently packaged into infectious AAV virus particles.

Multicistronic Nucleic Acid Constructs

General Structure and Definitions

Some aspects of this invention provide multicistronic nucleic acid constructs.

The term "cistron", as used herein, refers to a nucleic acid cassette sufficient for expression of a gene product. In some embodiments, a cistron is an expression cassette. Accordingly, some aspects of this invention provide nucleic acid constructs comprising two or more cistrons, for example, two or more expression cassettes.

The term "nucleic acid construct", as used herein, refers to an isolated or artificially generated construct comprising a nucleic acid molecule. Non-limiting examples of nucleic acid constructs are plasmids, cosmids, bacterial artificial chromosomes, and nucleic acid vectors. The term "vector" is art recognized and refers to any nucleic acid useful to transfer a nucleic acid into a cell. Examples of vectors are plasmid vectors, gene targeting vectors, and viral vectors, for example parvoviral vectors, such as AAV vectors. A vector may comprise a nucleic acid construct in single-stranded or double-stranded form, and may comprise additional molecules, for example, DNA-associated proteins or viral capsid or envelope proteins. Vectors for eukaryotic and prokaryotic cells are well known to those in the art and include, for example, linear and circular DNA or RNA, viral vectors, (e.g., retroviral and parvoviral vectors, such as lentivirus-derived, Moloney murine leukemia virus-derived, adenovirus-derived, and AAV-derived vectors).

The term "isolated", refers to the characteristic of a material as provided herein being removed from its original or native environment (e.g., the natural environment if it is naturally occurring). Therefore, a naturally-occurring polynucleotide or protein or polypeptide present in a living animal is not isolated, but the same polynucleotide or polypeptide, separated by human intervention from some or all of the coexisting materials in the natural system, is isolated. An artificial or engineered material, for example, a non-naturally occurring nucleic acid construct, such as the expression constructs and vectors described herein, are, accordingly, also referred to as isolated. A material does not have to be purified in order to be isolated. Accordingly, a material may be part of a vector and/or part of a composition, and still be isolated in that such vector or composition is not part of the environment in which the material is found in nature.

As used herein, the term "nucleic acid molecule", refers to an isolated or artificially produced polymer of nucleotides. The term includes, but is not limited to, oligonucleotides and polynucleotides, and single-stranded and double-stranded forms, including hybrids, for example, of DNA and RNA strands, or of strands comprising ribonucleotides, deoxyribonucleotides, and/or modified nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "expression cassette", as used herein, refers to a nucleic acid construct comprising nucleic acid elements sufficient for the expression of a gene product. Typically, an expression cassette comprises a nucleic acid encoding a gene product operatively linked to a promoter sequence. The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation. In some embodiments, the promoter is a heterologous promoter. The term "heterologous promoter", as used herein, refers to a promoter that does is not found to be operatively linked to a given encoding sequence in nature. In some embodiments, an expression cassette may comprise additional elements, for example, an intron, an enhancer, a polyadenylation site, a woodchuck response element (WRE), and/or other elements known to affect expression levels of the encoding sequence. Without wishing to be bound by theory, inclusion of an intron in an expression cassette, for example, between the transcriptional start site and an encoding nucleic acid sequence, for example, a protein-encoding cDNA sequence, is believed to result in increased expression levels of the encoding nucleic acid and the encoded gene product as compared to an expression construct not including an intron.

The term "intron" is art recognized and refers to a nucleic acid sequence in an expression cassette that is removed after transcription of a primary transcript by a cellular process termed splicing. Intron sequences generally comprise a splice donor and a splice acceptor and sequences of such donor and acceptor sites are well known to those of skill in the art. The term "positioned within an intron", as used herein, refers to a nucleic acid construct, for example, an expression cassette, that is positioned between a splice donor and a splice acceptor sites of an intronic sequence.

The term "gene product," as used herein, refers to any product encoded by a nucleic acid sequence. Accordingly, a gene product may, for example, be a primary transcript, a mature transcript, a processed transcript, or a protein or peptide encoded by a transcript. Examples for gene products, accordingly, include mRNAs, rRNAs, hairpin RNAs (e.g. microRNAs, shRNAs, siRNAs, tRNAs), and peptides and proteins, for example, reporter proteins or therapeutic proteins.

The term "promoter", as used herein, refers to a nucleotide sequence capable of controlling the expression of a coding sequence or functional RNA. In general, a nucleic acid sequence encoding a gene product is located 3' of a promoter sequence. In some embodiments, a promoter sequence consists of proximal and more distal upstream elements and can comprise an enhancer element. An "enhancer" is a nucleotide sequence that can stimulate promoter activity and may be an innate element of the promoter or a heterologous element inserted to enhance the level or tissue-specificity of a promoter. In some embodiments, the promoter is derived in its entirety from a native gene. In some embodiments, the promoter is composed of different elements derived from different naturally occurring promoters. In some embodiments, the promoter comprises a synthetic nucleotide sequence. It will be understood by those skilled in the art that different promoters will direct the expression of a gene in different tissues or cell types, or at different stages of development, or in response to different environmental conditions or to the presence or the absence of a drug or transcriptional co-factor. Ubiquitous, cell-type-specific, tissue-specific, developmental stage-specific, and conditional promoters, for example, drug-responsive promoters (e.g. tetracycline-responsive promoters) are well known to those of skill in the art. In some embodiments, the promoter is a RNA polymerase I promoter. In some embodiments, the promoter is a RNA polymerase II promoter. In some embodiments, the promoter is a RNA polymerase III promoter. Promoters mediating transcription by recruiting RNA polymerase I (e.g. most rRNA gene promoters), II (e.g. U6 and H1 promoters), or III (e.g. most promoters of protein-encoding genes), are well known to those of skill in the art. While protein encoding nucleic acid sequences are typically expressed from RNA pol II promoters and hairpin RNA encoding nucleic acid sequences from RNA pol III promoters, it is possible to express both types of gene products from either promoter type.

The term "reporter", as used herein, refers to a gene product, encoded by a nucleic acid comprised in an expression construct as provided herein, that can be detected by an assay or method known in the art, thus "reporting" expression of the construct. Reporters and nucleic acid sequences encoding reporters are well known in the art. Reporters include, for example, fluorescent proteins, such as green fluorescent protein (GFP), blue fluorescent protein (BFP), yellow fluorescent protein (YFP), red fluorescent protein (RFP), enhanced fluorescent protein derivatives (e.g. eGFP, eYFP, eRFP, mCherry, etc.), enzymes (e.g. enzymes catalyzing a reaction yielding a detectable product, such as luciferases, beta-glucuronidases, chloramphenicol acetyltransferases, aminoglycoside phosphotransferases, aminocyclitol phosphotransferases, or puromycin N-acetyl-transferases), and surface antigens. Appropriate reporters will be apparent to those of skill in the related arts.

Multicistronic Expression Construct Configuration: Position and Orientation of Cassettes Some aspects of this invention provide multicistronic expression constructs comprising two or more expression cassettes in various configurations.

In different embodiments, multicistronic expression constructs are provided in which the expression cassettes are positioned in different ways. For example, in some embodiments, a multicistronic expression construct is provided in which a first expression cassette is positioned adjacent to a second expression cassette. In some embodiments, a multicistronic expression construct is provided in which a first expression cassette comprises an intron, and a second expression cassette is positioned within the intron of the first expression cassette. In some embodiments, the second expression cassette, positioned within an intron of the first expression cassette, comprises a promoter and a nucleic acid sequence encoding a gene product operatively linked to the promoter.

In different embodiments, multicistronic expression constructs are provided in which the expression cassettes are oriented in different ways. For example, in some embodiments, a multicistronic expression construct is provided in which a first expression cassette is in the same orientation as a second expression cassette. In some embodiments, a multicistronic expression construct is provided comprising a first and a second expression cassette in opposite orientations.

The term "orientation" as used herein in connection with expression cassettes, refers to the directional characteristic of a given cassette or structure. In some embodiments, an expression cassette harbors a promoter 5' of the encoding nucleic acid sequence, and transcription of the encoding nucleic acid sequence runs from the 5' terminus to the 3' terminus of the sense strand, making it a directional cassette (e.g. 5'-promoter/(intron)/encoding sequence-3'). Since virtually all expression cassettes are directional in this sense, those of skill in the art can easily determine the orientation of a given expression cassette in relation to a second nucleic acid structure, for example, a second expression cassette, a viral genome, or, if the cassette is comprised in an AAV construct, in relation to an AAV ITR.

For example, if a given nucleic acid construct comprises two expression cassettes in the configuration

```
5'-promoter 1/encoding sequence 1---promoter2/encoding sequence 2-3',
>>>>>>>>>>>>>>>>>>>>>>>>>       >>>>>>>>>>>>>>>>>>>>>>>>>>
``` the expression cassettes are in the same orientation, the arrows indicate the direction of transcription of each of the cassettes. For another example, if a given nucleic acid construct comprises a sense strand comprising two expression cassettes in the configuration

```
5'-promoter 1/encoding sequence 1---encoding sequence 2/promoter 2-3',
  >>>>>>>>>>>>>>>>>>>>>>>>>>>>>    <<<<<<<<<<<<<<<<<<<<<<<<<<<
``` the expression cassettes are in opposite orientation to each other and, as indicated by the arrows, the direction of transcription of the expression cassettes, are opposed. In this example, the strand shown comprises the antisense strand of promoter 2 and encoding sequence 2.

For another example, if an expression cassette is comprised in an AAV construct, the cassette can either be in the same orientation as an AAV ITR (e.g. the structures given in SEQ ID NOs: 1 and 2), or in opposite orientation. AAV ITRs are directional. For example, the 3'ITR exemplified in SEQ ID NO: 2 would be in the same orientation as the promoter 1/encoding sequence 1 expression cassette of the examples above, but in opposite orientation to the ΔTRS 5'ITR provided in SEQ ID NO: 1, if both ITRs and the expression cassette would be on the same nucleic acid strand.

Exemplary multicistronic expression constructs harboring two expression cassettes, a CMV/CB-intron-eGFP cassette and a U6siFluc expression cassette, in the same orientation are shown in FIGS. 1, 3, 4, 6, and 8. Exemplary constructs harboring the two expression cassettes in opposite orientation to each other are shown in FIGS. 2, 5, 7, and 9.

A large body of evidence suggests that multicistronic expression constructs often do not achieve optimal expression levels as compared to expression systems containing only one cistron. One of the suggested causes of sub-par expression levels achieved with multicistronic expression constructs comprising two ore more promoter elements is the phenomenon of promoter interference (see, e.g., Curtin J A, Dane A P, Swanson A, Alexander I E, Ginn S L. *Bidirectional promoter interference between two widely used internal heterologous promoters in a late-generation lentiviral construct*. Gene Ther. 2008 March; 15(5):384-90; and Martin-Duque P, Jezzard S, Kaftansis L, Vassaux G. *Direct comparison of the insulating properties of two genetic elements in an adenoviral vector containing two different expression cassettes*. Hum Gene Ther. 2004 October; 15(10):995-1002; both references incorporated herein by reference for disclosure of promoter interference phenomenon). Various strategies have been suggested to overcome the problem of promoter interference, for example, by producing multicistronic expression constructs comprising only one promoter driving transcription of multiple encoding nucleic acid sequences separated by internal ribosomal entry sites, or by separating cistrons comprising their own promoter with transcriptional insulator elements. All suggested strategies to overcome promoter interference are burdened with their own set of problems, though. For example, single-promoter driven expression of multiple cistrons usually results in uneven expression levels of the cistrons. Further some promoters cannot efficiently be isolated and isolation elements are not compatible with some gene transfer vectors, for example, some retroviral vectors.

In some embodiments of this invention, a multicistronic expression construct is provided that allows efficient expression of a first encoding nucleic acid sequence driven by a first promoter and of a second encoding nucleic acid sequence driven by a second promoter without the use of transcriptional insulator elements. Various configurations of such multicistronic expression constructs are provided herein, for example, expression constructs harboring a first expression cassette comprising an intron and a second expression cassette positioned within the intron, in either the same or opposite orientation as the first cassette. Other configurations are described in more detail elsewhere herein.

In some embodiments, multicistronic expression constructs are provided allowing for efficient expression of two or more encoding nucleic acid sequences. In some embodiments, the multicistronic expression construct comprises two expression cassettes. In some embodiments, a first expression cassette of a multicistronic expression construct as provided herein comprises an RNA polymerase II promoter and a second expression cassette comprises an RNA polymerase III promoter.

In some embodiments, the multicistronic expression construct provided is a recombinant AAV (rAAV) construct.

AAV and rAAV

Adeno-associated virus (AAV) is a small (20 nm) replication-defective, nonenveloped DNA virus, that depends on the presence of a second virus, for example, adenovirus or herpesvirus, for productive infection. AAV is not known to cause disease and induces a very mild immune response. AAV can infect both dividing and non-dividing cells and stably incorporates its genome into that of the host cell. AAV vectors based on serotype 2 provided a proof-of-concept for non-toxic and stable gene transfer in murine and large animal models. AAV vectors having distinct tissue targeting capabilities have been developed for gene therapy and research applications. Various serotypes of AAV are known in the art. AAV serotype affects tissue tropism of the respective viral particles and allows to target specific cell types or tissues, making AAV vectors attractive for in vivo gene delivery applications in which only a specific cell type or tissue is targeted and/or gene transfer into non-targeted cells or tissues is not desirable.

Wild type AAV particles harbor a single-stranded DNA genome comprising two genes: The AAV rep gene encodes proteins controlling viral replication, structural gene expression, and integration into the host genome. The AAV cap gene encodes capsid structural proteins. The 5' and 3' termini each comprise an inverted terminal repeat region (ITR), which is involved in multiplication of the AAV genome. In some embodiments, an AAV ITR sequence comprises 145 nucleotides. In general, an AAV ITR sequence is a self-complementary nucleic acid structure that is able to form a hairpin, which plays a role in AAV self-priming for synthesis of the second DNA AAV strand during the viral life cycle. An exemplary ITR is described herein as SEQ ID NO: 2. Recombinant AAV (rAAV) vectors are generally produced by replacing the viral genes, or parts thereof, with a heterologous expression cassettes. Typically, rAAV genomes up to about 5 kb in length can efficiently be packaged into infectious viral particles useful for gene transfer. In some embodiments, the rAAV construct is a single-stranded rAAV construct. That is, the rAAV construct contains two ITRs, a 5'ITR and a 3'ITR that comprise a functional TRS each. In some embodiments, one of the ITRs, for example, the 5'ITR is a ΔTRS ITR. In some such embodiments, the AAV construct is a double-stranded, self-complementary AAV (scAAV) construct. For an overview of AAV biology, ITR function, and scAAV constructs, see McCarty D M. *Self-complementary AAV vectors; advances and applications*. Mol. Ther. 2008 October; 16 (10): at pages 1648-51, first full paragraph, incorporated herein by reference for disclosure of AAV and scAAV constructs, ITR function, and role of ΔTRS ITR in scAAV constructs. An exemplary ΔTRS ITR, also referred to as deltaITR, deltaTRS ITR, or ΔITR herein, is described in SEQ ID NO: 1. A rAAV vector comprising a ΔTRS ITR cannot correctly be nicked during the replication cycle and, accordingly, produces a self-complementary, double-stranded AAV (scAAV) genome, which can efficiently be packaged into infectious AAV particles. Various rAAV, ssAAV, and scAAV vectors, as well as the advantages and drawbacks of each class of vector for specific applications and methods of using such vectors in gene transfer applications are well known to those of skill in the art (see, for example, Choi V W, Samulski R J, McCarty D M. *Effects of adeno-associated virus DNAhairpin structure on recombination*. J. Virol. 2005 June; 79(11):6801-7; McCarty D M, Young S M Jr, Samulski R J. *Integration of adeno-associated virus (AAV) and recombinant AAV vectors*. Annu Rev Genet. 2004; 38:819-45; McCarty D M, Monahan P E, Samulski R J. *Self-complementary recombinant adeno-associated virus (scAAV) vectors promote efficient transduction independently of DNA synthesis*. Gene Ther. 2001 August; 8(16):1248-54; and McCarty D M. *Self-complementary AAV vectors; advances and applications*. Mol. Ther. 2008 October; 16(10):1648-56; all references cited in this application are incorporated herein by reference for disclosure of AAV, rAAV, and scAAV vectors).

The term "recombinant AAV construct" refers to an AAV construct comprising an AAV 5'ITR, at least one recombinant expression cassette, and a 3'ITR. In some embodiments, a rAAV vector is packaged into a capsid protein and delivered to a selected target cell. In some embodiments, the transgene is an expression cassette, comprising a nucleic acid sequence heterologous to the AAV sequences, and encoding a gene product. The encoding nucleic acid coding sequence is operatively linked to a regulatory component, for example, a promoter, in a manner permitting transcription, translation, and/or expression of the gene product in a cell of a target tissue. Recombinant AAV based vectors harboring multicistronic expression constructs are provided herein. In some embodiments, rAAV vectors are engineered to target specific cells, cell types, or tissues, for example, liver tissue.

The AAV sequences of a rAAV construct provided herein typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). AAV ITR sequences may be obtained from any known AAV, including presently identified mammalian AAV types.

In addition to the major elements identified above for the rAAV vectors and constructs, a rAAV vector may also include additional transcriptional control elements. Transcriptional control elements are known to those of skill in the art and exemplary elements include transcription initiation, termination, promoter and enhancer sequences, RNA processing signals such as splicing and polyadenylation (polyA) signals, sequences that stabilize cytoplasmic mRNA, sequences that enhance translation efficiency (e.g., Kozak consensus sequences), sequences that enhance protein stability, and, if appropriate, sequences that enhance secretion of the encoded product. A great number of expression control sequences, including promoters which are native, constitutive, inducible and/or tissue-specific, are known in the art and may be utilized.

In some embodiments, transcriptional control elements or sequences impart tissue-specific gene expression capabilities to a multicistronic expression construct as provided herein. In some embodiments, tissue-specific transcriptional control sequences bind tissue-specific transcription factors that induce transcription in a tissue specific manner. Such tissue-specific regulatory sequences (e.g., promoters, enhancers, etc.) are well known in the art.

rAAVs: Production Methods

Methods for obtaining rAAV preparations having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein or fragment thereof; a functional rep gene; a recombinant AAV vector composed of, AAV inverted terminal repeats (ITRs) and an expression cassette encoding a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the invention may be delivered to the packaging host cell using any appropriate genetic element (vector). The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV-DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the invention provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells. Transfection may be achieved, for example, by infecting a cell with an rAAV harboring an rAAV vector.

A "host cell" refers to any cell that harbors, or is capable of harboring, a substance of interest. Often a host cell is a mammalian cell. A host cell may be used as a recipient of an AAV helper construct, an AAV transgene plasmid, e.g., comprising a promoter operably linked with an miRNA inhibitor, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

Nucleic Acid Constructs Harboring Multiple Self-Complementary Nucleic Acid Sequences Some aspects of this invention provide rAAV constructs harboring a heterologous self-complementary nucleic acid sequence, for example, as part of a hairpin RNA expression cassette. Some aspects of this invention relate to the surprising discovery that an expression cassette comprising a nucleic acid sequence encoding a self-complementary RNA positioned in proximity to an AAV-ITR, can efficiently be expressed if the ITR is a ΔTRS ITR, independent of the orientation of the expression cassette. In some embodiments, an AAV expression construct is provided comprising an expression cassette encoding a hairpin RNA in close proximity to a rAAV ΔITR. In some embodiments, proximal positioning refers to the expression cassette and the ΔITR being separated by less than about 500, less than about 400, less than about 300, less than about 250, less than about 200, less than about 100, less than about 50, less than about 25, or less than about 10 nucleotides.

In some embodiments, a multicistronic AAV expression construct is provided comprising an expression cassette encoding a hairpin RNA and oriented in opposite orientation to a second expression cassette comprised in the expression construct. In some embodiments, the hairpin expression cassette is positioned in proximity to the ΔITR.

In some embodiments, a multicistronic AAV expression vector is provided in which a hairpin expression cassette is positioned adjacent to a functional ITR. In some embodiments, the expression cassette and the functional ITR are separated by at least about 150, at least about 200, at least about 300, at least about 400, at least about 500, at least about 600, at least about 700, at least about 800, at least about 900, or at least about 1000 nucleotides.

Methods of Use

The multicistronic expression constructs provided herein are useful in various research and therapeutic applications. In some embodiments, a cell is contacted with an expression construct as provided herein. In some embodiments, the cell expresses a transcript comprising a target sequence corresponding or complementary to a hairpin RNA sequence encoded by the expression construct. In some embodiments, expression of the target sequence is decreased by expression of a corresponding hairpin RNA sequence in the cell. In some embodiments, the effect of expression of a multicistronic expression construct as provided herein on a phenotypic parameter of the cell is monitored after the cell has been contacted with the expression construct. Examples for phenotypic parameters of a cell include, but are not limited to, cell viability, cell survival, cell proliferation rate, cell growth rate, cell shape, cell size, cell volume, cell expression profile, cell surface marker expression, resistance to antibiotic drugs, and cell reaction to drug treatment. Methods of determining and monitoring such parameters are well known to those of skill in the relevant arts.

Some aspects of this invention provide a cell contacted with a multicistronic expression construct provided herein. In some embodiments, the cell comprises the multicistronic expression construct, or a fragment thereof, integrated into the cell's genome. In some embodiments, the cell is a non-human mammalian cell. In some embodiments, the cell is a human cell.

Methods for contacting a cell with a nucleic acid construct, for example, a nucleic acid construct provided herein, are well known to those of skill in the art and include, for example, electroporation of naked nucleic acid constructs, transfection of nucleic acid constructs complexed with transfection agents, such as Fugene or Lipofectamine, or transduction of cells with nucleic acid constructs packaged into viral particles, for example, AAV, or retroviral particles. Delivery vehicles such as liposomes, nanocapsules, microparticles, microspheres, lipid particles, vesicles, and the like, may be used for the introduction of the compositions of the present invention into suitable host cells. In some embodiments, a cell is contacted with an expression construct in vitro. In some embodiments, a cell is contacted in vivo, for example, in a subject. In some embodiments, a cell is obtained from a subject, contacted ex vivo, and subsequently returned to a subject, for example, to the same subject the cell was obtained from.

Recombinant AAV Administration Methods

In some embodiments, the multicistronic rAAV expression constructs provided herein are delivered to a subject in compositions according to any appropriate methods known in the art. The rAAV, preferably suspended in a physiologically compatible carrier (i.e., in a composition), may be administered to a subject, such as, for example, a human, mouse, rat, cat, dog, sheep, rabbit, horse, cow, goat, pig, guinea pig, hamster, chicken, turkey, or a non-human primate (e.g., Macaque).

In some embodiments, delivery of the rAAV expression constructs provided herein to a subject is effected via intravenous injection, e.g., injection into a portal vein. Administration into the bloodstream may be by injection into a vein, an artery, or any other vascular conduit. In some embodiments, rAAVs are injected into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the rAAVs into the vasculature of an isolated limb to potentially enhance transduction into muscle cells or tissue. Moreover, in some embodiments, it may be desirable to deliver the virions to the CNS of a subject. "CNS" refers to all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the invention may comprise an rAAV alone, or in combination with one or more other viruses (e.g., a second rAAV encoding having one or more different transgenes). In some embodiments, a compositions comprise 1, 2, 3, 4, 5, 6, 7, 8, 9, 10, or more different rAAVs each comprising one or more different expression cassettes or configurations.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVS are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in vector genomes/per kilogram of body weight (vg/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, a effective amount of the rAAV is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain preferred embodiments, $10^{12}$ rAAV genome copies is effective to target heart, liver, and pancreas tissues. In some cases, stable transgenic animals are produced by multiple doses of an rAAV.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The rAAV constructs and compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described; (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Compositions and Kits

The multicistronic expression constructs described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder).

The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

Hairpin RNAs and RNAi

Some aspects of this invention provide methods for the use of expression constructs provided herein to effect RNA interference (RNAi) in a target cell. In some embodiments, the construct used to effect RNAi in the target cell is a multicistronic expression construct as provided herein comprising a hairpin RNA expression cassette.

RNAi, a key cellular pathway utilizing double-stranded RNAs, such as shRNAs or microRNAs as provided herein, as sequence-specific regulators, can be harnessed for a wide spectrum of potential therapeutic and basic research applications. RNAi has been proposed as a cellular response to the presence of double-stranded RNA (dsRNA) in the cell. It is believed that dsRNAs, for example, small hairpin RNAs (shRNAs) and microRNAs (miRNAs) are cleaved into ~20-base pair (bp) duplexes of small-interfering RNAs (siRNAs) by Dicer. It is further believed that siRNAs, either exogenously introduced into a cell or generated by Dicer from shRNA, miRNA, or other substrates, bind to the RNA-induces silencing complex ("RISC"), where they are unwound and the sense strand, also called the "passenger strand" is discarded. The antisense strand of the siRNA, also referred to as the "guide strand", complexed with RISC then binds to a complementary target sequence, for example, a target sequence comprised in an mRNA, which is subsequently cleaved by Slicer, resulting in inactivation of the nucleic acid molecule comprising the target sequence. As a result, the expression of mRNAs containing the target sequence is reduced.

Target sequence recognition and binding by the siRNA guide strand is not completely stringent. While guide strands complementary to a given target sequence have been demonstrated to effect efficient target sequence cleavage and inhibition of expression, it is also known in the art that nucleic acid sequences containing sequences corresponding to the siRNA guide strand can also be efficiently targeted. In connection with RNAi, two nucleic acid sequences are referred to as corresponding sequences, if they are either complementary, or if the degree of complementarity is high enough to allow recognition and binding of the target sequence by the guide strand under physiological conditions. Methods and algorithms to engineer efficient siRNA sequences complementary or corresponding to a given target sequence, or to determine whether a given siRNA sequence will effect inhibition of target sequence expression, are well known to those in the art. Suitable algorithms are publicly available (e.g., from Whitehead Institute for Biomedical Research, Cambridge, Mass., at jura.wi.mit.edu/bioc/siRNAextf). Methods to engineer and synthesize hairpin RNAs and nucleic acid sequences encoding such hairpin RNAs are also well known to those of skill in the art. The term "hairpin RNA" refers to a self-complementary, single-stranded RNA comprising a first nucleic acid sequence and a second nucleic acid sequence complementary to the first nucleic acid sequence positioned in a manner that allows the two sequences to anneal. In some embodiments, the two complementary sequences are separated by a third nucleic acid sequence, the hairpin loop sequence, that is not self-complementary and remains single-stranded after the two complementary sequences have annealed to form the double-stranded "stem" region of the hairpin, thus allowing formation of a hairpin structure. In some embodiments, the first nucleic acid sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some embodiments, the first nucleic acid sequence is between about 50 to about 100 nucleotides long. Accordingly, a nucleic acid encoding a hairpin structure comprises a self-complementary sequence that may form a secondary structure by self-annealing of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or about 50 to about 100 consecutive nucleotides forming intramolecular base pairs. In some embodiments, the stem region of a hairpin RNA comprises 1, 2, 3, 4, 5, 6, 7, 8, 9, 10, 11, 12, 13, 14, or 15 base pair mismatches.

A hairpin RNA, accordingly, may be any RNA comprising a self-complementary nucleic acid sequence able to form a hairpin structure, for example, as described above. Non-limiting examples for hairpin RNAs are mRNAs comprising a hairpin structure, tRNAs, "small hairpin RNAs" also referred to as "short hairpin RNAs" (shRNAs) and "micro-RNAs", also referred to as "miRNAs" or miR5. A nucleic acid molecule encoding a hairpin RNA is necessarily a nucleic acid comprising a self-complementary nucleic acid sequence (encoding the stem-loop-stem structure of the hairpin RNA). In single-stranded form, such encoding nucleic acids may form a hairpin structure by self annealing of the self-complementary nucleic acid sequence in analogy to the encoded hairpin RNA. Without wishing to be bound by theory, it is believed that a hairpin RNA expressed in a target cell is processed by the cell's RNAi machinery, as described in more detail elsewhere herein and as known to those of skill in the art, to form a small interfering RNA (siRNA). As described elsewhere herein and as known to those of skill in the related arts, siRNAs can efficiently and specifically inhibit expression of their target gene. Nucleic acid sequences encoding hairpin RNAs and methods and algorithms for designing and generating hairpin RNAs targeted to a given gene are well known to those of skill in the art. As used herein, the term "target sequence" refers to a nucleotide sequence targeted by a nucleic acid molecule, for example a nucleic acid molecule provided herein, as part of the RNAi mechanism. For example, in some embodiments, a target sequence is a sequence of an mRNA encoding a protein to which a given nucleic acid molecule, for example a nucleic acid molecule complexed with RISC would bind. In some embodiments, a target sequence is a sequence that is specific for a transcript to be targeted. For example, in some embodiments, a target sequence of a specific mRNA is a sequence unique to the specific mRNA.

In general, the guide strand of a given siRNA recognizes and binds to a target sequence that is complementary to the guide strand sequence. Stringent complementarity between guide strand and target sequence is, however, not required, as it is known in the art that a guide strand still efficiently recognizes and binds to a target sequence with single or multiple base pair mismatches. Accordingly, while stringent complementarity between guide strand and target sequence is preferred in some embodiments, a sufficient degree of complementarity between guide strand and target sequence is given, where the guide strand sequence and the target sequence are complementary for all but 1, 2, 3, 4, 5, 6, 7, 8, 9, or 10 base pair mismatch. In some embodiments, a sufficient degree of complementarity between guide strand and target sequence is given, where the guide strand sequence and the target sequence share 100%, about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, or about 8%.

RNAi Applications

Various methods and vectors for the expression of siRNAs in a variety of target cells are known in the art, including direct delivery of siRNA complexes or expression from a nucleic acid construct comprising a nucleic acid encoding an siRNA precursor, for example, a hairpin RNA, such as a shRNA or miRNA. In some embodiments, a nucleic acid construct for siRNA expression comprises an expression cassette including a self-complementary nucleic acid sequence encoding a transcript comprising a self-complementary region, for example, a hairpin RNA.

Methods for hairpin RNA and, thus, siRNA expression include, but are not limited to, transient expression methods, for example, methods involving transfection or transduction of non-integrating DNA or RNA constructs into a target cell, or constitutive expression methods, for example, methods involving transfection or transduction of nucleic acid constructs that integrate into the genome of the target cell or are maintained epichromosomally in the target cell.

The function and advantage of these and other embodiments of the present invention will be more fully understood from the examples below. The following examples are intended to illustrate the benefits of the present invention, but do not exemplify the full scope of the invention.

EXAMPLES

Materials and Methods

Nucleic Acid Constructs

In order to test the positional effects in nucleic acid constructs harboring a plurality of expression cassettes and/or a plurality of self-complementary nucleic acid sequences, a series of non-viral and viral expression constructs was generated.

The expression cassettes used were
(1) a CMV/CB-intron-eGFP cassette, comprising a CMV enhancer (SEQ ID NO: 3), a CB promoter (SEQ ID NO: 4), an intron (SEQ ID NO: 5), a nucleic acid encoding enhanced green fluorescent protein (eGFP) (SEQ ID NO: 6), and a 3'UTR/polyadenylation signal/GRE element (SEQ ID NO: 7); and
(2) a U6siFluc cassette (SEQ ID NO: 10), comprising a U6 promoter (SEQ ID NO: 8) and a nucleic acid encoding an shRNA targeting a luciferase mRNA (siFluc) (SEQ ID NO: 9).

Some of the nucleic acid constructs were AAV constructs, further comprising a 5'ΔITR (an inverted terminal repeat lacking a functional terminal resolution site, SEQ ID NO: 2) and a 3'ITR (a functional AAV ITR including a functional TRS, SEQ ID NO: 1). Both ITR and 5'ΔITR sequences comprise self-complementary nucleic acid sequences.

In some of the constructs generated the expression cassettes (1) and (2) were in the same orientation, while in some other constructs they were in opposite, or inverted, orientation to each other. The constructs in which the expression cassettes were in opposite orientation, comprised an inverted U6siFluc cassette, U6Fluc$^{inv}$ (SEQ ID NO: 11). The constructs generated, non-viral constructs A1 and A2, and AAV constructs A, B1, B2, C1, C2, D1, and D2, are disclosed in SEQ ID NOs: 12-20 and the respective vector maps are shown in FIGS. 1-9. For the AAV experiments, construct A, comprising only one expression cassette (the eGFP cassette) served as a control construct.

AAV Genome Copy (GC) Number Titration

The genome copy (GC) number of an AAV vector preparation is a measure of the number of AAV particles with full genome content in that preparation and can be determined by real time PCR, or Q-PCR. Typically, validated controls representing known GC benchmarks are assayed in parallel to a given AAV preparation and the actual GC number can be determined from comparing the results obtained from the benchmark samples to the given AAV preparation.

AAV Infectious Titer Determination (Q-PCR)

AAV titers can be determined by standard techniques, for example, the infectious center assay (ICA). Alternatively, Q-PCR assays can be employed to determine AAV titers. Typically, such Q-PCR assays are based upon limiting dilution of the vector and an endpoint or 50% endpoint determination of viral DNA replication using real-time PCR. AAV vectors may be serially diluted and a cell line expressing AAV rep and cap may be co-infected with these dilutions plus wildtype Ad5 in parallel replicates. The presence of AAV rep and adenovirus helper genes allows for the replication of AAV DNA. After a suitable incubation period, DNA is extracted and endpoint or 50% endpoint determination is performed. Validation samples may be included. A GC:infectivity (GC:I) ratio may be calculated based upon the results of both the GC copy number titration and Q-PCR assay results. The GC:I ratio is used as a measure of infectivity of the preparation with low GC:I ratios indicating more infectious vector lots. The GC:I ratios between different lots of the same serotype are useful in assessing the relative potency of a particular preparation.

Example 1

Figure 10:
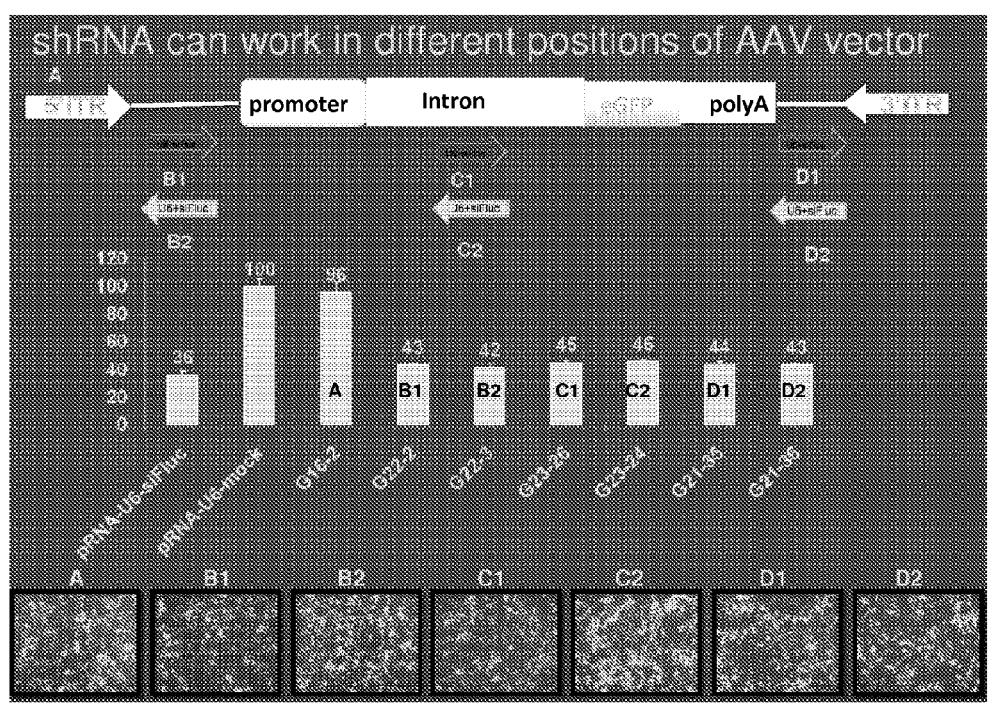
FIG. 10. Functional assessment of shRNA AAV constructs B1-D2.

Expression of eGFP and siRNA from Expression Constructs Comprising an eGFP and a Hairpin Expression Cassette in Different Positional Configurations The AAV constructs A, B1, C1, and D1, comprising the U6siFluc cassette at three different positions (see FIG. 10) were assayed for eGFP expression levels by transfecting mammalian cells with plasmid DNA containing the respective construct. Construct A served as a control construct. FIG. 10 shows representative fluorescence microscopy images of transfected cells. Surprisingly, no significant difference in eGFP fluorescence was observed in cells transfected with the different AAV constructs, indicating that the inclusion of the U6siFluc cassette upstream, downstream, or within the intron of the eGFP expression cassette did not affect overall eGFP expression. The finding that placement of the U6siFluc cassette in proximity to the CMV/CB enhancer/promoter element does not affect eGFP expression is remarkable in that it is contrary to a large body of evidence suggesting that placement of two promoters close to each other can lead to promoter interference with significant inhibition of one or both promoters. Further, our results constitute the first demonstration that positioning a hairpin expression cassette within an intron of a second expression cassette does not affect the expression of the gene product encoded by the second expression cassette.

To compare siFluc expression levels among the AAV constructs mentioned above, they were further assayed for their ability to inhibit expression of their target luciferase mRNA. Cells expressing the target luciferase mRNA were transfected with plasmid DNA comprising the respective construct and luciferase activity was measured subsequent to transfection (FIG. 10). As a negative control, a plasmid RNAi vector, pRNA, comprising a mock hairpin RNA not targeting luciferase under the control of a U6 promoter was transfected to establish a "no knockdown" luciferase expression baseline. Luciferase activity after transfection with negative control pRNA-U6-mock was normalized to a relative value of 100. As a positive knockdown control, a pRNA vector comprising a nucleic acid encoding siFluc (a hairpin RNA targeting luciferase) under the control of a U6 promoter was transfected to establish a level of luciferase expression knockdown achieved with a well established hairpin expression vector. The positive control pRNA-U6-siFluc achieved knockdown of luciferase expression to 36% of the baseline level (FIG. 10). As expected, transfection of the luciferase-expressing cells with construct A, an AAV construct not comprising a siFluc encoding nucleic acid sequence, did not result in appreciable knockdown of luciferase expression (96% luciferase activity). In contrast, transfection of each the AAV constructs B1, C1, and D1 resulted in luciferase expression knockdown to levels comparable to those observed after transfection of the positive control vector (43%-45%). Surprisingly, no appreciable differences in knockdown efficiency were observed between these constructs, suggesting that siRNA expression can efficiently be effected from hairpin RNA expression cassettes at either position.

Together, the eGFP and siFluc expression results indicate that a hairpin expression cassette can be positioned upstream, downstream, or within an intron of a second expression cassette, for example, a reporter expression cassette without affecting the expression level of the hairpin RNA encoded by the hairpin RNA expression cassette or the gene product encoded by the second expression cassette. Further, the results indicate that a hairpin RNA expression cassette can be positioned in close proximity of a promoter of a second expression cassette without affecting the expression levels of the encoded hairpin RNA or the gene product encoded by the second expression cassette, for example, through promoter interference. Finally, a siRNA can efficiently be expressed from a hairpin RNA expression cassette positioned within an intron of a second expression cassette, without affecting the expression level of the gene product, for example, a reporter (e.g., eGFP), encoded by the second expression cassette.

Example 2

Expression of eGFP and siFluc from Constructs Comprising an eGFP Expression Cassette and an siRNA Expression Cassette in Different Orientation Configurations To investigate the effect of the orientation of the hairpin expression cassette relative to the second expression cassette on expression of siFluc and eGFP, constructs B2, C2, and D2, comprising the hairpin RNA expression cassette at the same position as constructs B1, C1, and D1, respectively, but in opposite orientation, were transfected into cells and eGFP expression was examined by fluorescent microscopy. Construct A served as a control construct. FIG. 10, lower shows representative fluorescence microscopy images of cells transfected with the respective constructs. Surprisingly, no significant difference in eGFP fluorescence was observed in cells transfected between the AAV constructs harboring the siFluc expression cassette in the same orientation as the eGFP cassette as compared to the constructs harboring the siFluc expression cassette in the same position, but in opposite orientation (B1 compared to B2, C1 to C2, and D1 to D2). These results indicate that the orientation of the U6siFluc cassette at either of the three positions did not affect overall eGFP expression. The finding that the orientation of the U6siFluc cassette does not affect eGFP expression is remarkable in that a large body of evidence suggests that placement of two expression cassettes in opposite orientation might lead to "collisions" of transcriptional machinery during the transcription process, especially, where the two promoters are oriented in a manner that transcription occurs in the direction of the other promoter. Further, our results constitute the first demonstration that positioning a hairpin expression cassette within an intron of a second expression cassette does not affect the expression of the gene product encoded by the second expression cassette, even if the hairpin expression cassette is in opposite orientation of the first expression cassette.

To compare siFluc expression levels among the AAV constructs mentioned above, they were further assayed for their ability to inhibit expression of their target luciferase mRNA. As described above, cells expressing the target luciferase mRNA were transfected with plasmid DNA comprising the respective construct and luciferase activity was measured subsequent to transfection, using the same positive and negative pRNA controls as described above (FIG. 10). Surprisingly, transfection with the AAV constructs B2, C2, and D2 resulted in luciferase expression knockdown to 42%-46% of baseline levels. The knockdown levels observed with these constructs were comparable to those observed after transfection with the initial AAV constructs harboring the hairpin RNA cassette in the original orientation. The fact that no appreciable differences in knockdown efficiency were observed in constructs harboring the hairpin RNA expression cassette at the same position, but in different orientations (B1 and B2, C1 and C2, D1 and D2, respectively), suggests that siRNA expression can efficiently be effected from hairpin RNA expression cassettes in either orientation.

Together, the eGFP and siFluc expression results indicate that a hairpin expression cassette can be positioned upstream, downstream, or within an intron of a second expression cassette, for example, a reporter expression cassette, and in either the same or in the opposite direction of the second expression cassette, without affecting the expression level of the hairpin RNA encoded by the hairpin RNA expression cassette or the gene product encoded by the second expression cassette. Further, the results indicate that a hairpin RNA expression cassette can be positioned in close proximity of a promoter of a second expression cassette, and in either the same or in the opposite orientation as the second expression cassette, without affecting the expression levels of the encoded hairpin RNA or the gene product encoded by the second expression cassette, for example, through promoter interference. Finally, a siRNA can efficiently be expressed from a hairpin RNA expression cassette positioned within an intron of a second expression cassette, and either in the same or in the opposite orientation as the second expression cassette, without affecting the expression level of the gene product, for example, a reporter (e.g., eGFP), encoded by the second expression cassette.

Example 3

Effect of a Hairpin Expression Cassette on Yield and Titer of AAV Constructs

Figure 11:
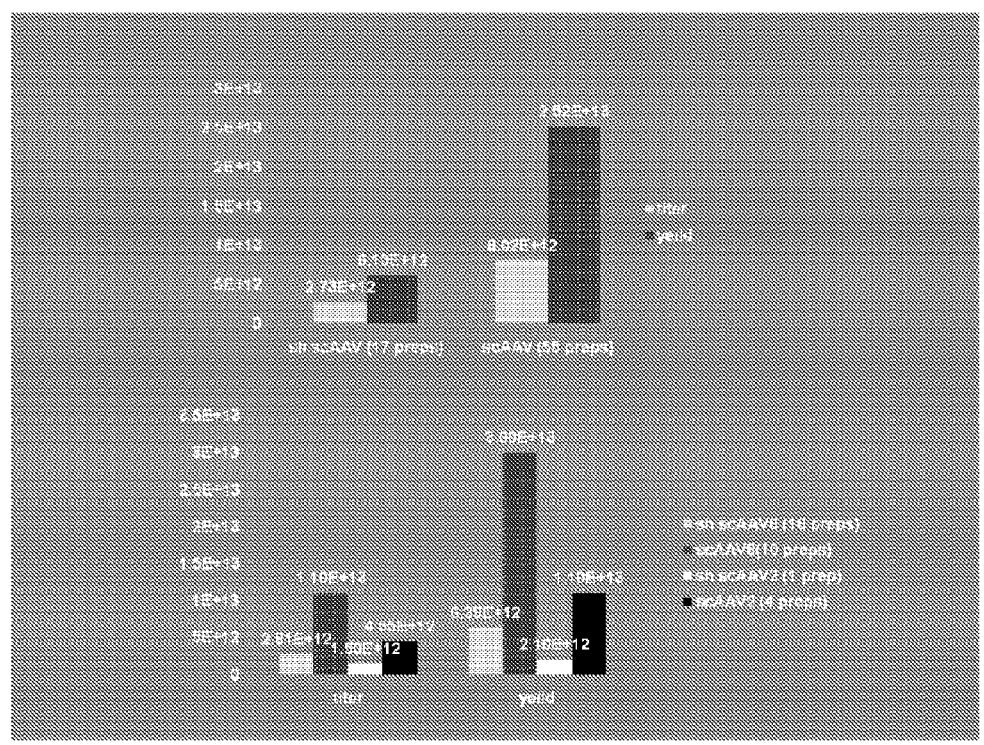
FIG. 11. Effect of shRNA expression cassette on AAV packaging efficiency in different serotypes.

In order to investigate the effect of a hairpin cassette on AAV packaging efficiency, the yield and titer of AAV construct A (no hairpin cassette) was compared to the yield and titer of construct D1 (hairpin expression cassette cloned between eGFP expression cassette and 3'ITR in the same orientation as the eGFP cassette). FIG. 11 shows a comparison of packaging efficiency between these two scAAV vectors (scAAV: AAV construct A; sh scAAV: AAV construct D2).

Both yield and titer were decreased in the sh scAAV vector as compared to non-hairpin scAAV vector, indicating that the presence of a hairpin RNA expression cassette in the configuration of AAV construct D1 can inhibit AAV packaging (FIG. 11, upper panel). These findings were confirmed in different serotypes (AAV2 and AAV8, FIG. 11, lower panel). While both titer and yield varied between serotypes, the inclusion of the hairpin expression cassette in the described configuration resulted in decreased titer and yield of the sh scAAV construct in both serotypes. These results indicate that the presence of a hairpin RNA cassette, a structure comprising a self-complementary nucleic acid sequence, positioned between the eGFP cassette and the 3'ITR in the same orientation as the eGFP cassette, can interfere with the packaging of the scAAV genome.

Example 4

Positional and Orientation Effects of a Hairpin Cassette on Yield and Titer of AAV Constructs In order to investigate whether a hairpin RNA expression cassette could be introduced into an scAAV genome at a different position or in a different orientation than the configuration provided in AAV construct D1 without detrimental effect on AAV genome packaging efficiency, titers and yields of AAV constructs B1-D2 were determined (FIGS. 12-17; 5'ITR (3'-5'): B2; 5'ITR (5'-3'): B1; intron (5'-3'): C2; intron (3'-5'): C1; 3'ITR (3'-5'): D2; 5'ITR (5'-3'): D1; dsAAV shRNA: positive control scAAV vector).

Figure 12:
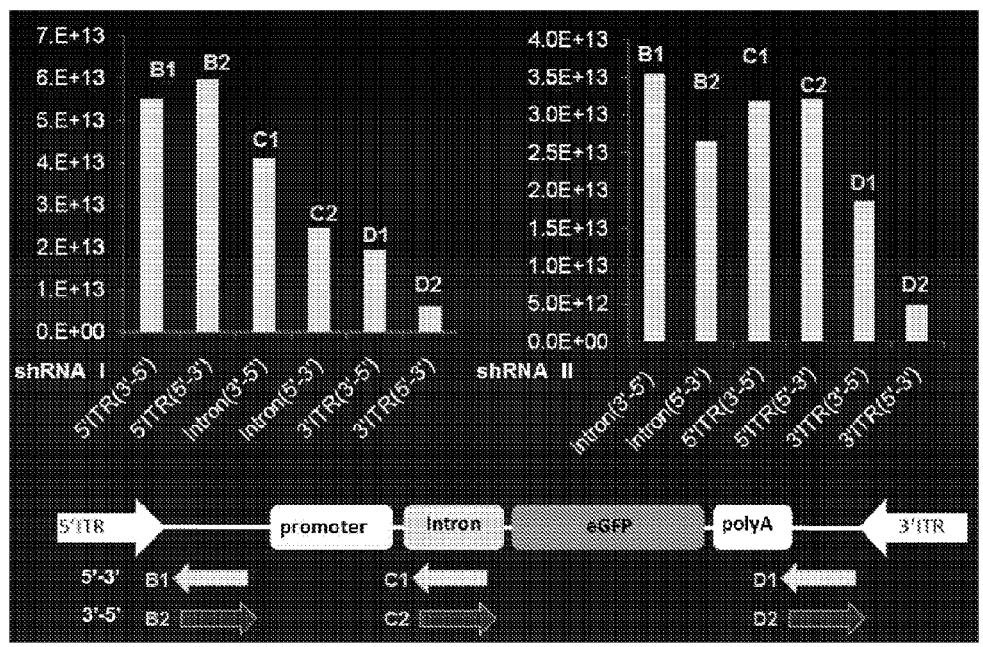
FIG. 12. Effect of shRNA positions on AAV production—AAV titer.

A comparison of packaging efficiencies of constructs B1, B2, C1, C2, D1, and D2 with two different shRNA expression cassettes is shown in FIG. 12. The results indicate that the different shRNA expression cassettes resulted in different packaging efficiencies. More importantly, an shRNA expression cassette positioned proximal to the 3'ITR had a detrimental effect on packaging regardless of shRNA identity. Constructs D1 and D2 were observed to achieve the lowest packaging efficiency with either shRNA, while B1 and B2 could be efficiently packaged with either shRNA expression cassette.

Figure 13:
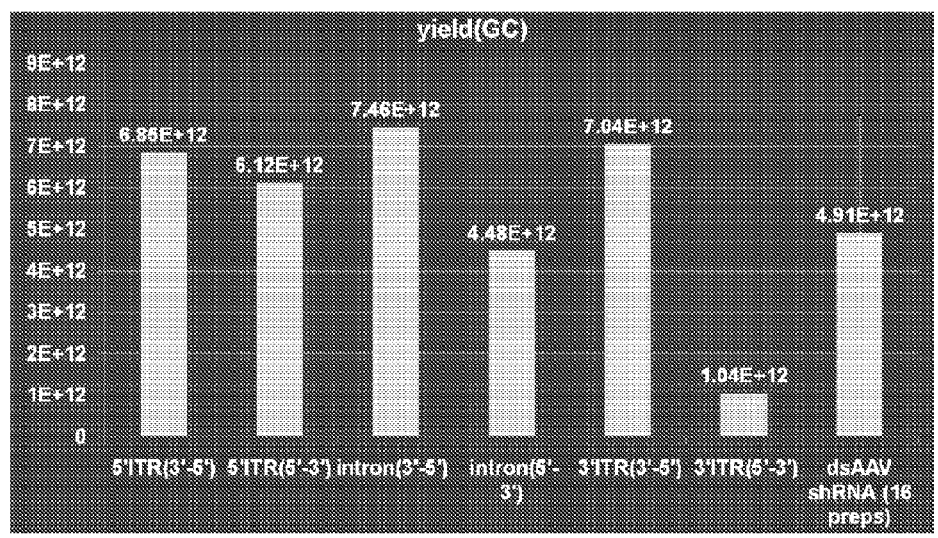
FIG. 13. Effect of hairpin RNA expression construct position and orientation on packaging of AAV constructs.
Figure 14:
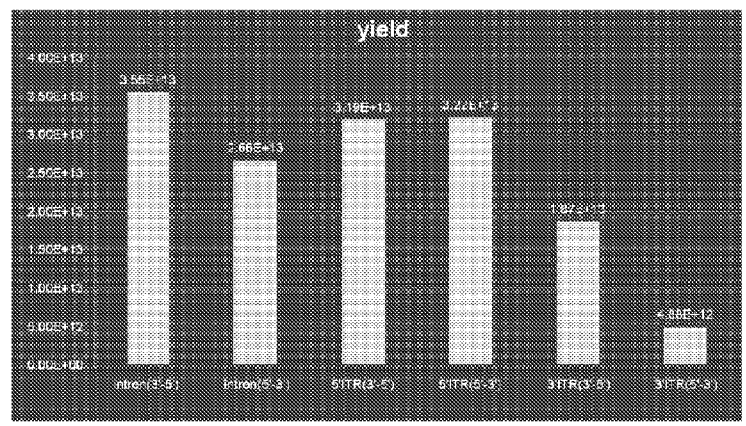
FIG. 14. Effect of hairpin RNA expression construct position and orientation on yield of AAV constructs.

In order to elucidate the packaging efficiencies of the different AAV constructs in more detail, the genome copy number (GC) and the number of AAV particles (VP) was assessed for the 6 different AAV constructs B1-D2 with two different shRNA expression cassettes. Genome copy numbers were analyzed by qPCR for the 6 AAV constructs (FIGS. 13 and 14). FIG. 13 shows the average yield obtained from a control dsAAV shRNA construct as a control. These Figures show that the titers of AAV constructs B1, B2, C1, and C2 were significantly higher than the titer of AAV construct D2. In FIG. 14, the titer of AAV construct D1 was significantly higher than the titer of D2, but did not reach the level of the titers of B1-C2. These data indicate that the positioning of the hairpin RNA cassette in close proximity to the functional 3'ITR is detrimental to efficient AAV genome packaging in both orientations, with the inverted orientation yielding significantly better titers, but still performing subpar as compared to the B or C configurations. It should be noted, that the self-complementary nucleic acid comprised in the hairpin cassette is further removed from the 3'ITR in the D2 configuration than in the D1 configuration, which might explain the elevated titers obtained from the D2 construct configuration. One possible explanation of the observed phenomenon is that the self-complementary nucleic acid encoding the hairpin RNA interferes with the formation of the 3'ITR secondary structure required for correct genome nicking. This might lead to increased generation of AAV genome concatemers that cannot be packaged.

The results of the yield determination of the different AAV constructs was similar: AAV constructs B1-C2 achieved yields comparable to or higher than those obtained with the positive control vector, while AAV construct D1 yields were significantly diminished (FIG. 14). Interestingly, AAV construct D2 yields were comparable to those of AAV constructs B1-C2, indicating that D2 achieves AAV preparations of similar yield, but of diminished infectivity as compared to constructs B1-C2.

Figure 15:
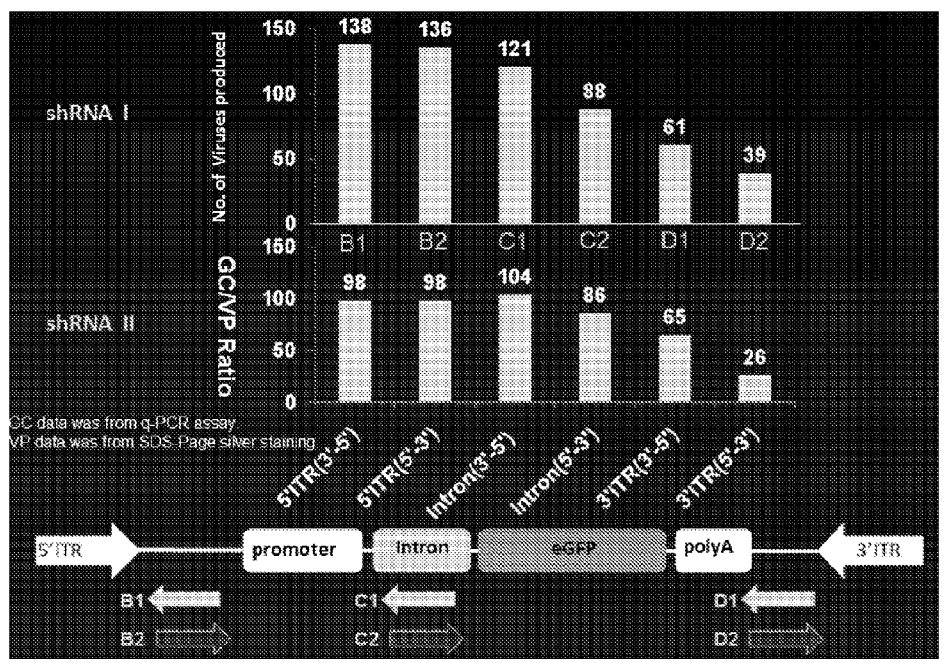
FIG. 15. Effect of shRNA position on AAV production-genome copy to particle ratio.
Figure 16:
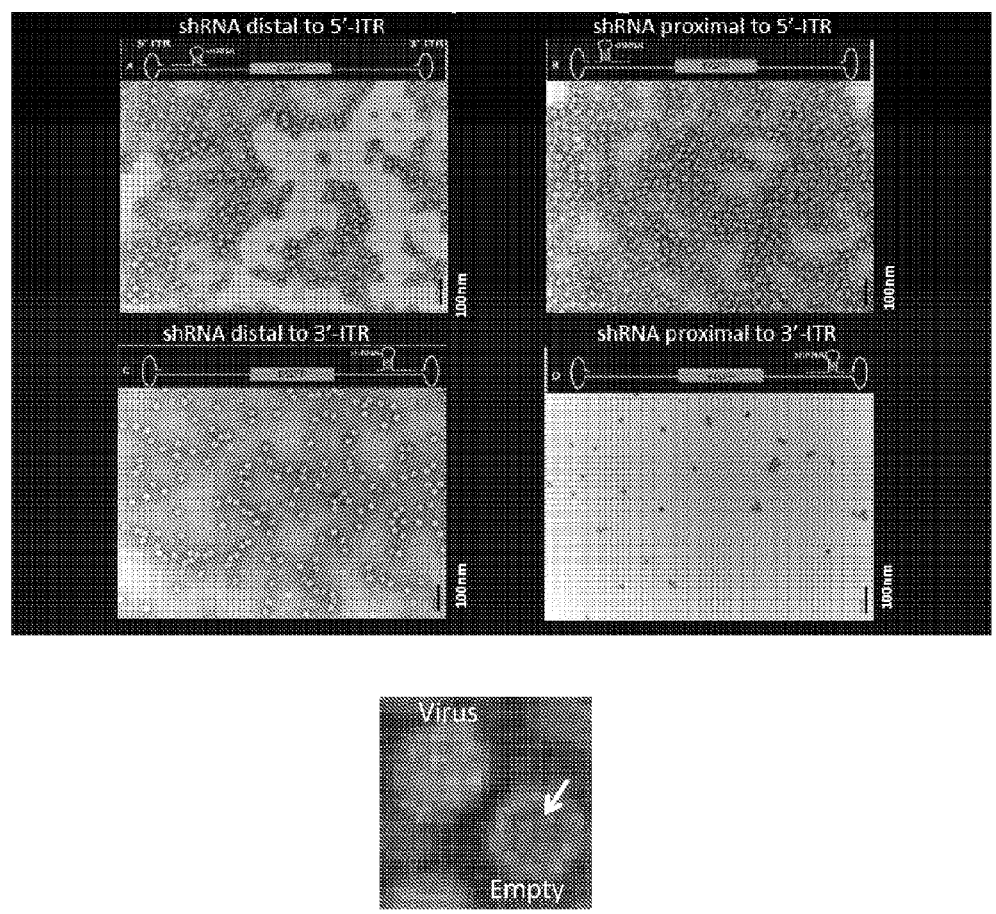
FIG. 16. AAV particles produced from different AAV constructs.

Viral particle number was assessed for the 6 AAV constructs by SDS-PAGE and GC/VP ratios were calculated for each construct (FIG. 15). While constructs B1, B2, and C1 showed similar GC/VP ratios, C1 showed a slight decrease in GC/VP ratio, D2 showed a further decrease, and D1 showed the lowest ratio for both shRNA expression cassettes assessed. Based on this observation, it was hypothesized that introduction of an shRNA expression cassette close to the 3'ITR of the AAV constructs might result in the formation of more empty particles during AAV production. This hypothesis was confirmed by electron microscopy of AAV virions produced from four different constructs as shown in FIG. 16. Both constructs having the shRNA expression cassette between the 5'ITR and the EGFP coding sequence (upper two panels) showed normal morphology and quantity of virions. In contrast, both AAV constructs having shRNA expression cassette between the 3'ITR and the EGFP coding sequence (lower two panels) showed a remarkably reduced number of virions and abnormal virion morphology.

FIG. 16 further shows a differential effect on packaging that is dependent on whether the shRNA expression cassette is positioned proximally or distally from the closest ITR. For example, an shRNA cassette positioned proximally to the 3'ITR resulted in the lowest number of virions (lower right panel), while an shRNA cassette inserted distally to the 3'ITR resulted in a slightly higher number of virions.

Figure 17:
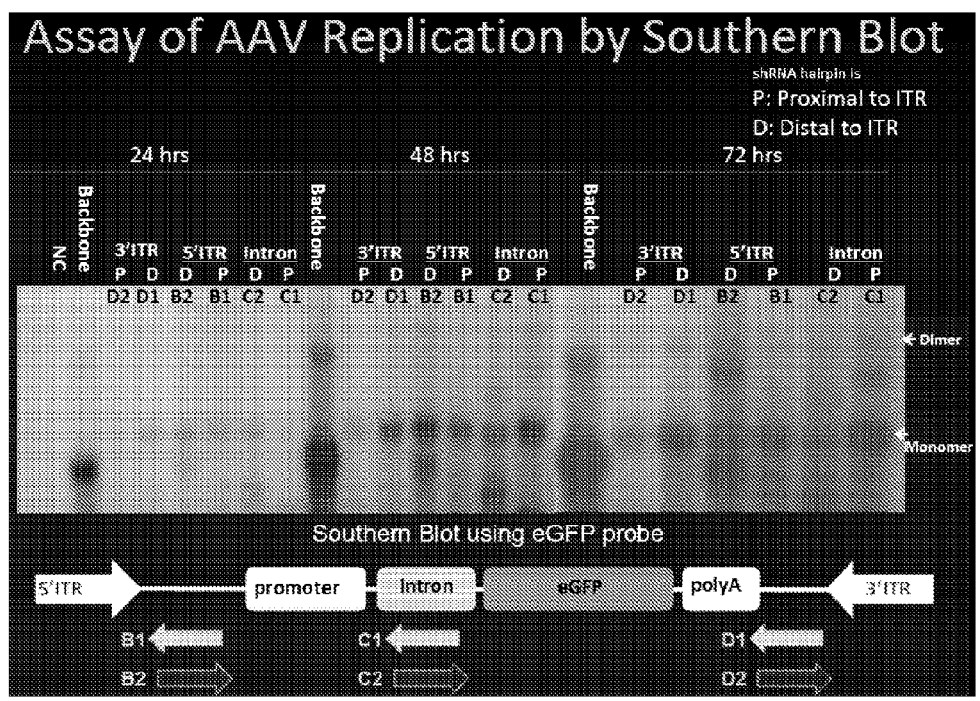
FIG. 17. Replication of different AAV constructs.

Southern blot analysis of AAV replication was assessed for all AAV constructs at three different time points and the data obtained is shown in FIG. 17.

Figure 18:
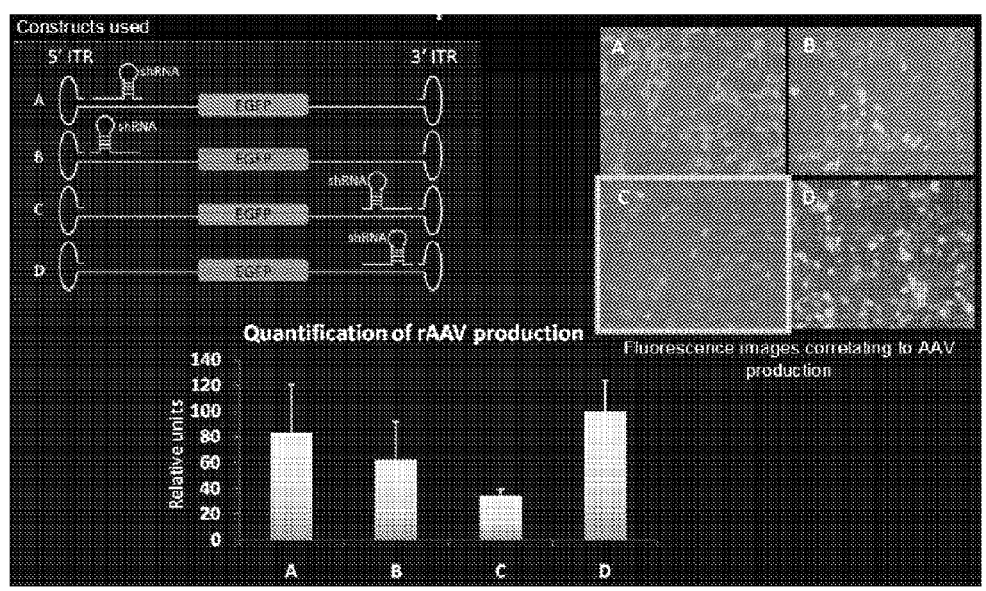
FIG. 18. Effect of shRNA position on single-stranded AAV production.

FIG. 18 shows the positional effects of shRNA expression cassettes in a single stranded AAV constructs on AAV production efficiency. The effects are similar to those observed in scAAV constructs in that an shRNA expression cassette cloned in inverse orientation close to the 3'ITR (Construct C in FIG. 18) resulted in a detrimental effect on packaging efficiency, as assessed by fluorescent imaging. These data support the notion that the results reported herein for positional effects of shRNA cassettes in scAAV vectors are applicable to ssAAV constructs as well.

Together, these results demonstrate that hairpin RNA expression cassettes can efficiently be expressed from scAAV vectors comprising a reporter expression cassette. In order to maximize packaging efficiency, yield, and infectivity of shRNA AAV preparations, the hairpin RNA cassette may be positioned either between the ΔITR and the reporter expression cassette, or within the intron, if present, of the reporter expression cassette. If positioned between the reporter expression cassette and a functional ITR, the hairpin cassette may either be inserted in an orientation in which the promoter of the hairpin RNA cassette is between the self-complementary nucleic acid sequence encoding the hairpin RNA and the functional ITR, or, alternatively, at a minimum distance of at least 300 nucleotides from the ITR, with greater numbers between the self-complementary The resulting multicistronic scAAV constructs can efficiently be packaged and expressed in target cells regardless of the orientation of the hairpin cassette.

REFERENCES

The entire contents of all of the references (including literature references, issued patents, published patent applications, and co-pending patent applications) cited throughout this application are hereby expressly incorporated by reference for the purposes or subject matter referenced herein.

SEQUENCES

The following sequences are exemplary sequences of nucleic acid constructs disclosed herein, or parts thereof. Exemplary nucleic constructs comprising some of the sequences provided below are shown in FIGS. 1-6.

```
5' ΔTRS ITR (5'ΔITR, AAV inverted terminal repeat with terminal
resolution site deleted) (SEQ ID NO: 1):
ctgcgcgctcgctcgctcactgaggccgcccgggcaaagcccgggcgtcgggcgacctttggtcgcccggcctca gtgagcgagcgagcgcgcagagagggagtg 3' ITR (SEQ ID NO: 2):
aggaacccctagtgatggagttggccactccctctctgcgcgctcgctcgctcactgaggccgggcgaccaaagg tcgcccgacgcccgggctttgcccgggcggcctcagtgagcgagcgagcgcgcag CMV enhancer (SEQ ID NO: 3):
     tacggtaaatggcccgcctggctgaccgcccaacgacccgcccattgacgtcaataatgacgtatgtt cccatagtaacgccaatagggactttccattgacgtcaatgggtggagtatttacggtaaactgcccacttggca
```

-continued gtacatcaagtgtatcatatgccaagtacgcccctattgacgtcaatgacggtaaatggcccgcctggcattat gcccagtacatgaccttatgggactttcctacttggcagtacatctactcgaggccacgttctgctt CB promoter (SEQ ID NO: 4):
tctcccatctccccccctccccaccccaattttgtatttatttattttttaattattttgtgcagc gatggggcgggggggggggggggggggcgcgcgccaggcggggcggggcggggcgaggggcggggcgggcga ggcggagaggtgcggcggcagccaatcagagcggcgcgctccgaaagtttccttttatggcgaggcggcggcggc ggcggccctataaaaagcgaagcgcgcggcgggcgggagcgggatc Intron (SEQ ID NO: 5):
gaactgaaaaaccagaaagttaactggtaagtttagtcttttgtcttttatttcaggtcccggatccg gtggtggtgcaaatcaaagaactgctcctcagtggatgttgcctttacttctaggcctgtacggaagtgttactt ctgctctaaaagctgcggaattgtaccc eGFP encoding nucleic acid sequence (SEQ ID NO: 6):
atggtgagcaagggcgaggagctgttcaccggggtggtgcccatcctggtcgagctggacggcgacgtaaacggc cacaagttcagcgtgtccggcgagggcgagggcgatgccacctacggcaagctgaccctgaagttcatctgcacc accggcaagctgcccgtgccctggcccaccctcgtgaccaccctgacctacggcgtgcagtgcttcagccgctac cccgaccacatgaagcagcacgacttcttcaagtccgccatgcccgaaggctacgtccaggagcgcaccatcttc ttcaaggacgacggcaactacaagacccgcgccgaggtgaagttcgagggcgacaccctggtgaaccgcatcgag ctgaagggcatcgacttcaaggaggacggcaacatcctggggcacaagctggagtacaactacaacagccacaac gtctatatcatggccgacaagcagaagaacggcatcaaggtgaacttcaagatccgccacaacatcgaggacggc agcgtgcagctcgccgaccactaccagcagaacacccccatcggcgacggccccgtgctgctgcccgacaaccac tacctgagcacccagtccgccctgagcaaagaccccaacgagaagcgcgatcacatggtcctgctggagttcgtg accgccgccgggatcactctcggcatggacgagctgtacaag BGH 3'UTR/PolyA/GRE(partial) (SEQ ID NO: 7):
ctcgactgtgccttctagttgccagccatctgttgtttgcccctcccccgtgccttccttgaccctgga aggtgccactcccactgtcctttcctaataaaatgaggaaattgcatcgcattgtctgagtaggtgtcattctat tctgggggtggggtggggcaggacagcaaggggaggattgggaagacaat U6 promoter
(SEQ ID NO: 8)
aattccccagtggaaagacgcgcaggcaaaacgcaccacgtgacggagcgtgaccgcgcgccgagcgcg cgccaaggtcgggcaggaagagggcctatttcccatgattccttcatatttgcatatacgatacaaggctgttag agagataattagaattaatttgactgtaaacacaaagatattagtacaaaatacgtgacgtagaaagtaataatt tcttgggtagtttgcagttttaaaattatgttttaa Nucleic acid sequence encoding siFluc:
SEQ ID NO: 9)
aatggactatcatatgcttaccgtaacttgaaagtatttcgatttcttgggtttatatatcttgtggaa aggacgcgggatcccgcttacgctgagtacttcgattc<u>aagagatc</u>gaagtactcagcgtaagtttttccaaa
Bold: first and second nucleic acid sequences encoding stem regions
of hairpin RNA targeting luciferase mRNA; underlined: hairpin
loop region.

U6siFluc (SEQ ID NO: 10):
aattccccagtggaaagacgcgcaggcaaaacgcaccacgtgacggagcgtgaccgcgcgccgagcgcg cgccaaggtcgggcaggaagagggcctatttcccatgattccttcatatttgcatatacgatacaaggctgttag agagataattagaattaatttgactgtaaacacaaagatattagtacaaaatacgtgacgtagaaagtaataatt tcttgggtagtttgcagttttaaaattatgttttaaaatggactatcatatgcttaccgtaacttgaaagtatttt cgatttcttgggtttatatatcttgtggaaaggacgcgggatcccgcttacgctgagtacttcgattcaagagat cgaagtactcagcgtaagtttttccaaa U6siFluc$^{inv}$(SEQ ID NO: 11):

-continued gcttttggaaaaaacttacgctgagtacttcgatctcttgaatcgaagtactcagcgtaagcgggatcc cgcgtcctttccacaagatatataaacccaagaaatcgaaatactttcaagttacggtaagcatatgatagtcca ttttaaaacataattttaaaactgcaaactacccaagaaattattactttctacgtcacgtattttgtactaata tctttgtgtttacagtcaaattaattctaattatctctctaacagccttgtatcgtatatgcaaatatgaaggaa tcatgggaaataggccctcttcctgcccgaccttggcgcgcgctaggcgcgcggtcacgctccgtcacgtggtgc gttttgcctgcgcgtctttccactgggg Non-viral constructs:
Construct A1. CMV/CB-intron-U6Fluc-intron-eGFP, U6Fluc cassette
positioned within intron of eGFP cassette, both expression
cassettes in same orientation (SEQ ID NO: 12, see FIG. 1 for map)
    tacggtaaatggcccgcctggctgaccgcccaacgaccccgcccattgacgtcaataatgacgtatgtt cccatagtaacgccaatagggactttccattgacgtcaatgggtggagtatttacggtaaactgcccacttggca gtacatcaagtgtatcatatgccaagtacgccccctattgacgtcaatgacggtaaatggcccgcctggcattat gcccagtacatgaccttatgggactttcctacttggcagtacatctactcgaggccacgttctgcttcactctcc ccatctcccccccctccccaccccaattttgtatttatttattttttaattattttgtgcagcgatggggcgg ggggggggggggggggcgcgcgccaggcggggcggggcggggcgaggggcggggcggggcgaggcggagaggt gcggcggcagccaatcagagcggcgcgctccgaaagtttcctttatggcgaggcggcggcggcggcggccctat aaaaagcgaagcgcgcggcgggcgggagcgggatcagccaccgcggtggcggccctagagtcgatcgaggaactg aaaaaccagaaagttaactggtaagtttagtcttttgtcttttatttcagaattccccagtggaaagacgcgca ggcaaaacgcaccacgtgacggagcgtgaccgcgcgccgagcgcgcgccaaggtcgggcaggaagagggcctatt tcccatgattccttcatatttgcatatacgatacaaggctgttagagagataattagaattaatttgactgtaaa cacaaagatattagtacaaaatacgtgacgtagaaagtaataatttcttgggtagtttgcagttttaaaattatg ttttaaaatggactatcatatgcttaccgtaacttgaaagtatttcgatttcttgggtttatatatcttgtggaa aggacgcgggatcccgcttacgctgagtacttcgattcaagagatcgaagtactcagcgtaagttttttccaaag tcccggatccggtggtggtgcaaatcaaagaactgctcctcagtggatgttgcctttacttctaggcctgtacgg aagtgttacttctgctctaaaagctgcggaattgtacccgcggccgatccaccggtcgccaccatggtgagcaag ggcgaggagctgttcaccggggtggtgcccatcctggtcgagctggacggcgacgtaaacggccacaagttcagc gtgtccggcgagggcgagggcgatgccacctacggcaagctgaccctgaagttcatctgcaccaccggcaagctg cccgtgccctggcccaccctcgtgaccaccctgacctacggcgtgcagtgcttcagccgctaccccgaccacatg aagcagcacgacttcttcaagtccgccatgcccgaaggctacgtccaggagcgcaccatcttcttcaaggacgac ggcaactacaagacccgcgccgaggtgaagttcgagggcgacaccctggtgaaccgcatcgagctgaagggcatc gacttcaaggaggacggcaacatcctggggcacaagctggagtacaactacaacagccacaacgtctatatcatg gccgacaagcagaagaacggcatcaaggtgaacttcaagatccgccacaacatcgaggacggcagcgtgcagctc gccgaccactaccagcagaacacccccatcggcgacggccccgtgctgctgcccgacaaccactacctgagcacc cagtccgccctgagcaaagaccccaacgagaagcgcgatcacatggtcctgctggagttcgtgaccgccgccggg atcactctcggcatggacgagctgtacaagtaaagcggccatcaagcttatcgataccgtcgactagagctcgct gatcagcctcgactgtgccttctagttgccagccatctgttgtttgcccctcccccgtgccttccttgaccctgg aaggtgccactcccactgtcctttcctaataaaatgaggaaattgcatcgcattgtctgagtaggtgtcattcta ttctggggggtggggtggggcaggacagcaaggggggaggattgggaagacaat Construct A2. CMV/CB-intron-U6Fluc$^{inv}$-intron-eGFP, U6Fluc cassette
positioned within intron of eGFP cassette, expression cassettes in
opposite orientation (SEQ ID NO: 13, see FIG. 2 for map):
    tacggtaaatggcccgcctggctgaccgcccaacgaccccgcccattgacgtcaataatgacgtatgtt cccatagtaacgccaatagggactttccattgacgtcaatgggtggagtatttacggtaaactgcccacttggca gtacatcaagtgtatcatatgccaagtacgcccctattgacgtcaatgacggtaaatggcccgcctggcattat gcccagtacatgaccttatgggactttcctacttggcagtacatctactcgaggccacgttctgcttcactctcc ccatctccccccctccccaccccaattttgtatttatttattttttaattattttgtgcagcgatgggggcgg ggggggggggggggggcgcgcgccaggcggggcggggcggggcgaggggcggggcggggcgaggcggagaggt gcggcggcagccaatcagagcggcgcgctccgaaagtttccttttatggcgaggcggcggcggcggcggccctat aaaaagcgaagcgcgcggcgggcgggagcgggatcagccaccgcggtggcggccctagagtcgatcgaggaactg aaaaaccagaaagttaactggtaagtttagtcttttgtcttttatttcaggcttttggaaaaaacttacgctga gtacttcgatctcttgaatcgaagtactcagcgtaagcgggatcccgcgtcctttccacaagatatataaaccca agaaatcgaaatactttcaagttacggtaagcatatgatagtccattttaaaacataattttaaaactgcaaact acccaagaaattattactttctacgtcacgtattttgtactaatatctttgtgtttacagtcaaattaattctaa ttatctctctaacagccttgtatcgtatatgcaaatatgaaggaatcatgggaaataggccctcttcctgcccga ccttggcgcgcgctcggcgcgcggtcacgctccgtcacgtggtgcgttttgcctgcgcgtctttccactgggggt cccggatccggtggtggtgcaaatcaaagaactgctcctcagtggatgttgcctttacttctaggcctgtacgga agtgttacttctgctctaaaagctgcggaattgtacccgcggccgatccaccggtcgccaccatggtgagcaagg gcgaggagctgttcaccggggtggtgcccatcctggtcgagctggacggcgacgtaaacggccacaagttcagcg tgtccggcgagggcgagggcgatgccacctacggcaagctgaccctgaagttcatctgcaccaccggcaagctgc ccgtgccctggcccaccctcgtgaccaccctgacctacggcgtgcagtgcttcagccgctaccccgaccacatga agcagcacgacttcttcaagtccgccatgcccgaaggctacgtccaggagcgcaccatcttcttcaaggacgacg gcaactacaagacccgcgccgaggtgaagttcgagggcgacaccctggtgaaccgcatcgagctgaagggcatcg acttcaaggaggacggcaacatcctggggcacaagctggagtacaactacaacagccacaacgtctatatcatgg ccgacaagcagaagaacggcatcaaggtgaacttcaagatccgccacaacatcgaggacggcagcgtgcagctcg ccgaccactaccagcagaacacccccatcggcgacggccccgtgctgctgcccgacaaccactacctgagcaccc agtccgccctgagcaaagaccccaacgagaagcgcgatcacatggtcctgctggagttcgtgaccgccgccggga tcactctcggcatggacgagctgtacaagtaaagcggccatcaagcttatcgataccgtcgactagagctcgctg atcagcctcgactgtgccttctagttgccagccatctgttgtttgcccctcccccgtgccttccttgaccctgga aggtgccactcccactgtcctttcctaataaaatgaggaaattgcatcgcattgtctgagtaggtgtcattctat tctgggggggtgggtggggcaggacagcaaggggagggattgggaagacaat AAV constructs:
Construct A. AAV 5'ΔITR CMV/CB -intron-eGFP 3'ITR (SEQ ID NO: 14,
see FIG. 3 for map).
     ctgcgcgctcgctcgctcactgaggccgcccgggcaaagcccgggcgtcgggcgacctttggtcgcccg gcctcagtgagcgagcgagcgcgcagagagggagtgtagccatgctctaggaagatcaattcggtacaattcacg cgtcgacattgattattgactctggtcgttacataacttacggtaaatggcccgcctggctgaccgcccaacgac cccgcccattgacgtcaataatgacgtatgttcccatagtaacgccaatagggactttccattgacgtcaatggg tggagtatttacggtaaactgcccacttggcagtacatcaagtgtatcatatgccaagtacgccccctattgacg tcaatgacggtaaatggcccgcctggcattatgcccagtacatgaccttatgggactttcctacttggcagtaca cccactcgaggccacgttccgcttcactctccccatctccccccctccccaccccaatcttgtacctatttat tttttaattattttgtgcagcgatggggcgggggggggggggggggggcgcgcgccaggcggggcggggcggg gcgaggggcggggcgggcgaggcggagaggtgcggcggcagccaatcagagcggcgcgctccgaaagtttcctt ttatggcgaggcggcggcggcggcggccctataaaaagcgaagcgcgcggcgggcgggagcgggatcagccaccg cggtggcggccctagagtcgatcgaggaactgaaaaaccagaaagttaactggtaagtttagtcttttgtcttt tatttcaggtcccggatccggtggtggtgcaaatcaaagaactgctcctcagtggatgttgcctttacttctagg cctgtacggaagtgttacttctgctctaaaagctgcggaattgtacccgcggccgatccaccggtcgccaccatg gtgagcaagggcgaggagctgttcaccggggtggtgcccatcctggtcgagctggacggcgacgtaaacggccac aagttcagcgtgtccggcgagggcgagggcgatgccacctacggcaagctgaccctgaagttcatctgcaccacc ggcaagctgcccgtgccctggcccaccctcgtgaccaccctgacctacggcgtgcagtgcttcagccgctacccc gaccacatgaagcagcacgacttcttcaagtccgccatgcccgaaggctacgtccaggagcgcaccatcttcttc aaggacgacggcaactacaagacccgcgccgaggtgaagttcgagggcgacaccctggtgaaccgcatcgagctg aagggcatcgacttcaaggaggacggcaacatcctggggcacaagctggagtacaactacaacagccacaacgtc tatatcatggccgacaagcagaagaacggcatcaaggtgaacttcaagatccgccacaacatcgaggacggcagc gtgcagctcgccgaccactaccagcagaacacccccatcggcgacggccccgtgctgctgcccgacaaccactac ctgagcacccagtccgccctgagcaaagaccccaacgagaagcgcgatcacatggtcctgctggagttcgtgacc gccgccgggatcactctcggcatggacgagctgtacaagtaaagcggccatcaagcttatcgataccgtcgacta gagctcgctgatcagcctcgactgtgccttctagttgccagccatctgttgtttgcccctcccccgtgccttcct tgaccctggaaggtgccactcccactgtcctctcctaataaaatgaggaaattgcatcgcattgtctgagtaggt gtcattctattctggggggtggggtggggcaggacagcaaggggagg attgggaagacaattaggtagataagt agcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgag cgcgcag Construct B1. AAV 5'ΔITR U6shFluc CMV/CB -intron-eGFP 3'ITR, U6
promoter between ΔITR and shRNA encoding nucleic acid, expression
cassettes in same orientation (SEQ ID NO: 15, see FIG. 4 for map):
    ctgcgcgctcgctcgctcactgaggccgcccgggcaaagcccgggcgtcgggcgacctttggtcgcccg gcctcagtgagcgagcgagcgcgcagagagggagtgtagccatgctctaggaagatcaattcggtacaattcaaa ttccccagtggaaagacgcgcaggcaaaacgcaccacgtgacggagcgtgaccgcgcgccgagcgcgcgccaagg tcgggcaggaagagggcctatttcccatgattccttcatatttgcatatacgatacaaggctgttagagagataa ttagaattaatttgactgtaaacacaaagatattagtacaaaatacgtgacgtagaaagtaataatttcttgggt agtttgcagttttaaaattatgttttaaaatggactatcatatgcttaccgtaacttgaaagtatttcgatttct tggggtttatatatcttgtggaaaggacgcgggatcccgcttacgctgagtacttcgattcaagagatcgaagtac tcagcgtaagttttttccaaacgcgtcgacattgattattgactctggtcgttacataacttacggtaaatggcc cgcctggctgaccgcccaacgacccc gcccattgacgtcaataatgacgtatgttcccatagtaacgccaatagg gactttccattgacgtcaatgggtggagtatttacggtaaactgcccacttggcagtacatcaagtgtatcatat gccaagtacgccccctattgacgtcaatgacggtaaatggcccgcctggcattatgcccagtacatgaccttatg ggactttcctacttggcagtacatctactcgaggccacgttctgcttcactctccccatctcccccccctcccca ccccaattttgtatttatttattttttaattattttgtgcagcgatgggggcggggggggggggggggggggggcg cgcgccaggcggggcggggcgggcgagggcggggcgggcgaggcggagaggtgcggcggcagccaatcagag cggcgcgctccgaaagtttccttttatggcgaggcggcggcggcggcggccctataaaaagcgaagcgcgcggcg ggcgggagcgggatcagccaccgcggtggcggccctagagtcgatcgaggaactgaaaaaccagaaagttaactg gtaagtttagtcttttgtctttatttcaggtcccggatccggtggtggtgcaaatcaaagaactgctcctcag tggatgttgcctttacttctaggcctgtacggaagtgttacttctgctctaaaagctgcggaattgtacccgcgg ccgatccaccggtcgccaccatggtgagcaagggcgaggagctgttcaccggggtggtgcccatcctggtcgagc tggacggcgacgtaaacggccacaagttcagcgtgtccggcgagggcgagggcgatgccacctacggcaagctga ccctgaagttcatctgcaccaccggcaagctgcccgtgccctggcccaccctcgtgaccaccctgacctacggcg tgcagtgcttcagccgctaccccgaccacatgaagcagcacgacttcttcaagtccgccatgcccgaaggctacg

```
tccaggagcgcaccatcttcttcaaggacgacggcaactacaagacccgcgccgaggtgaagttcgagggcgaca cccctggtgaaccgcatcgagctgaagggcatcgacttcaaggaggacggcaacatcctggggcacaagctggagt acaactacaacagccacaacgtctatatcatggccgacaagcagaagaacggcatcaaggtgaacttcaagatcc gccacaacatcgaggacggcagcgtgcagctcgccgaccactaccagcagaacacccccatcggcgacggccccg tgctgctgcccgacaaccactacctgagcacccagtccgccctgagcaaagaccccaacgagaagcgcgatcaca tggtcctgctggagttcgtgaccgccgcgggatcactctcggcatggacgagctgtacaagtaaagcggccatc aagcttatcgataccgtcgactagagctcgctgatcagcctcgactgtgccttctagttgccagccatctgttgt ttgcccctcccccgtgccttccttgaccctggaaggtgccactcccactgtcctttcctaataaaatgaggaaat tgcatcgcattgtctgagtaggtgtcattctattctggggggtggggtggggcaggacagcaagggggaggattg ggaagacaattaggtagataagtagcatggcgggttaatcattaactacaaggaacccctagtgatggagttggc cactccctctctgcgcgctcgctcgctcactgaggccgggcgaccaaggtcgcccgacgcccgggctttgcccg ggcggcctcagtgagcgagcgagcgcgcag
```

Construct B2. AAV 5'ΔITR U6siFluc^inv CMV/CB -intron-eGFP 3'ITR, U6
promoter flanks shRNA encoding nucleic acid sequence on the opposite
side of the ΔITR, expression cassettes in opposite orientation
(SEQ ID NO: 16, see FIG. 5 for map):

```
     ctgcgcgctcgctcgctcactgaggccgcccgggcaaagcccgggcgtcgggcgacctttggtcgcccg gcctcagtgagcgagcgagcgcgcagagagggagtgtagccatgctctaggaagatcaattcggtacaattcagc ttttggaaaaaacttacgctgagtacttcgatctcttgaatcgaagtactcagcgtaagcgggatcccgcgtcct ttccacaagatatataaacccaagaaatcgaaatactttcaagttacggtaagcatatgatagtccattttaaaa cataattttaaaactgcaaactacccaagaaattattactttctacgtcacgtattttgtactaatatctttgtg tttacagtcaaattaattctaattatctctctaacagccttgtatcgtatatgcaaatatgaaggaatcatggga aataggccctcttcctgcccgaccttggcgcgcgctcggcgcgcggtcacgctccgtcacgtggtgcgttttgcc tgcgcgtctttccactggggcgcgtcgacattgattattgactctggtcgttacataacttacggtaaatggccc gcctggctgaccgcccaacgacccgcccattgacgtcaataatgacgtatgttcccatagtaacgccaataggg actttccattgacgtcaatgggtggagtatttacggtaaactgcccacttggcagtacatcaagtgtatcatatg ccaagtacgccccctattgacgtcaatgacggtaaatggcccgcctggcattatgcccagtacatgaccttatgg gactttcctacttggcagtacatctactcgaggccacgttctgcttcactctccccatctcccccccctcccac ccccaatttgtatttatttatttttttaattattttgtgcagcgatgggggcggggggggggggggggggcgc gcgccaggcggggcggggcgggcgaggggcgggccgggcgaggcggagaggtgcggcggcagccaatcagagc ggcgcgctccgaaagtttccttttatggcgaggcggcggcggcggcggccctataaaaagcgaagcgcgcggcgg gcgggagcgggatcagccaccgcggtggcggccctagagtcgatcgaggaactgaaaaaccagaaagttaactgg taagtttagtcttttgtctttattttcaggtcccgatccggtggtggtgcaaatcaaagaactgctcctcagt ggatgttgcctttacttctaggcctgtacggaagtgttacttctgctctaaaagctgcggaattgtacccgcggc cgatccaccggtcgccaccatggtgagcaagggcgaggagctgttcaccggggtggtgcccatcctggtcgagct ggacggcgacgtaaacggccacaagttcagcgtgtccggcgagggcgagggcgatgccacctacggcaagctgac cctgaagttcatctgcaccaccggcaagctgcccgtgccctggcccaccctcgtgaccaccctgacctacggcgt gcagtgcttcagccgctaccccgaccacatgaagcagcacgacttcttcaagtccgccatgcccgaaggctacgt ccaggagcgcaccatcttcttcaaggacgacggcaactacaagacccgcgccgaggtgaagttcgagggcgacac cctggtgaaccgcatcgagctgaagggcatcgacttcaaggaggacggcaacatcctggggcacaagctggagta caactacaacagccacaacgtctatatcatggccgacaagcagaagaacggcatcaaggtgaacttcaagatccg ccacaacatcgaggacggcagcgtgcagctcgccgaccactaccagcagaacacccccatcggcgacggccccgt gctgctgcccgacaaccactacctgagcacccagtccgccctgagcaaagaccccaacgagaagcgcgatcacat
```

-continued ggtcctgctggagttcgtgaccgccgccgggatcactctcggcatggacgagctgtacaagtaaagcggccatca agcttatcgataccgtcgactagagctcgctgatcagcctcgactgtgccttctagttgccagccatctgttgtt tgcccctcccccgtgccttccttgaccctggaaggtgccactcccactgtcctttcctaataaaatgaggaaatt gcatcgcattgtctgagtaggtgtcattctattctgggggg tggggtggggcaggacagcaaggggg gaggattgg gaagacaattaggtagataagtagcatggcgggttaatcattaactacaaggaacccctagtgatggagttggcc actccctctctgcgcgctcgctcgctcactgaggccgggcgaccaaaggtcgcccgacgcccgggctttgcccgg gcggcctcagtgagcgagcgagcgcgcag Construct C1. AAV 5'ΔITR CMV/CB -intron-U6siFluc-intron-eGFP 3'ITR,
U6siFluc cassette positioned within intron of eGFP cassette,
expression cassettes in same orientation (SEQ ID NO: 17, see FIG. 6
for map):

ctgcgcgctcgctcgctcactgaggccgcccgggcaaagcccgggcgtcgggcgacctttggtcgcccg gcctcagtgagcgagcgagcgcgcagagagggagtgtagccatgctctaggaagatcaattcggtacaattcacg cgtcgacattgattattgactctggtcgttacataacttacggtaaatggcccgcctggctgaccgcccaacgac cccgcccattgacgtcaataatgacgtatgttcccatagtaacgccaatagggactttccattgacgtcaatggg tggagtatttacggtaaactgcccacttggcagtacatcaagtgtatcatatgccaagtacgccccctattgacg tcaatgacggtaaatggcccgcctggcattatgcccagtacatgaccttatgggactttcctacttggcagtaca tctactcgaggccacgttctgcttcactctccccatctcccccccctccccacccccaattttgtatttatttat tttttaattattttgtgcagcgatggggg cggggggggggggggggggcgcgcgccaggcgggycggggcggg gcgaggggcggggcggggcgaggcggagaggtgcggcggcagccaatcagagcggcgcgctccgaaagtttcctt ttatggcgaggcggcggcggcggcggccctataaaaagcgaagcgcgcggcgggcgggagcgggatcagccaccg cggtggcggccctagagtcgatcgaggaactgaaaaaccagaaagttaactggtaagtttagtcttttgtcttt tatttcagaattccccagtggaaagacgcgcaggcaaaacgcaccacgtgacggagcgtgaccgcgcgccgagcg cgcgccaaggtcgggcaggaagagggcctatttcccatgattccttcatatttgcatatacgatacaaggctgtt agagagataattagaattaatttgactgtaaacacaaagatattagtacaaaatacgtgacgtagaaagtaataa tttcttgggtagtttgcagttttaaaattatgttttaaaatggactatcatatgcttaccgtaacttgaaagtat ttcgatttcttgggtttatatatcttgtggaaaggacgcgggatcccgcttacgctgagtacttcgattcaagag atcgaagtactcagcgtaagtttttttccaaagtcccggatccggtggtggtgcaaatcaaagaactgctcctcag tggatgttgcctttacttctaggcctgtacgaagtgttacttctgctctaaaagctgcggaattgtacccgcgg ccgatccaccggtcgccaccatggtgagcaagggcgaggagctgttcaccggggtggtgcccatcctggtcgagc tggacggcgacgtaaacggccacaagttcagcgtgtccggcgagggcgagggcgatgccacctacggcaagctga ccctgaagttcatctgcaccaccggcaagctgcccgtgccctggcccaccctcgtgaccaccctgacctacggcg tgcagtgcttcagccgctaccccgaccacatgaagcagcacgacttcttcaagtccgccatgcccgaaggctacg tccaggagcgcaccatcttcttcaaggacgacggcaactacaagacccgcgccgaggtgaagttcgagggcgaca ccctggtgaaccgcatcgagctgaagggcatcgacttcaaggaggacggcaacatcctggggcacaagctggagt acaactacaacagccacaacgtctatatcatggccgacaagcagaagaacggcatcaaggtgaacttcaagatcc gccacaacatcgaggacggcagcgtgcagctcgccgaccactaccagcagaacacccccatcggcgacgccccg tgctgctgcccgacaaccactacctgagcacccagtccgccctgagcaaagaccccaacgagaagcgcgatcaca tggtcctgctggagttcgtgaccgccgccgggatcactctcggcatggacgagctgtacaagtaaagcggccatc aagcttatcgataccgtcgactagagctcgctgatcagcctcgactgtgccttctagttgccagccatctgttgt ttgcccctcccccgtgccttccttgaccctggaaggtgccactcccactgtcctttcctaataaaatgaggaaat tgcatcgcattgtctgagtaggtgtcattctattctggggggtggggtggggcaggacagcaaggggg gaggattg ggaagacaattaggtagataagtagcatggcgggttaatcattaactacaaggaacccctagtgatggagttggc cactccctctctgcgcgctcgctcgctcactgaggccgggcgaccaaaggtcgcccgacgcccgggctttgcccg ggcggcctcagtgagcgagcgagcgcgcag Construct C2. AAV 5'ΔITR CMV/CB -intron-U6siFluc$^{inv}$-intron-eGFP 3'ITR,
U6siFluc cassette positioned within intron of eGFP cassette,
expression cassettes in opposite orientation (SEQ ID NO: 18, see FIG.
7 for map):

ctgcgcgctcgctcgctcactgaggccgcccgggcaaagcccgggcgtgggcgacctttggtcgcccg gcctcagtgagcgagcgagcgcgcagagagggagtgtagccatgctctaggaagatcaattcggtacaattcacg cgtcgacattgattattgactctggtcgttacataacttacggtaaatggcccgcctggctgaccgcccaacgac cccgcccattgacgtcaataatgacgtatgttcccatagtaacgccaatagggactttccattgacgtcaatggg tggagtatttacggtaaactgcccacttggcagtacatcaagtgtatcatatgccaagtacgccccctattgacg tcaatgacggtaaatggcccgcctggcattatgcccagtacatgaccttatgggactttcctacttggcagtaca tctactcgaggccacgttctgcttcactctccccatctcccccccctccccaccccaattttgtatttatttat tttttaattattttgtgcagcgatggggcggggggggggggggggcgcgcgccaggcggggcgggcggg gcgaggggcggggcgggcgaggcggagaggtgcggcggcagccaatcagagcggcgcgctccgaaagtttcctt ttatggcgaggcggcggcggcggccctataaaagcgaagcgcgcggcgggcgggagcgggatcagccaccg cggtggcggccctagagtcgatcgaggaactgaaaaaccagaaagttaactggtaagtttagtcttttgtcttt tatttcaggcttttggaaaaaacttacgctgagtacttcgatctcttgaatcgaagtactcagcgtaagcgggat cccgcgtcctttccacaagatatataaacccaagaaatcgaaatactttcaagttacggtaagcatatgatagtc cattttaaaacataattttaaaactgcaaactacccaagaaattattactttctacgtcacgtattttgtactaa tatctttgtgtttacagtcaaattaattctaattatctctctaacagccttgtatcgtatatgcaaatatgaagg aatcatgggaaataggccctcttcctgcccgaccttggcgcgcgctcggcgcgcggtcacgctccgtcacgtggt gcgttttgcctgcgcgtctttccactgggggtcccggatccggtggtggtgcaaatcaaagaactgctcctcagt ggatgttgccttttacttctaggcctgtacggaagtgttacttctgctctaaaagctgcggaattgtaccgcggc cgatccaccggtcgccaccatggtgagcaagggcgaggagctgttcaccggggtggtgcccatcctggtcgagct ggacggcgacgtaaacggccacaagttcagcgtgtccggcgagggcgagggcgatgccacctacggcaagctgac cctgaagttcatctgcaccaccggcaagctgcccgtgccctggcccaccctcgtgaccaccctgacctacggcgt gcagtgcttcagccgctaccccgaccacatgaagcagcacgacttcttcaagtccgccatgcccgaaggctacgt ccaggagcgcaccatcttcttcaaggacgacggcaactacaagacccgcgccgaggtgaagttcgagggcgacac cctggtgaaccgcatcgagctgaagggcatcgacttcaaggaggacggcaacatcctggggcacaagctggagta caactacaacagccacaacgtctatatcatggccgacaagcagaagaacggcatcaaggtgaacttcaagatccg ccacaacatcgaggacggcagcgtgcagctcgccgaccactaccagcagaacacccccatcggcgacggccccgt gctgctgcccgacaaccactacctgagcacccagtccgccctgagcaaagaccccaacgagaagcgcgatcacat ggtcctgctggagttcgtgaccgccgccgggatcactctcggcatggacgagctgtacaagtaaagcggccatca agcttatcgataccgtcgactagagctcgctgatcagcctcgactgtgccttctagttgccagccatctgttgtt tgcccctcccccgtgccttccttgaccctggaaggtgccactcccactgtcctttcctaataaaatgaggaaatt gcatcgcattgtctgagtaggtgtcattctattctggggggtggggtggggcaggacagcaaggggggaggattgg gaagacaattaggtagataagtagcatggcgggttaatcattaactacaaggaacccctagtgatggagttggcc actccctctctgcgcgctcgctcgctcactgaggccgggcgaccaaaggtcgcccgacgcccgggctttgcccgg gcggcctcagtgagcgagcgagcgcgcag Construct D1. AAV 5'ΔITR CMV/CB -intron-eGFP U6siFluc 3'ITR, U6
promoter flanking shRNA encoding sequence on opposite site of
functional ITR, expression cassettes in same orientation (SEQ ID NO: 19, see FIG. 8 for map):

ctgcgcgctcgctcgctcactgaggccgcccgggcaaagcccgggcgtcgggcgacctttggtcgcccg gcctcagtgagcgagcgagcgcgcagagagggagtgtagccatgctctaggaagatcaattcggtacaattcacg cgtcgacattgattattgactctggtcgttacataacttacggtaaatggcccgcctggctgaccgcccaacgac cccgcccattgacgtcaataatgacgtatgttcccatagtaacgccaatagggactttccattgacgtcaatggg tggagtatttacggtaaactgcccacttggcagtacatcaagtgtatcatatgccaagtacgccccctattgacg tcaatgacggtaaatggcccgcctggcattatgcccagtacatgaccttatgggactttcctacttggcagtaca tctactcgaggccacgttctgcttcactctccccatctcccccccctccccaccccaattttgtatttatttat tttttaattatttttgtgcagcgatgggggcggggggggggggggggggcgcgcgccaggcggggcgggcggg gcgaggggcggggcgggcgaggcggagaggtgcggcggcagccaatcagagcggcgcgctccgaaagtttcctt ttatggcgaggcggcggcggcggcggccctataaaaagcgaagcgcgcggcgggcgggagcgggatcagccaccg cggtggcggccctagagtcgatcgaggaactgaaaaaccagaaagttaactggtaagtttagtcttttgtcttt tatttcaggtcccggatccggtggtggtgcaaatcaaagaactgctcctcagtggatgttgcctttacttctagg cctgtacggaagtgttacttctgctctaaaagctgcggaattgtacccgcggccgatccaccggtcgccaccatg gtgagcaagggcgaggagctgttcaccggggtggtgcccatcctggtcgagctggacggcgacgtaaacggccac aagttcagcgtgtccggcgagggcgagggcgatgccacctacggcaagctgaccctgaagttcatctgcaccacc ggcaagctgcccgtgccctggcccacccttgtgaccaccctgacctacggcgtgcagtgcttcagccgctacccc gaccacatgaagcagcacgacttcttcaagtccgccatgcccgaaggctacgtccaggagcgcaccatcttcttc aaggacgacggcaactacaagacccgcgccgaggtgaagttcgagggcgacaccctggtgaaccgcatcgagctg aagggcatcgacttcaaggaggacggcaacatcctggggcacaagctggagtacaactacaacagccacaacgtc tatatcatggccgacaagcagaagaacggcatcaaggtgaacttcaagatccgccacaacatcgaggacggcagc gtgcagctcgccgaccactaccagcagaacacccccatcggcgacggccccgtgctgctgcccgacaaccactac ctgagcacccagtccgccctgagcaaagaccccaacgagaagcgcgatcacatggtcctgctggagttcgtgacc gccgccgggatcactctcggcatggacgagctgtacaagtaaagcggccatcaagcttatcgataccgtcgacta gagctcgctgatcagcctcgactgtgccttctagttgccagccatctgttgtttgcccctcccccgtgccttcct tgaccctggaaggtgccactcccactgtcctttcctaataaaatgaggaaattgcatcgcattgtctgagtaggt gtcattctattctggggggtggggtggggcaggacagcaaggggggaggattgggaagacaaaattccccagtgga aagacgcgcaggcaaaacgcaccacgtgacggagcgtgaccgcgcgccgagcgcgcgccaaggtcgggcaggaag agggcctatttcccatgattccttcatatttgcatatacgatacaaggctgttagagagataattagaattaatt tgactgtaaacacaaagatattagtacaaaatacgtgacgtagaaagtaataatttcttgggtagtttgcagttt taaaattatgttttaaaatggactatcatatgcttaccgtaacttgaaagtatttcgatttcttgggtttatata tcttgtggaaaggacgcgggatcccgttacgctgagtacttcgattcaagagatcgaagtactcagcgtaagtt ttttccaaattaggtagataagtagcatggcgggttaatcattaacta<u>caaggaacccctagtgatggagttggc</u>

<u>cactccctctctgcgcgctcgctcgctcactgaggccgggcgaccaaaggtcgcccgacgcccgggctttgcccg</u>

<u>ggcggcctcagtgagcgagcgagcgcgcag</u>

Bold: hairpin RNA encoding sequence; underlined: 3'ITR. Distance
between hairpin RNA encoding sequence and 3"ITR: 52 nucleotides.

Construct D2. AAV 5'ΔITR CMV/CB -intron-eGFP U6siFluc$^{inv}$ 3'ITR,
U6promoter between shRNA encoding nucleic acid sequence and ITR,
expression cassettes in opposite orientation (SEQ ID NO: 20,
see FIG. 9 for map):

ctgcgcgctcgctcgctcactgaggccgcccgggcaaagcccgggcgtcgggcgacctttggtcgcccg gcctcagtgagcgagcgagcgcgcagagagggagtgtagccatgctctaggaagatcaattcggtacaattcacg cgtcgacattgattattgactctggtcgttacataacttacggtaaatggcccgcctggctgaccgcccaacgac -continued

```
cccgcccattgacgtcaataatgacgtatgttcccatagtaacgccaatagggactttccattgacgtcaatggg tggagtatttacggtaaactgcccacttggcagtacatcaagtgtatcatatgccaagtacgcccccctattgacg tcaatgacggtaaatggcccgcctggcattatgcccagtacatgaccttatgggactttcctacttggcagtaca tctactcgaggccacgttctgcttcactctccccatctccccccctccccaccccaattttgtatttatttat tttttaattatttgtgcagcgatggggcggggggggggggggggggcgcgcgccaggcggggcgggcggg gcgaggggcggggcggggcgaggcggagaggtgcggcggcagccaatcagagcggcgcgctccgaaagtttcctt ttatggcgaggcggcggcggcggcggccctataaaaagcgaagcgcgcggcgggcgggagcgggatcagccaccg cggtggcggccctagagtcgatcgaggaactgaaaaaccagaaagttaactggtaagtttagtcttttttgtcttt tatttcaggtcccggatccggtggtggtgcaaatcaaagaactgctcctcagtggatgttgcctttacttctagg cctgtacggaagtgttacttctgctctaaaagctgcggaattgtacccgcggccgatccaccggtcgccaccatg gtgagcaagggcgaggagctgttcaccggggtggtgcccatcctggtcgagctggacggcgacgtaaacggccac aagttcagcgtgtccggcgagggcgagggcgatgccacctacggcaagctgaccctgaagttcatctgcaccacc ggcaagctgcccgtgccctggcccaccctcgtgaccaccctgacctacggcgtgcagtgcttcagccgctacccc gaccacatgaagcagcacgacttcttcaagtccgccatgcccgaaggctacgtccaggagcgcaccatcttcttc aaggacgacggcaactacaagacccgcgccgaggtgaagttcgagggcgacaccctggtgaaccgcatcgagctg aagggcatcgacttcaaggaggacggcaacatcctggggcacaagctggagtacaactacaacagccacaacgtc tatatcatggccgacaagcagaagaacggcatcaaggtgaacttcaagatccgccacaacatcgaggacggcagc gtgcagctcgccgaccactaccagcagaacacccccatcggcgacggccccgtgctgctgcccgacaaccactac ctgagcacccagtccgccctgagcaaagacccccaacgagaagcgcgatcacatggtcctgctggagttcgtgacc gccgcgggatcactctcggcatggacgagctgtacaagtaaagcggccatcaagcttatcgataccgtcgacta gagctcgctgatcagcctcgactgtgccttctagttgccagccatctgttgtttgcccctcccccgtgccttcct tgaccctggaaggtgccactcccactgtcctttcctaataaaatgaggaaattgcatcgcattgtctgagtaggt gtcattctattctggggggtggggtggggcaggacagcaaggggggaggattgggaagacaagcttttggaaaaaa cttacgctgagtacttcgatctcttgaatcgaagtactcagcgtaagcgggatcccgcgtccttttccacaagata tataaacccaagaaatcgaaatactttcaagttacggtaagcatatgatagtccattttaaaacataattttaaa actgcaaactacccaagaaattattactttctacgtcacgtattttgtactaatatctttgtgtttacagtcaaa ttaattctaattatctctctaacagccttgtatcgtatatgcaaatatgaaggaatcatgggaaataggccctct tcctgcccgaccttggcgcgcgctcggcgcgcggtcacgctccgtcacgtggtgcgttttgcctgcgcgtctttc cactggggttaggtagataagtagcatggcgggttaatcattaactacaaggaacccctagtgatggagttggcc actccctctctgcgcgctcgctcgctcactgaggccgggcgaccaaaggtcgcccgacgcccgggctttgcccgg gcggcctcagtgagcgagcgagcgcgcag
```
Bold: hairpin RNA encoding sequence; underlined: 3'ITR. Distance between hairpin RNA encoding sequence and 3"ITR: 377 nucleotides.

SCOPE AND EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all methods, reagents, and configurations described herein are meant to be exemplary and that the actual methods, reagents, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the embodiments described herein are presented by way of example only and that, within the scope of the appended claims and equivalents thereto, the invention may be practiced otherwise than as specifically described and claimed. The present invention is directed to each individual feature, system, article, material, reagent, kit, and/or method described herein. In addition, any combination of two or more such features, systems, articles, materials, kits, and/or methods, if such features, systems, articles, materials, reagents, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

The invention claimed is:

1. A recombinant nucleic acid construct, comprising
   a recombinant AAV (rAAV) vector comprising inverted terminal repeats (ITRs);
   a first expression cassette, comprising a nucleic acid encoding a gene product heterologous to the vector under the control of a first promoter positioned between the ITRs of the vector, and an intron, wherein the intron is positioned between the transcriptional start site of the first expression cassette and the nucleic acid encoding the gene product, and
   a second expression cassette, comprising a self-complementary nucleic acid sequence under the control of a second promoter, wherein the second expression cassette is positioned within the intron of the first expression cassette in proximity with the first promoter.

2. The nucleic acid construct of claim 1, wherein the first promoter is an RNA polymerase II promoter.

3. The nucleic acid construct of claim 1, wherein the second promoter is an RNA polymerase III promoter or a U6 or an H1 promoter.

4. A plasmid comprising the nucleic acid construct of claim 1.

5. A composition comprising the nucleic acid construct of claim 1.

6. The composition of claim 5, further comprising a pharmaceutically acceptable salt.

7. A kit, comprising
   a container housing the nucleic acid construct of claim 1.

8. A non-human cell, comprising a nucleic acid construct of claim 1.

9. The cell of claim 8, wherein the cell is comprised in a non-human subject.

10. The recombinant nucleic acid construct of claim 1, wherein the rAAV vector is configured such that the direction of transcription of the first expression cassette and the direction of transcription of the second expression cassette are opposed.

11. The recombinant nucleic acid construct of claim 1, wherein the rAAV vector is configured such that the direction of transcription of the first expression cassette and the direction of transcription of the second expression cassette are the same.

12. The recombinant nucleic acid construct of claim 1, wherein the gene product is a reporter protein.

13. The recombinant nucleic acid construct of claim 12, wherein the reporter protein is a fluorescent protein, enzyme or surface antigen.

14. The recombinant nucleic acid construct of claim 1, wherein the self-complementary nucleic acid encodes self-complementary RNA.

15. The recombinant nucleic acid construct of claim 14, wherein the self-complementary RNA is shRNA or miRNA.

16. The recombinant nucleic acid construct of claim 15, wherein the shRNA or miRNA is complementary to a messenger RNA (mRNA).

17. The recombinant nucleic acid construct of claim 16, wherein the mRNA is human mRNA.

18. The recombinant nucleic acid construct of claim 1, wherein at least one of the ITRs is an AAV1 ITR, AAV2 ITR, AAV3 ITR, AAV4 ITR, AAV5 ITR, or AAV6 ITR.

19. The recombinant nucleic acid construct of claim 1, wherein one of the ITRs lacks a functional terminal resolution site.

20. The recombinant nucleic acid construct of claim 19, wherein the ITR lacking a functional terminal resolution site is a ΔTRS ITR.

21. A method, comprising
    contacting a cell expressing a target gene with the nucleic acid construct of claim 1.

22. The method of claim 21, wherein the gene product is a reporter, and wherein the method further comprises detecting expression of the reporter in the cell.

23. The method of claim 21, further comprising determining a change in the phenotype of the cell after the contacting.

* * * * *